(12) United States Patent
Edgar

(10) Patent No.: US 12,402,828 B2
(45) Date of Patent: Sep. 2, 2025

(54) METHODS FOR THE DETECTION OF BRAIN INJURY

(71) Applicant: THE CHILDREN'S HOSPITAL OF PHILADELPHIA, Philadelphia, PA (US)

(72) Inventor: James Christopher Edgar, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 523 days.

(21) Appl. No.: 17/438,483

(22) PCT Filed: Mar. 13, 2020

(86) PCT No.: PCT/US2020/022581
§ 371 (c)(1),
(2) Date: Sep. 13, 2021

(87) PCT Pub. No.: WO2020/186148
PCT Pub. Date: Sep. 17, 2020

(65) Prior Publication Data
US 2022/0151534 A1 May 19, 2022

Related U.S. Application Data

(60) Provisional application No. 62/817,737, filed on Mar. 13, 2019.

(51) Int. Cl.
*A61B 5/374* (2021.01)
*A61B 5/00* (2006.01)
*A61B 5/245* (2021.01)

(52) U.S. Cl.
CPC .............. *A61B 5/374* (2021.01); *A61B 5/245* (2021.01); *A61B 5/4848* (2013.01); *A61B 2503/06* (2013.01)

(58) Field of Classification Search
None
See application file for complete search history.

(56) References Cited

U.S. PATENT DOCUMENTS 5,611,350 A 3/1997 John
10,342,480 B2 7/2019 Roberts et al.
(Continued)

OTHER PUBLICATIONS

Arakaki et al., Alpha desynchronization/synchronization during working memory testing is compromised in acute mild traumatic brain injury (mTBI), PLoS One 13(2):e0188101, published Feb. 14, 2018 (Year: 2018).*
(Continued)

*Primary Examiner* — Yi-Shan Yang
(74) *Attorney, Agent, or Firm* — Robert C. Netter, Jr.; Dann, Dorfman, Herrell & Skillman

(57) ABSTRACT

Methods using measuring alpha activity in the brain are provided for the detection and/or diagnosis of a mild traumatic brain injury in a subject. The methods comprise measuring an alpha activity in the brain of a subject, wherein an increase in the alpha activity in the brain of the subject compared to control subjects without a brain injury or to a baseline of the subject is indicative of the subject having the mild traumatic brain injury. The alpha activity may be measured when the subject is in a resting state. The methods may further comprise administering a therapy such as a pain or headache medication to the subject with a mild traumatic brain injury.

11 Claims, 56 Drawing Sheets

(56) References Cited

U.S. PATENT DOCUMENTS

Figure 1:
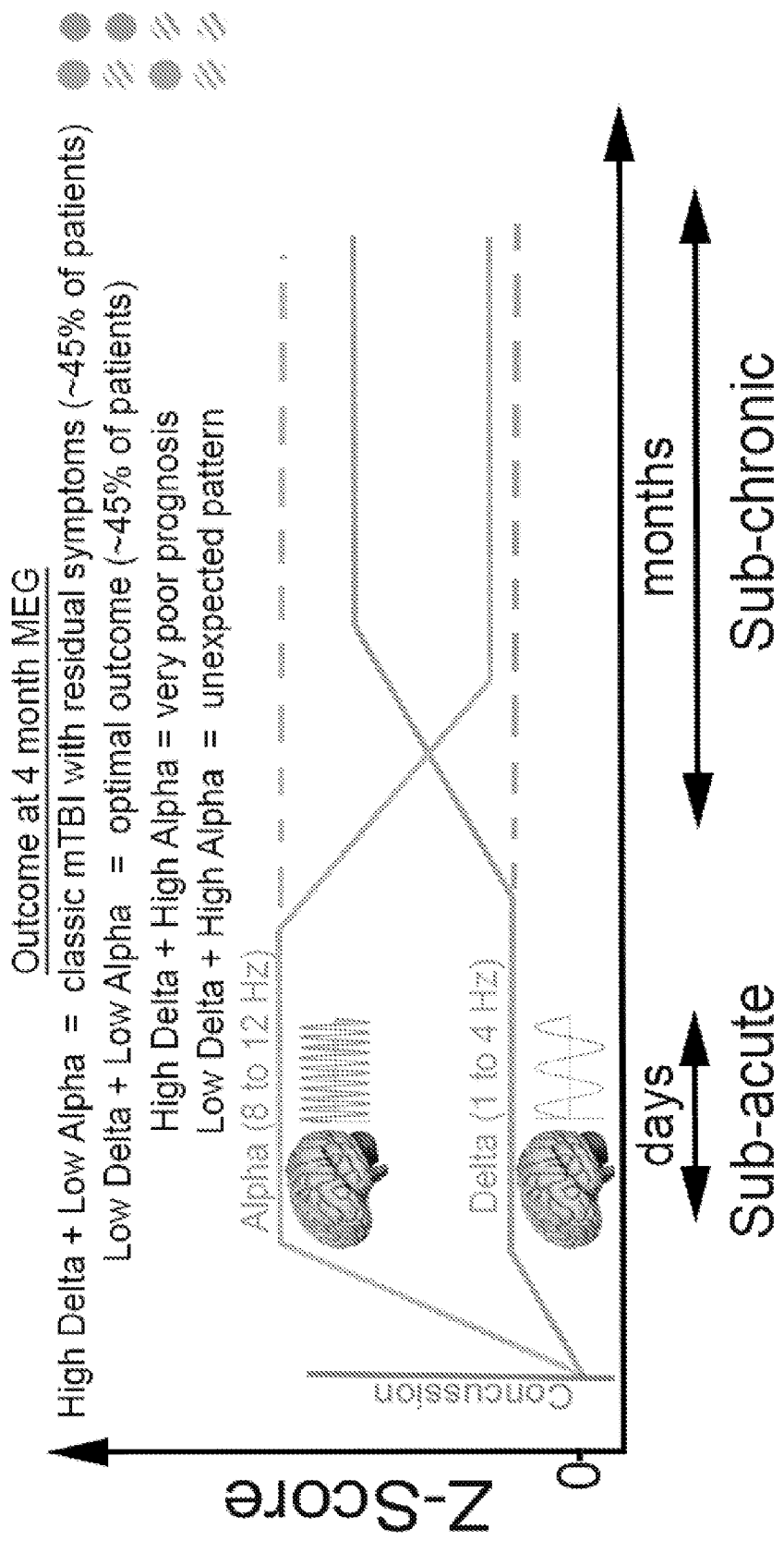

2005/0273017 A1* 12/2005 Gordon .............. A61B 5/4088 600/544
2020/0124588 A1* 4/2020 Peterson ............ G01N 33/6896

OTHER PUBLICATIONS

Li et al., "Brain activation profiles in mTBI: Evidence from combined resting-State EEG and MEG Activity". Conference Proceeding IEEE Med Biol Soc. 2015:6963-6, https://doi.org/10.1109/EMBC.2015.7319994. (Year: 2015).*

Arakaki et al., "Alpha desynchronization/synchronization during working memory testing is compromised in acute mild traumatic brain injury (mTBI)". PLoS One 13(2), Feb. 2018, pp. 1-19, https://doi.org/10.1371/journal.pone.0188101. (Year: 2018).*

Bitbrain, "EEG electrode placement options". Neurotechnology—Science & Research, 2018 Bitbrain Technologies. https://www.bitbrain.com/blog/eeg-electrode-placement (Year: 2018).*

Tebano et al., "EEG Spectral analysis after minor head injury in man". Electroencephalograhy and clinical neurophysiology, 1988, 70, 185-189. (Year: 1988).*

Klem et al., "The ten-twenty electrode system of the international Federation". Electroencephalogr. Clin. Neurophysiol., 1999, 52, pp. 3-6. (Year: 1999).*

Silverman et al., "The rationale and history of the 10-20 system of the International Federation". American Journal of EEG Technology, 1963, 3(a), 17-22. (Year: 1963).*

Arakaki, et al., "Alpha desynchronization/synchronization during working memory testing is compromised in acute mild traumatic brain injury (mTBI)" PLoS One (2018) 13(2):e0188101.

Tebano, et al., "EEG spectral analysis after minor head injury in man" Electroencephalogr. Clin. Neurophys. (1988) 70:185-189.

Reddy, et al., "Neurofeedback training to enhance learning and memory in patients with traumatic brain injury: A single case study" Ind. J. Neurotrauma (2009) 6(1):87-90.

Hulkower, et al., "A Decade of DTI in Traumatic Brain Injury: 10 Years and 100 Articles Later" (2013) Am. J. Neuroradiol., 34:2064-74.

Huang, et al., "Single-subject-based whole-brain MEG slow-wave imaging approach for detecting abnormality in patients with mild traumatic brain injury" NeuroImage Clin. (2014) 5:109-119.

Li, et al., "Demystifying signal processing techniques to extract resting-state EEG features for psychologists" Brain Science Advances (2020) 6(3):189-209.

* cited by examiner

METHODS FOR THE DETECTION OF BRAIN INJURY

This application is a § 371 application of PCT/US2020/022581, filed Mar. 13, 2020, which claims priority under 35 U.S.C. § 119 (e) to U.S. Provisional Patent Application No. 62/817,737, filed Mar. 13, 2019. The foregoing applications are incorporated by reference herein.

FIELD OF THE INVENTION

The present invention relates to the detection and diagnosis of a traumatic brain injury, particularly a mild traumatic brain injury.

BACKGROUND OF THE INVENTION

Traumatic brain injury (TBI) afflicts millions of people annually in the United States and is the primary cause of death and disability in young adults and children. TBI often causes enduring disabilities including emotional alterations, cognitive impairment and memory dysfunction. Mild traumatic brain injury (mTBI; e.g., a concussion) can result from blunt force trauma to the head or nonimpact acceleration/deceleration, with resultant closed-head injury and disturbance of consciousness. mTBI is a common injury that can impact academics, behavior, and cognition. The cause of mTBI is varied and includes motor vehicle crashes, sport-related injuries, falls, and assaults.

Traditional brain imaging has not been found to be useful for identifying mTBI (Bigler, et al., Neuroimaging in sports-related brain injury. In Traumatic brain injury in sports: An international perspective. Edited by Lovell et al. (2004) pp. 71-94; Johnston, et al., Clin. J. Sportb Med. (2001) 11:166-175; Kirkwood, et al., Pediatrics (2006) 117:1359-1371; Niogi, et al., J. Head Trauma Rehab. (2010) 25:241-255; Kelly, et al., Amer. J. Neuroradiology (1988) 9:699-708). For example, for mTBI, intracranial lesions were observed with conventional neuroimaging (MRI and CT) in only 4%, 16%, and 28% for Glasgow Coma Scale scores of 15, 14, and 13, respectively (Culotta, et al., Neurosurgery (1996) 38:245-250). The structural damage underlying mild and moderate brain injury is often described as traumatic axonal injury (TAI) - with microscopic white-matter injury thought to be the most important location of structural brain pathology in mTBI (Hulkower, et al., Amer. J. Neuroradiology (2013) 34:2064-2074). Findings indicate, however, that standard diffusion tensor imaging (DTI) clinical interpretation does not detect mTBI in the acute phase or at the individual patient level (Hulkower, et al., Amer. J. Neuroradiology (2013) 34:2064-2074; Strauss, et al., Top. Magnetic Reson. Imaging (2015) 24:353-362).

A means to detect and monitor for traumatic brain injury, especially mild traumatic brain injury, is desirable in order to rapidly and accurately provide a diagnosis and to ensure rapid medical treatment, which is important for a more effective and successful therapy.

SUMMARY OF THE INVENTION

In accordance with the instant invention, methods of detecting, monitoring, and/or diagnosing a traumatic brain injury, particularly a mild traumatic brain injury, in a subject are provided. In a particular embodiment, the method comprises measuring brain activity in the subject by magnetoencephalography (MEG) and/or electroencephalography (EEG). In a particular embodiment, the subject is an adolescent. In a particular embodiment, the resting state brain activity is measured, particularly the eyes-closed resting state. In a particular embodiment, the alpha activity (8-13 Hz) and, optionally, other frequencies such as delta (1 to 4 Hz), theta (4 to 8 Hz), and/or beta (12 to 30 Hz) are measured. In a particular embodiment, the alpha activity (8-13 Hz) and the theta (4 to 8 Hz) and/or beta (12 to 30 Hz) activities are measured. In a particular embodiment, brain activity is examined in source space (brain space) versus sensor space as this approach reduces non-brain artefact in the neural measures (e.g., muscle and heartbeat activity) as well as provides the spatial resolution needed to identify local as well as more diffuse brain trauma. In a particular embodiment, the alpha activity is measured during an acute as well as sub-acute post-concussion period. In a particular embodiment, longitudinally repeated brain measures are obtained (e.g., to provide the most actionable clinical information).

In accordance with another aspect of the instant invention, methods of screening therapies and/or drug candidates for the treatment of a traumatic brain injury, particularly a mild traumatic brain injury, are provided. In a particular embodiment, the method comprises administering a therapy and/or compound to a subject before and/or after a traumatic brain injury and subsequently measuring brain activity in the subject. In a particular embodiment, the method comprises measuring brain activity in the subject by magnetoencephalography (MEG) and/or electroencephalography (EEG). In a particular embodiment, the subject is an adolescent. In a particular embodiment, the resting state brain activity is measured, particularly the eyes-closed resting state. In a particular embodiment, the alpha activity (8-13 Hz) and, optionally, other frequencies such as delta (1 to 4 Hz), theta (4 to 8 Hz), and/or beta (12 to 30 Hz) are measured. In a particular embodiment, the alpha activity (8-13 Hz) and the theta (4 to 8 Hz) and/or beta (12 to 30 Hz) activities are measured. In a particular embodiment, the alpha activity is measured during an acute as well as sub-acute post-concussion period. In a particular embodiment, longitudinally repeated brain measures are obtained (e.g., to provide the most actionable clinical information).

BRIEF DESCRIPTIONS OF THE DRAWING

FIG. 1 provides a schematic model of brain activity in mild traumatic brain injury (mTBI). Possible clinical outcomes associated with clinical magnetoencephalography (MEG) or electroencephalography (EEG) findings are indicated.

Figure 2A:
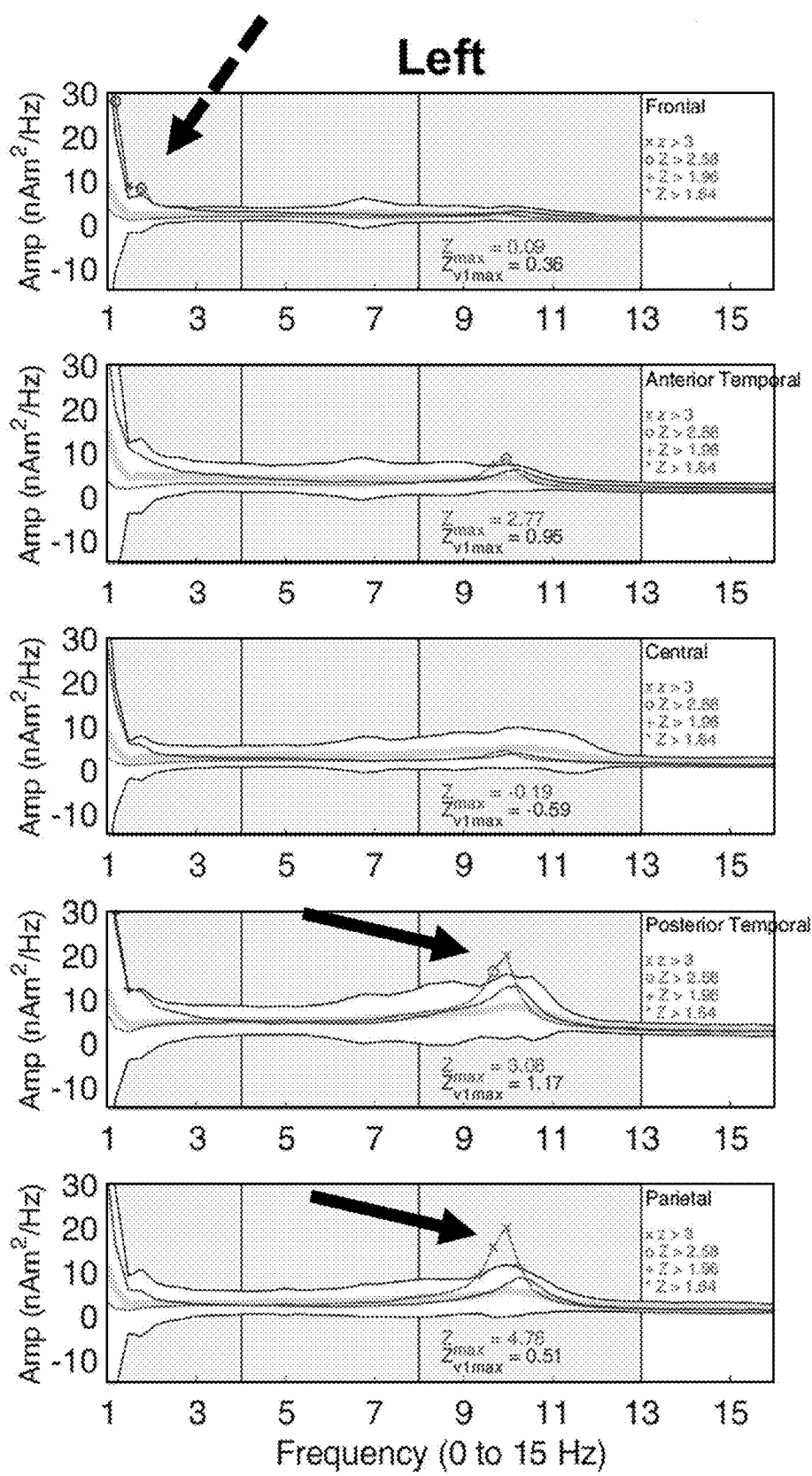
Figure 2B:
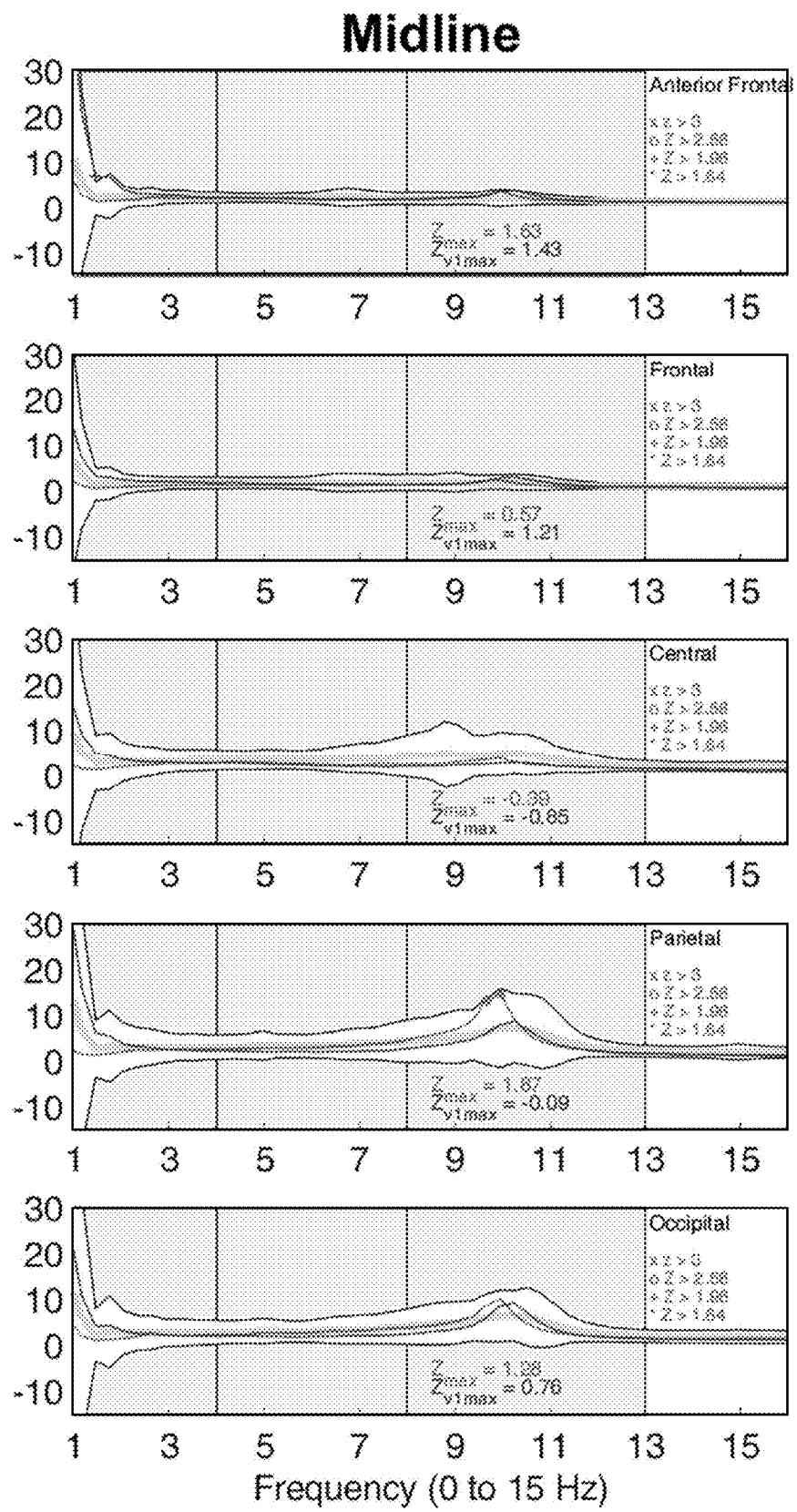
Figure 2C:
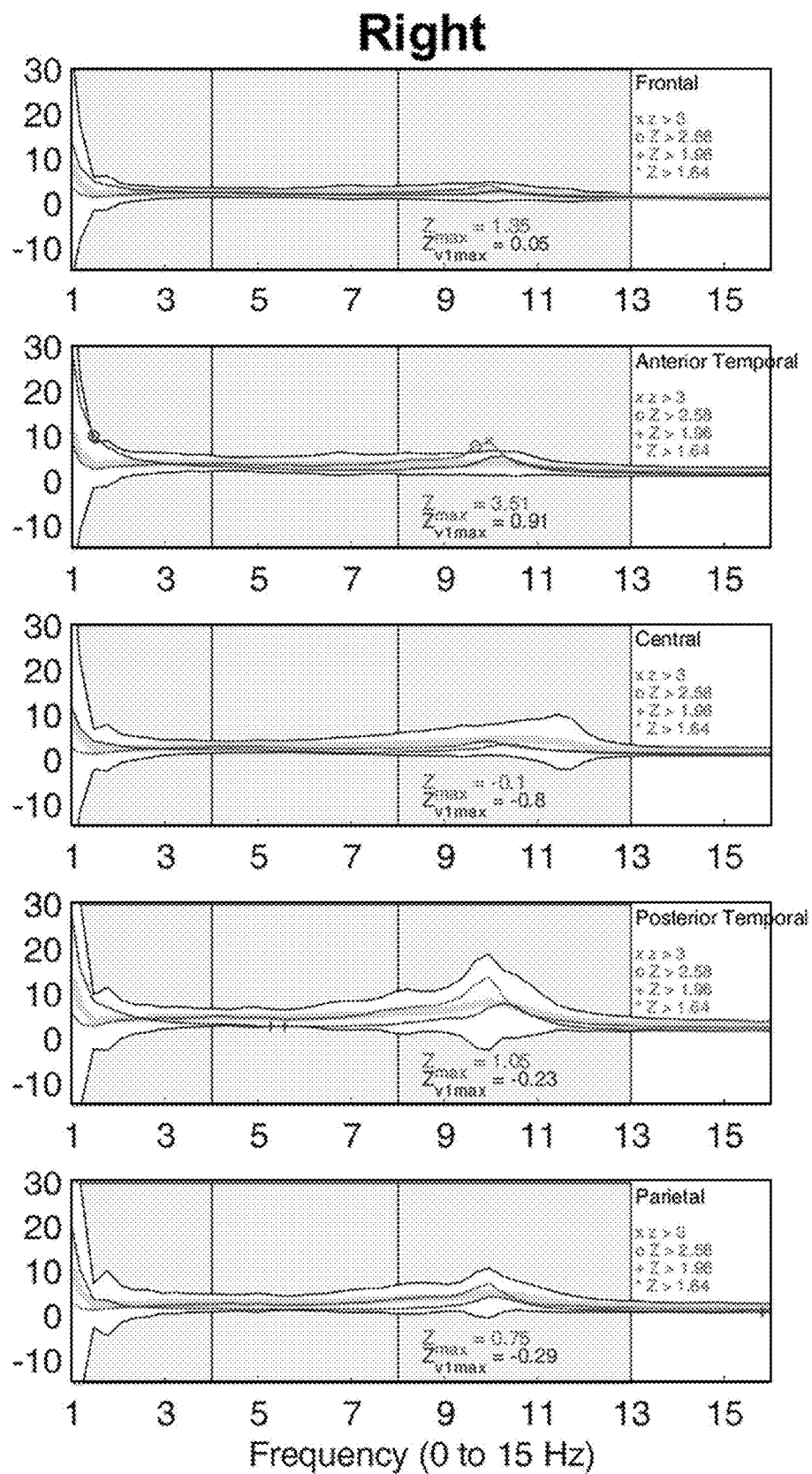

FIGS. 2A-2C show amplitude spectrum graphs from a 13-year-old male, with MEG obtained 13 days after concussion (bike accident) and at ~4 months following the concussion. Reported symptoms at initial assessment included confusion, fear, 'felt in a fog' and amnesia of events immediately prior to the injury. The solid black arrows indicate abnormally increased alpha activity at the acute/subacute exam. The black dashed arrow indicates abnormally increased delta activity.

Figure 3A:
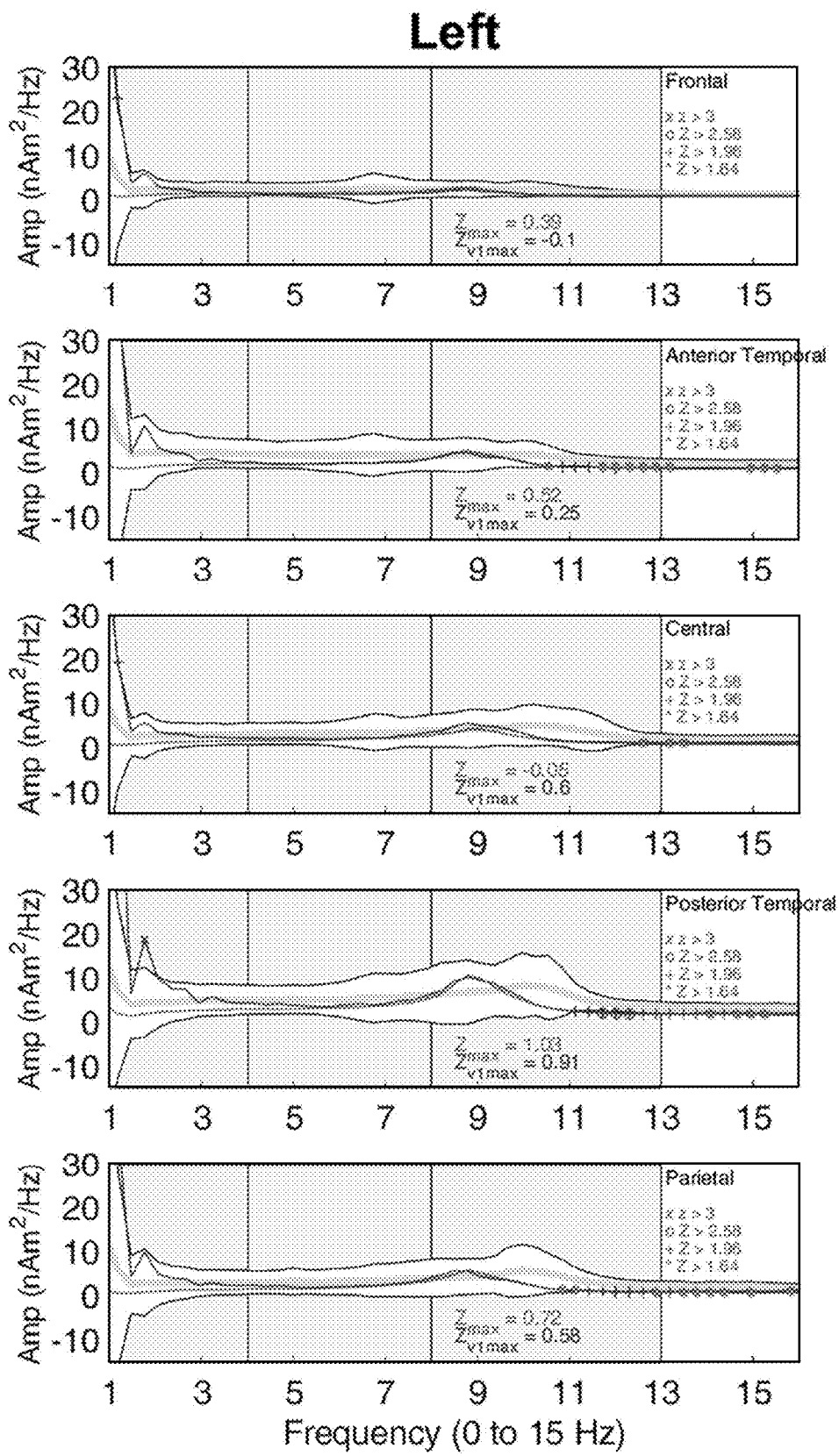
Figure 3B:
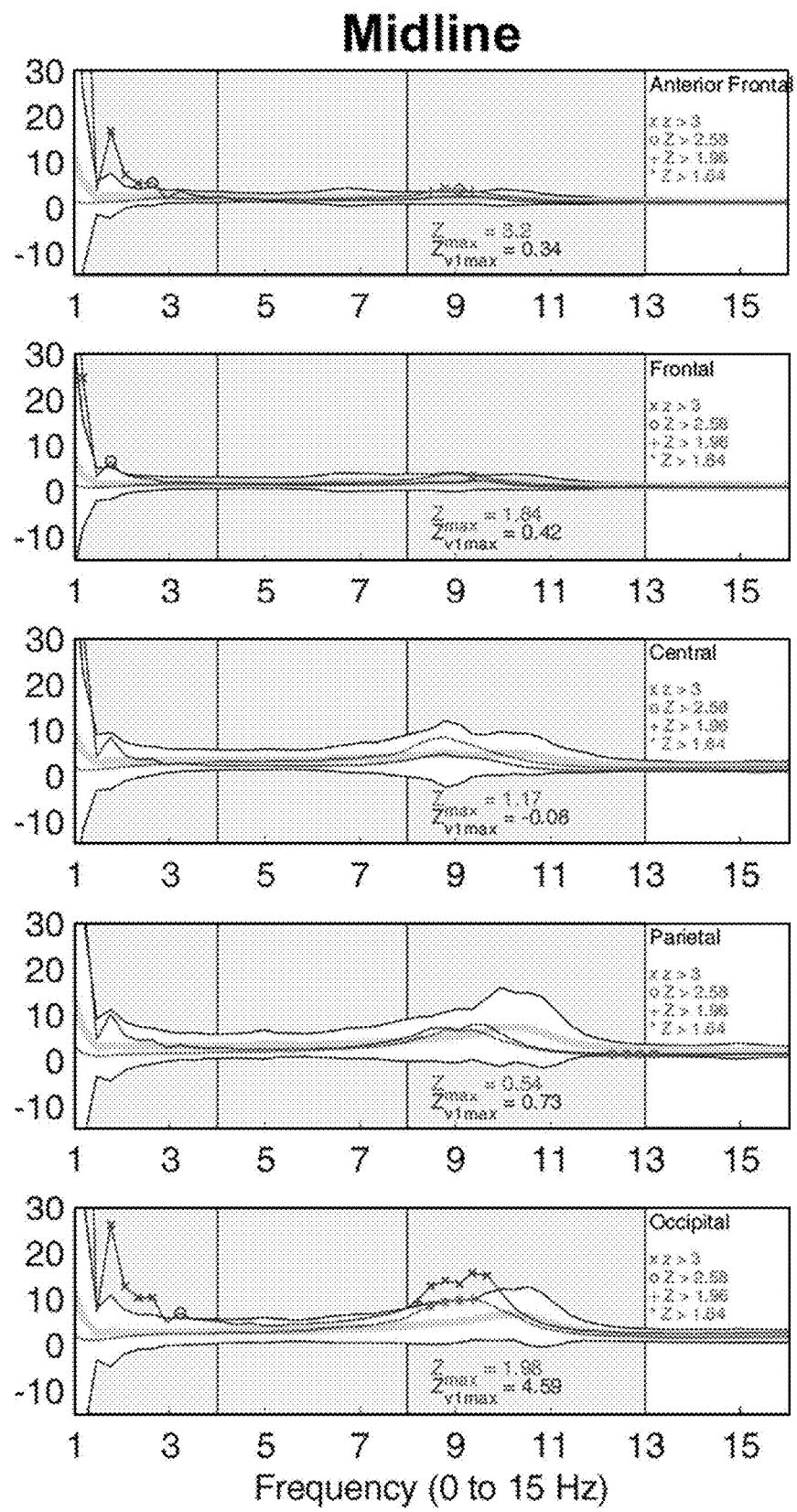
Figure 3C:
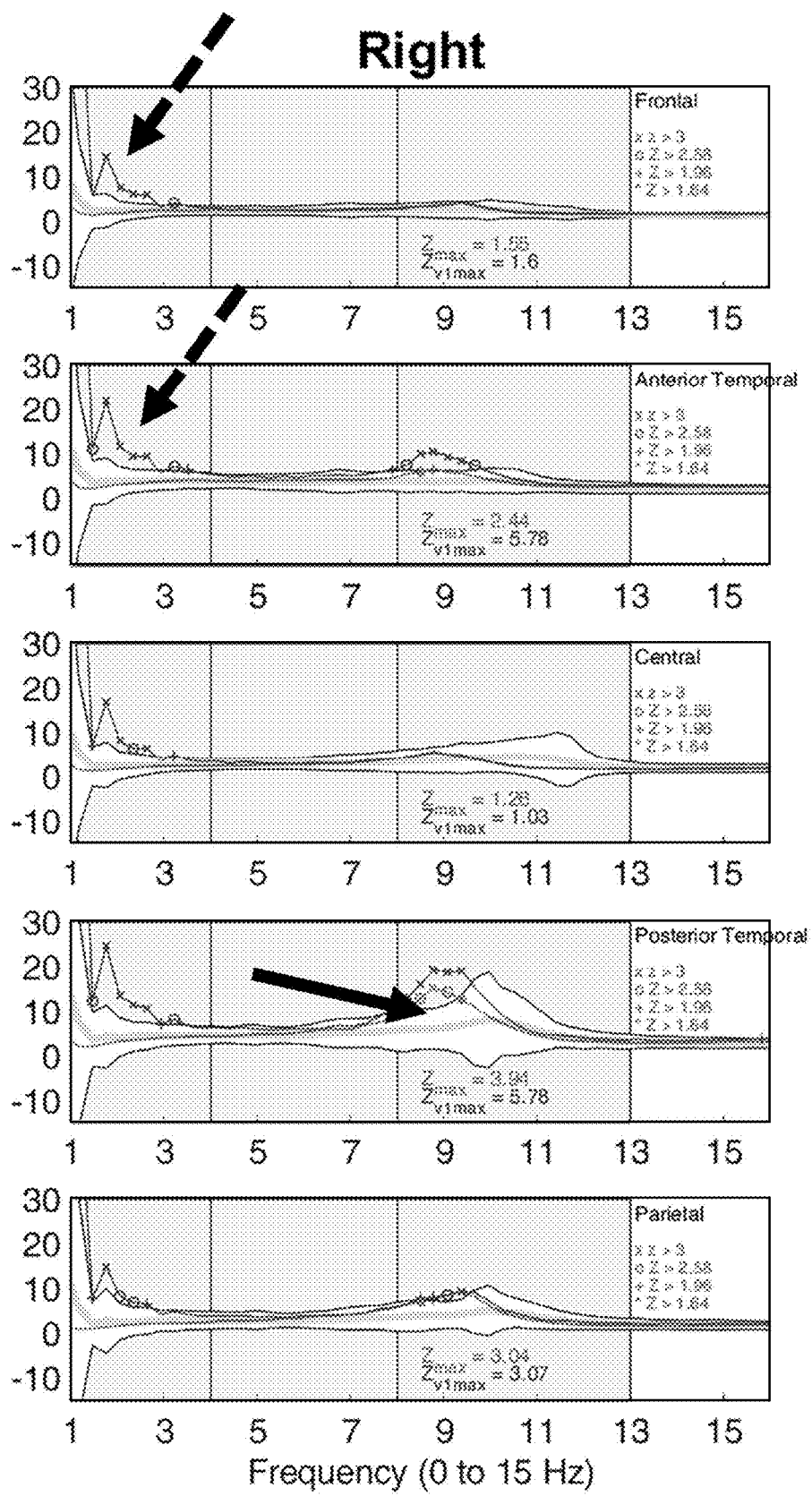

FIGS. 3A-3C shows amplitude spectrum from a 16-year-old male with MEG obtained 11 days after concussion and at ~4 months following the concussion (bike accident). Reported symptoms at initial assessment included confusion, sleep changes, fatigue, and amnesia of events immediately prior to the injury. The solid black arrows indicate abnormally increased alpha activity at the acute/subacute exam. The black dashed arrow indicates abnormally increased delta activity. Of note, in this patient alpha activity continued to be elevated at the ~4-month exam. This patient, however, had another head injury in-between the 12-day and ~4-month exams, with the continued observation of elevated alpha again providing evidence of an acute head injury.

Figure 4A:
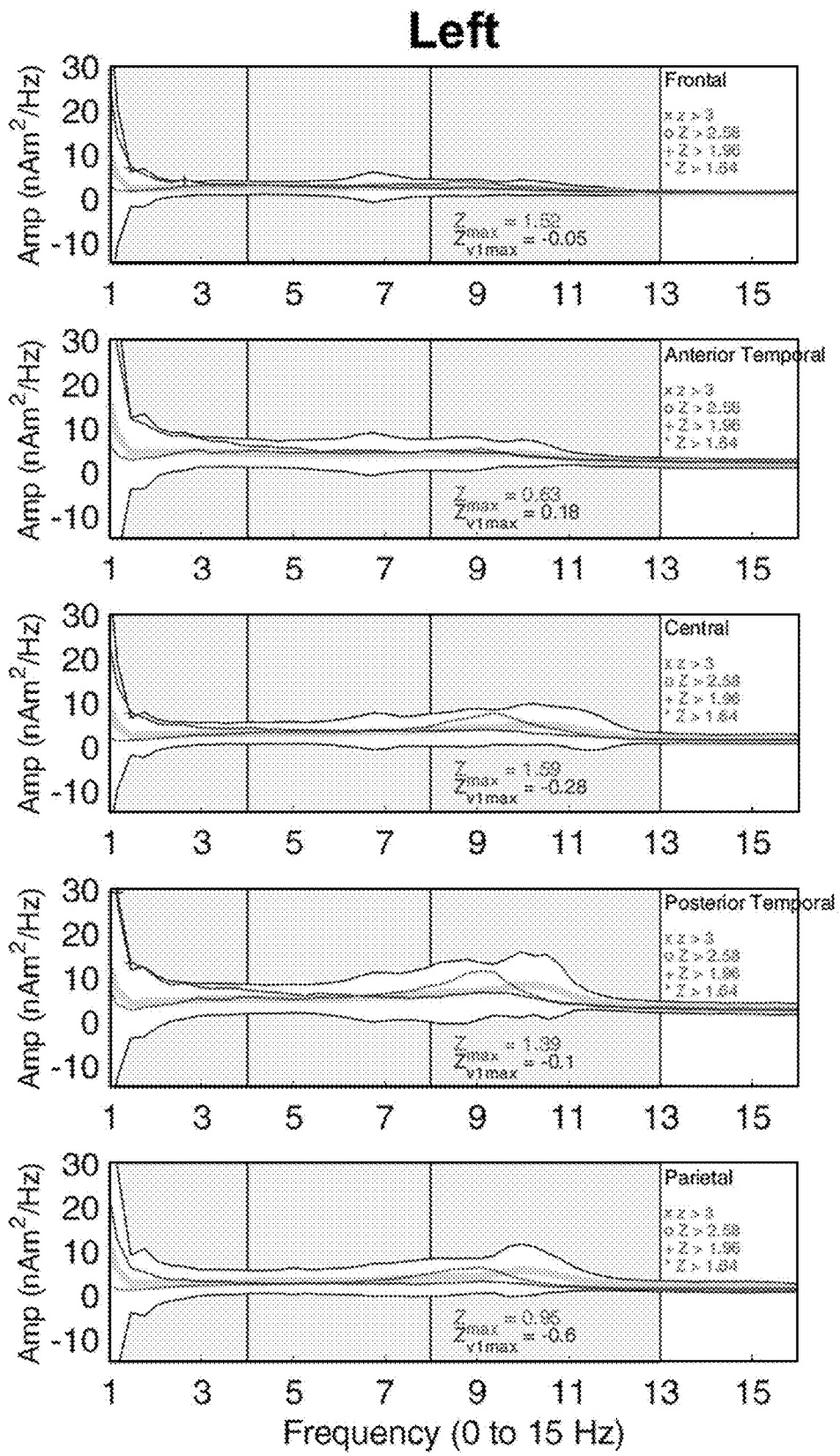
Figure 4B:
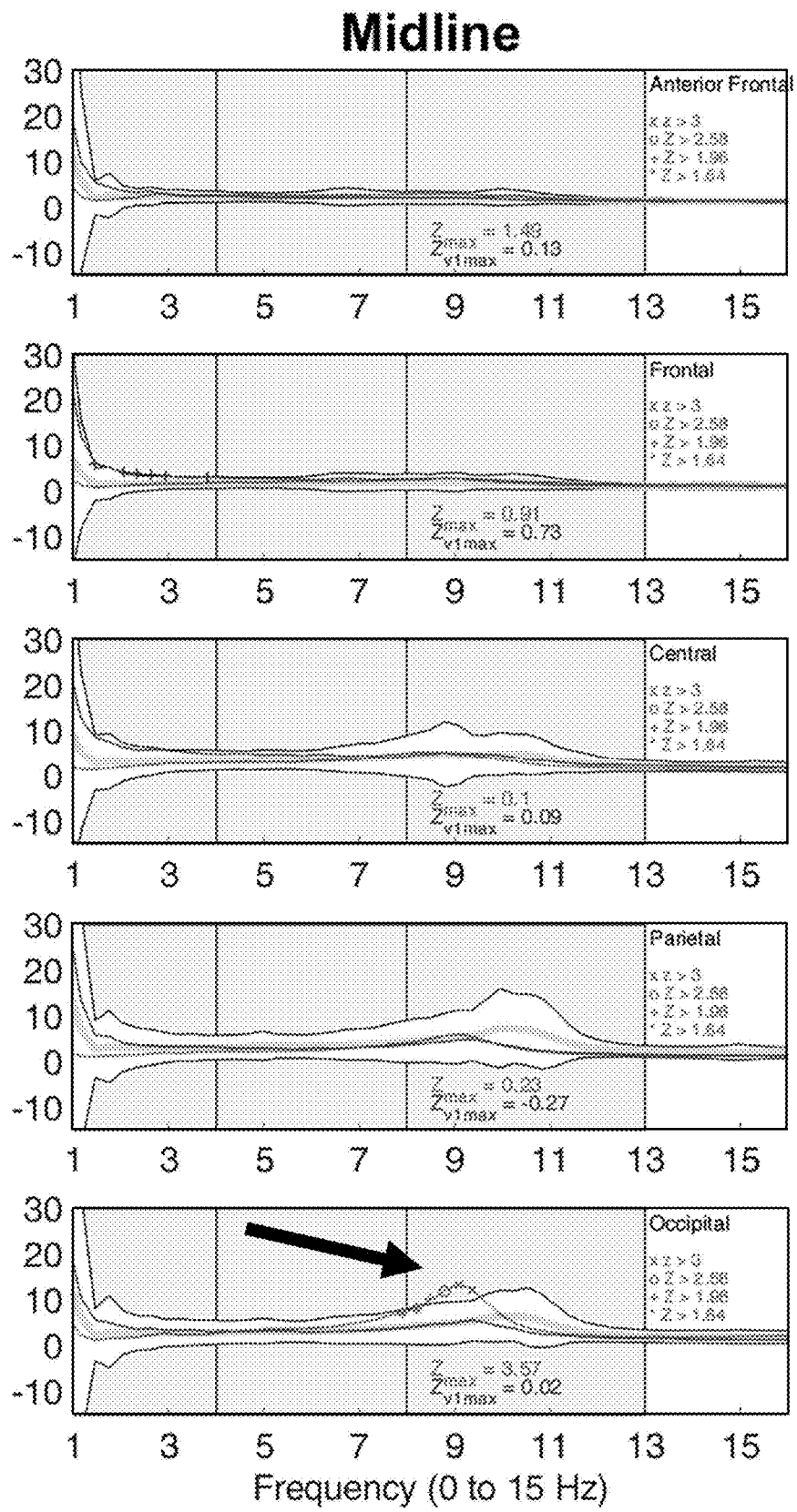
Figure 4C:
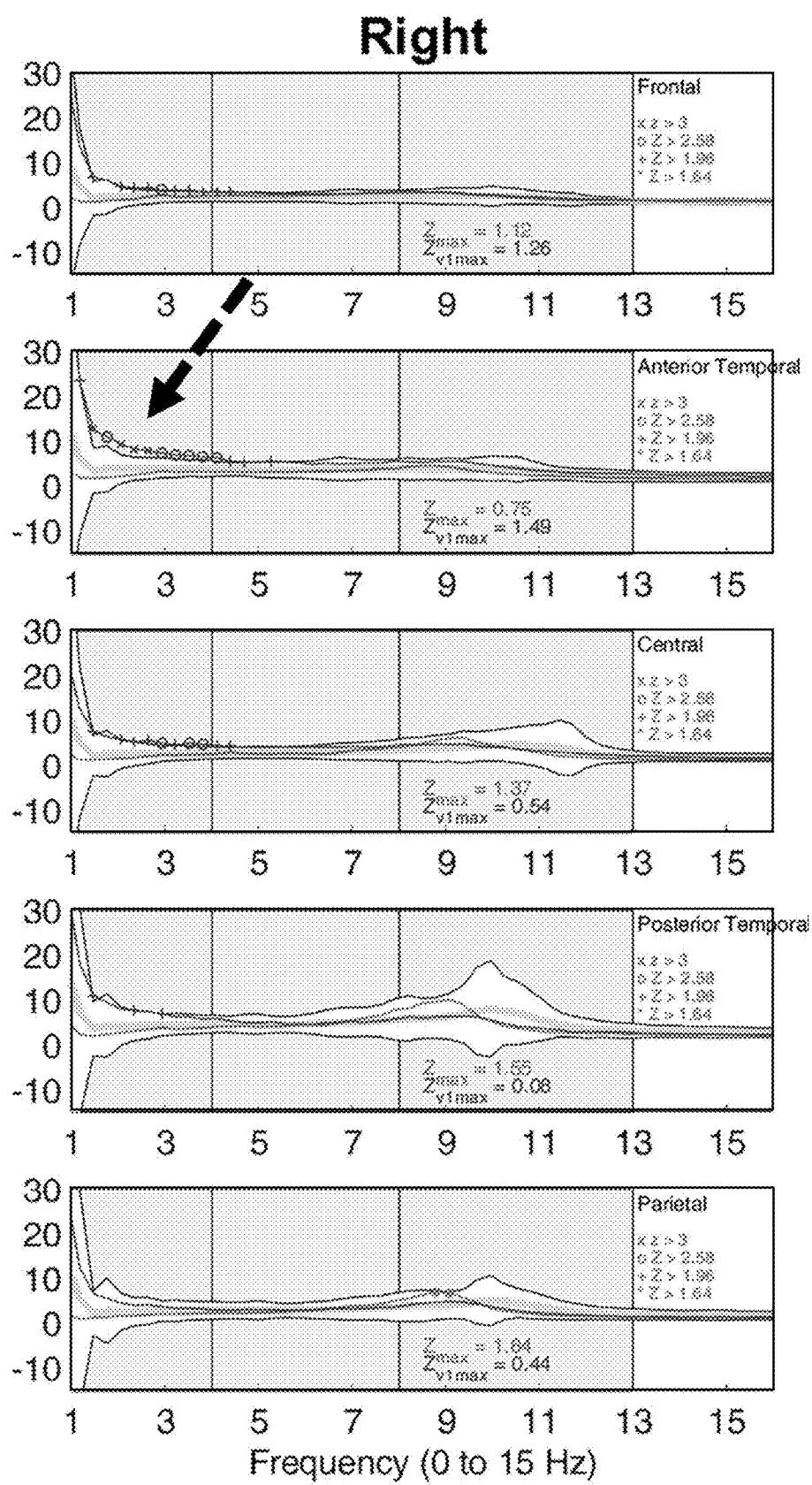

FIGS. 4A-4C shows amplitude spectrum from a 13-year-old male with MEG obtained 12 days after concussion and at a ~4 months following the concussion (hit head while swimming). Reported symptoms at initial assessment included headache, dizziness, nausea, and sleeping more than usual. The solid black arrow indicates abnormally increased alpha activity at the acute/subacute exam. The black dashed arrow indicates abnormally increased delta activity.

Figure 5A:
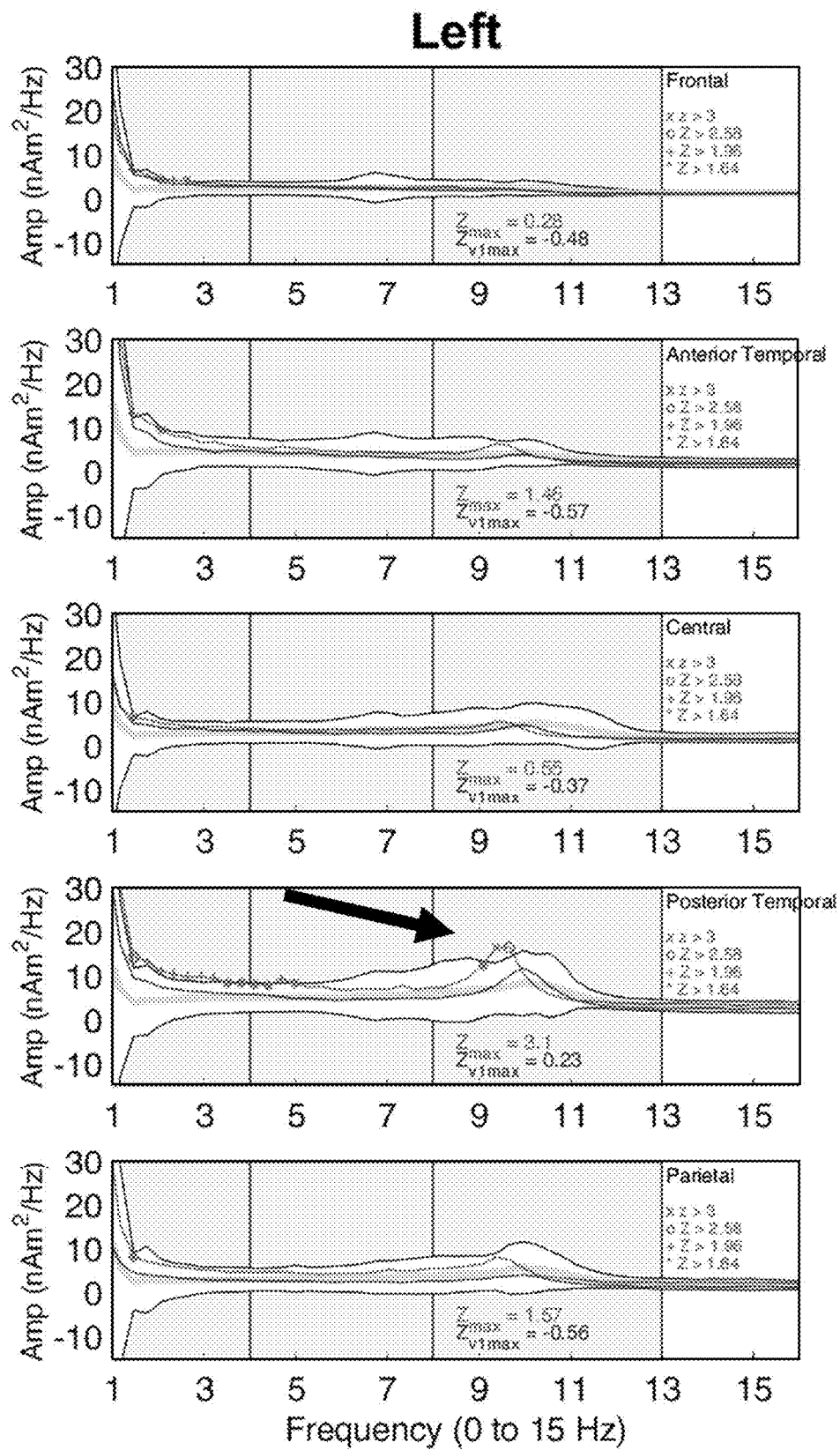
Figure 5B:
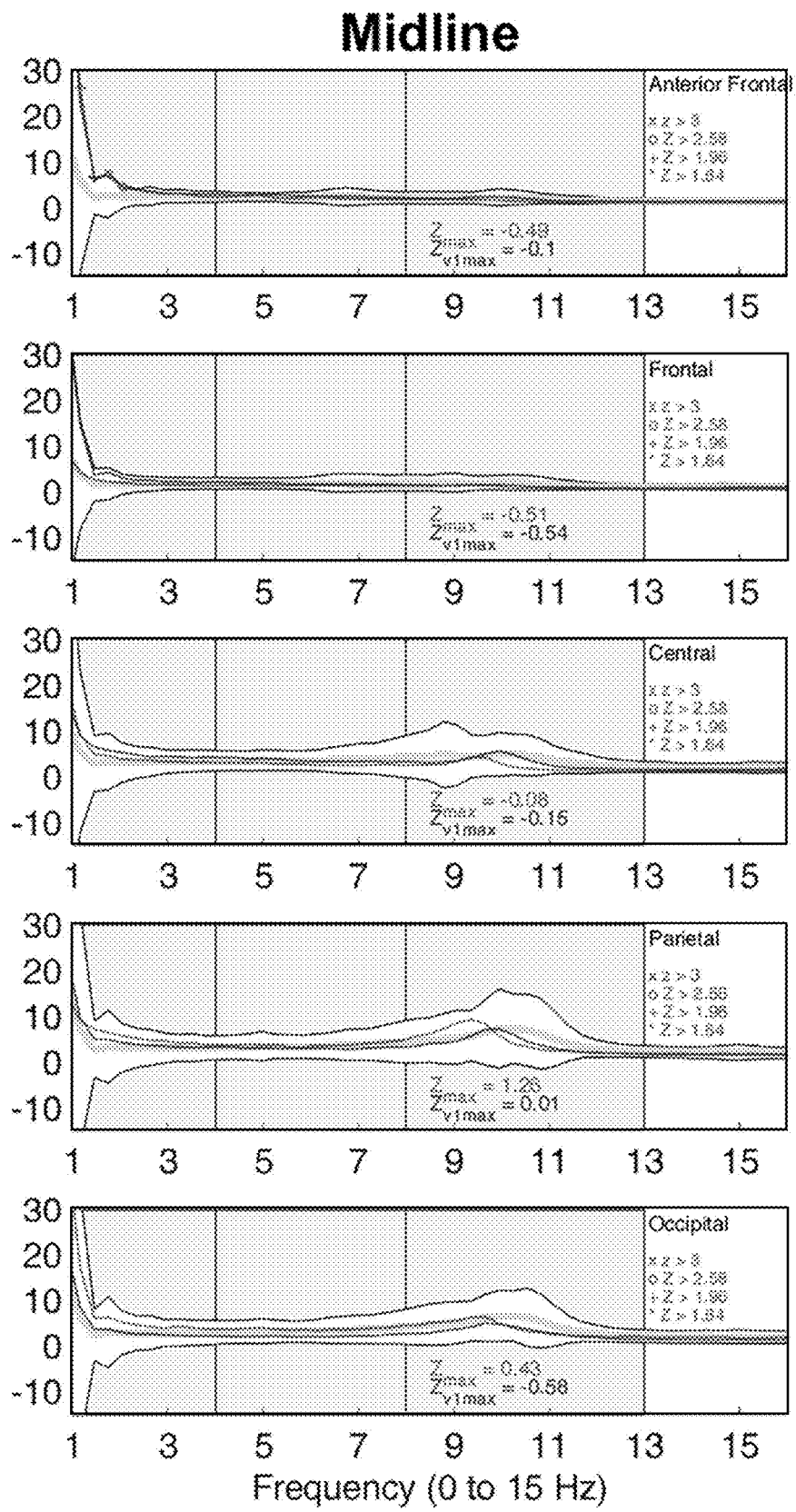
Figure 5C:
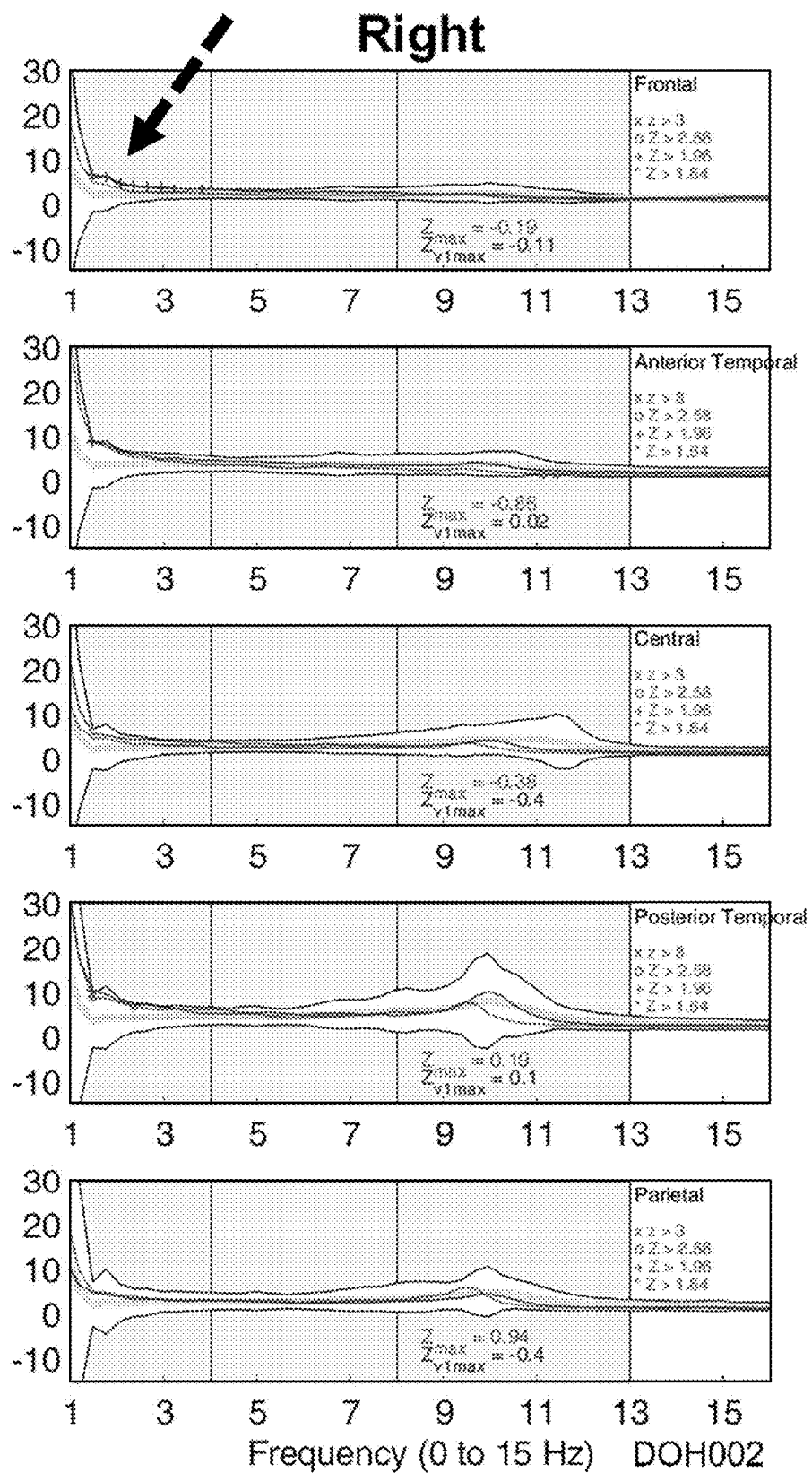

FIGS. 5A-5C shows amplitude spectrum from a 13-year-old-male with MEG obtained 5 days after concussion and at ~4 months following concussion (head hit during lacrosse game). Reported symptoms at initial assessment included headache, drowsiness, and sensitivity to light and noise. The solid black arrow indicates abnormally increased alpha activity at the acute/subacute exam. The black dashed arrow indicates abnormally increased delta activity.

Figure 6A:
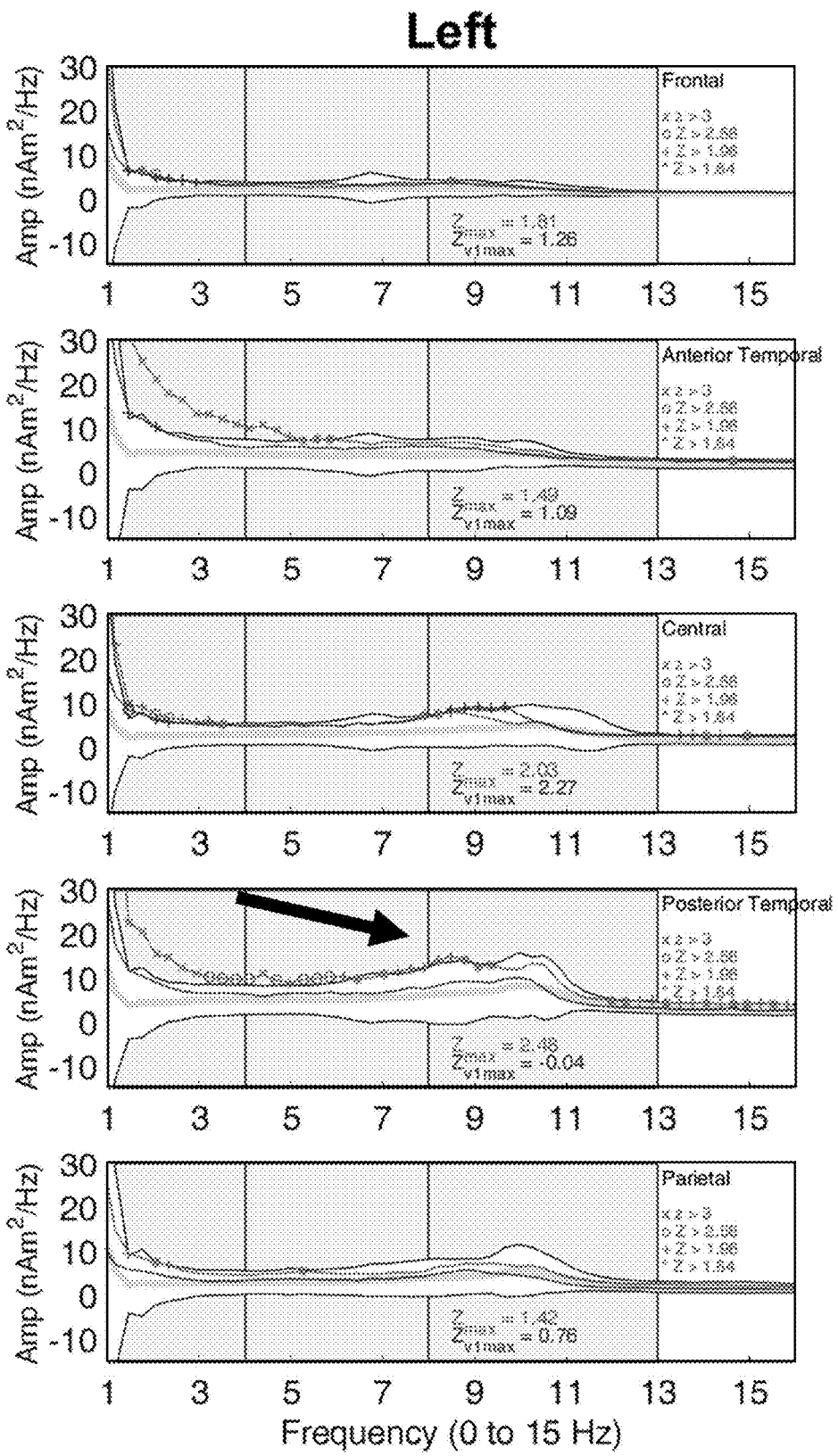
Figure 6B:
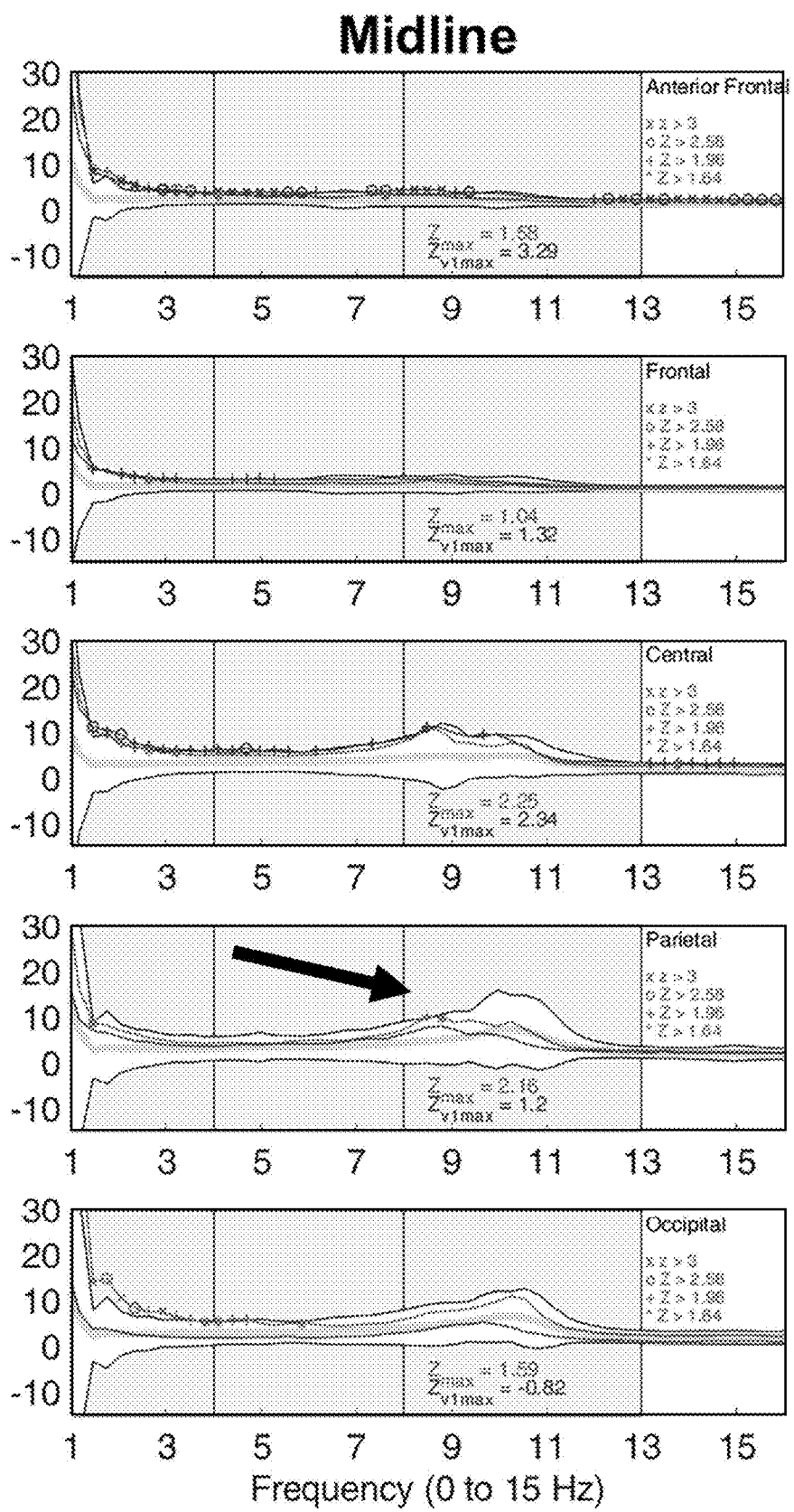
Figure 6C:
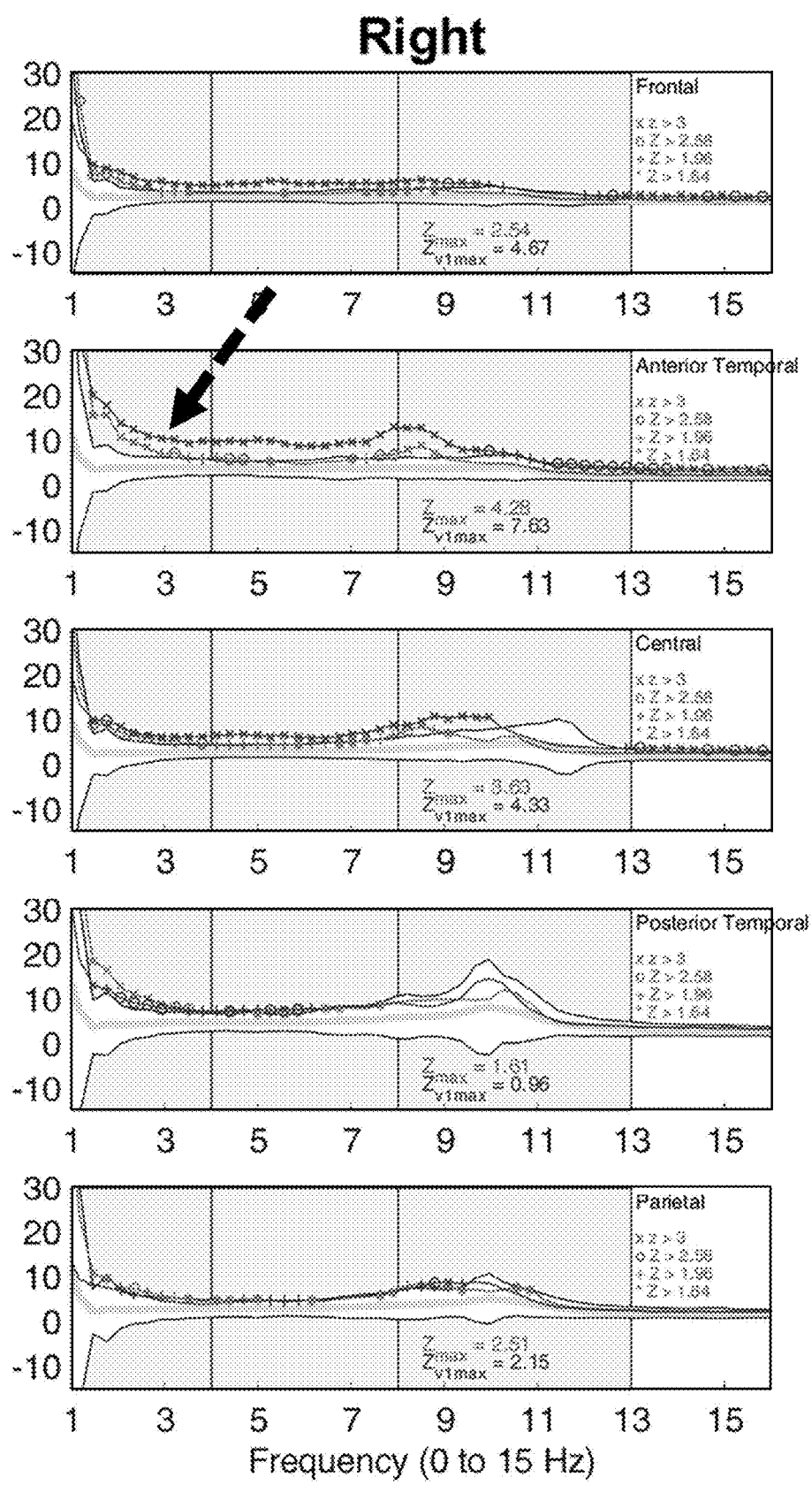

FIGS. 6A-6C show amplitude spectrum from an 11-year-old female with MEG obtained 7 days after concussion and at ~4 months following concussion (hit head during fall). Reported symptoms at initial assessment included dizziness, disorientation, headache, irritability, mood changes and some memory loss. The solid black arrows indicate abnormally increased alpha activity at the acute/subacute exam. The black dashed arrow indicates abnormally increased delta activity.

Figure 7A:
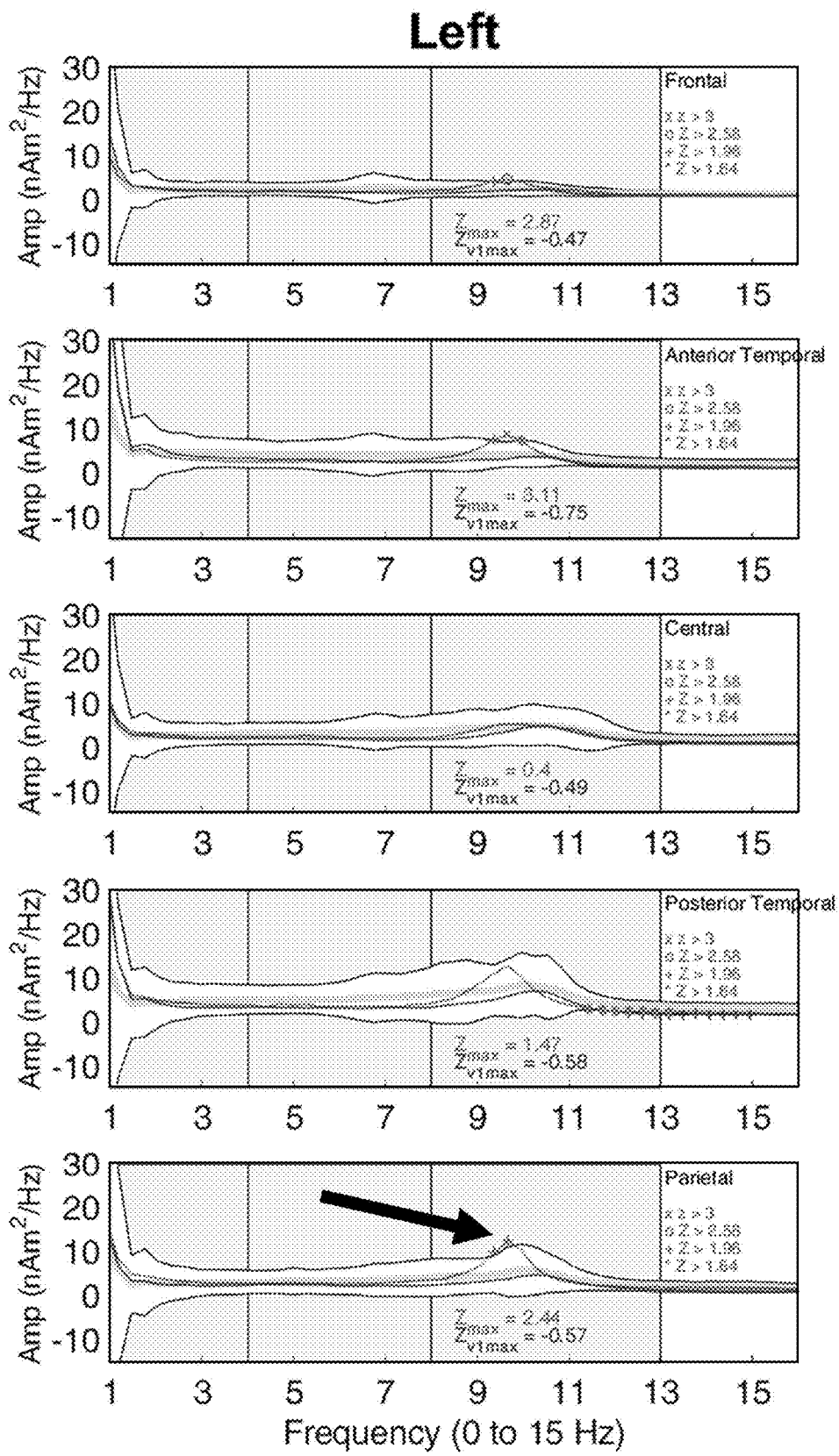
Figure 7B:
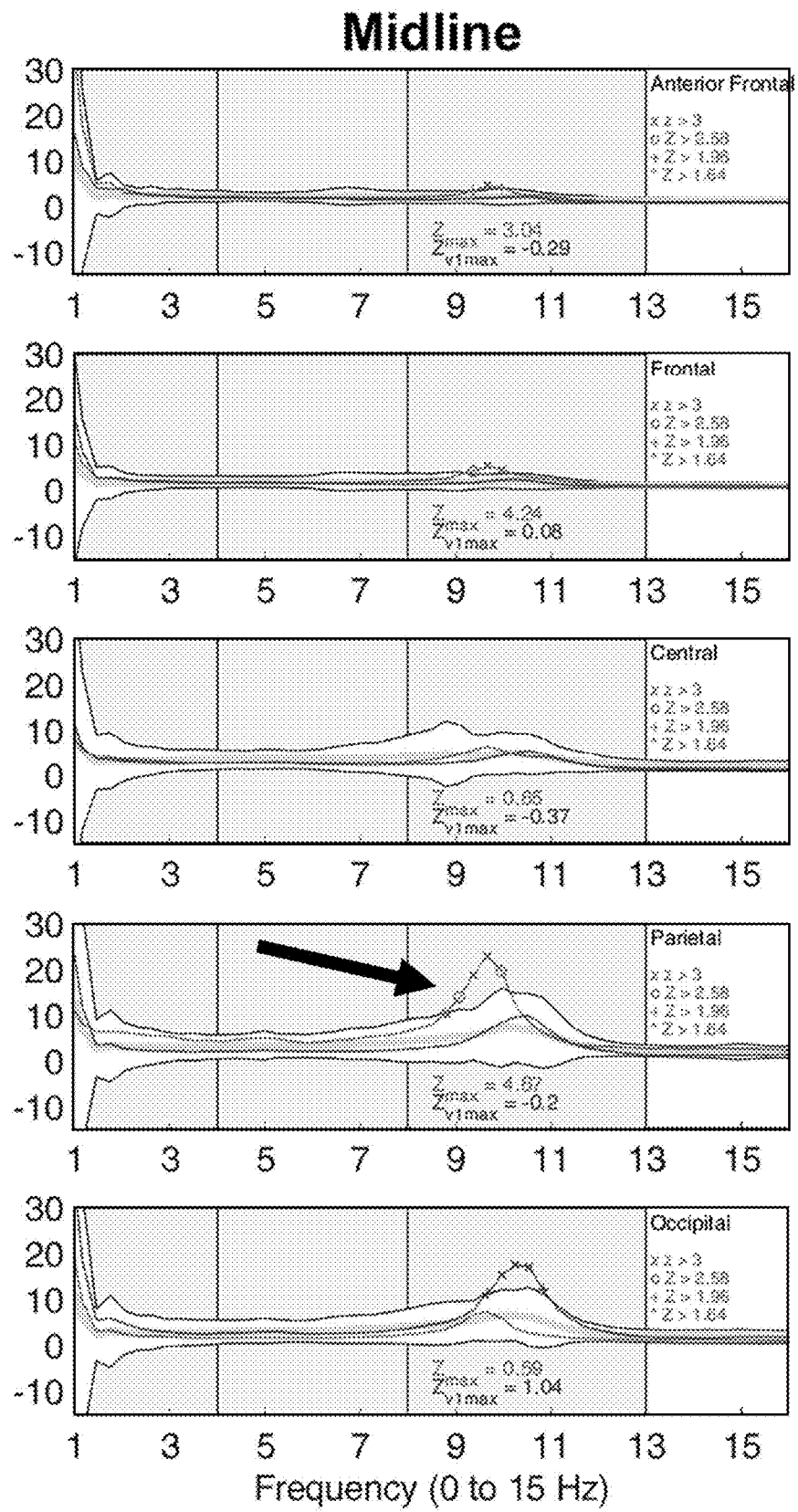
Figure 7C:
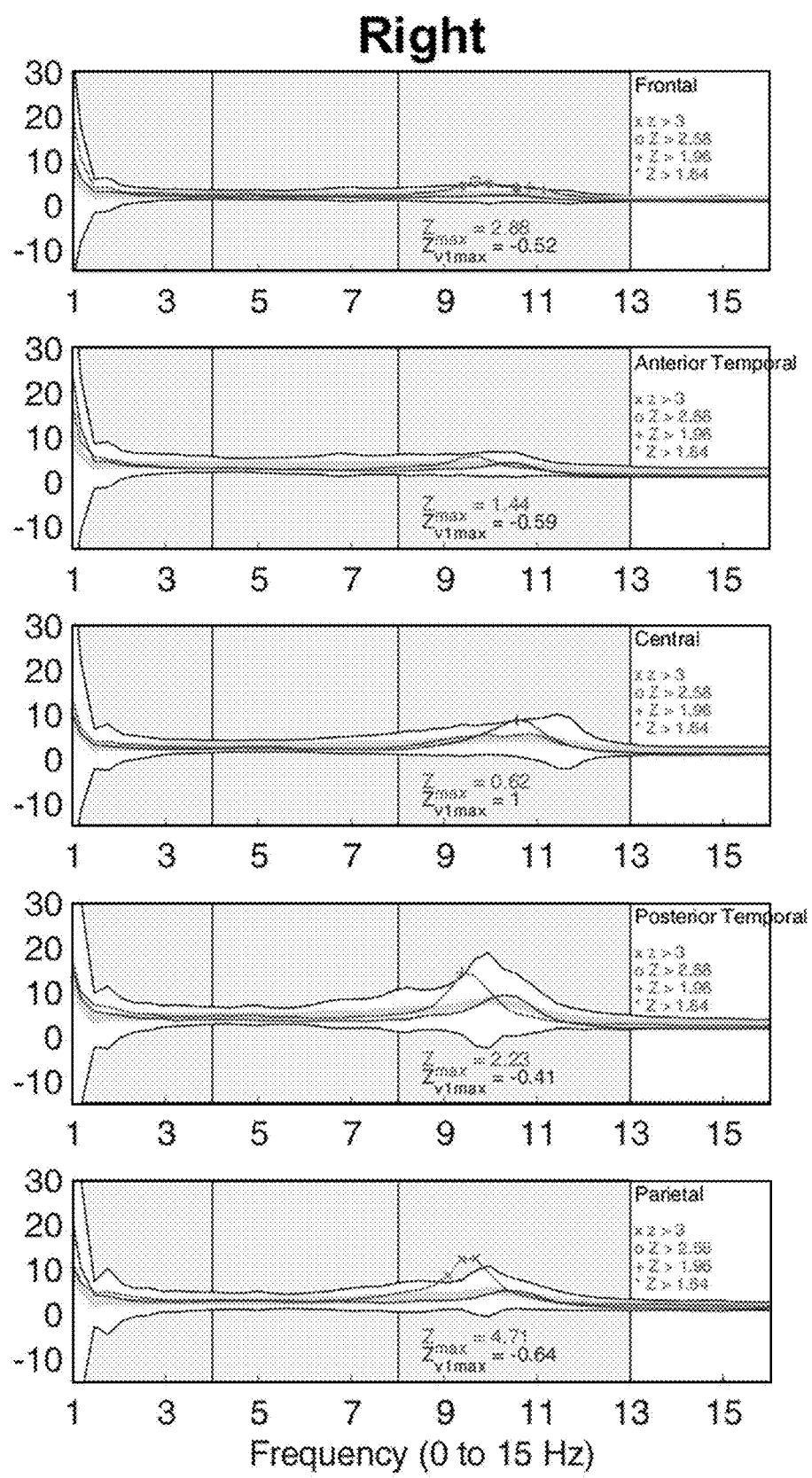

FIGS. 7A-7C show amplitude spectrum from a 16-year-old female with MEG obtained 7 days after concussion and at ~4 months following concussion (head hit during softball game). Reported symptoms at initial assessment included headache, fatigue/drowsiness, sensitivity to light, and feeling foggy. The solid black arrows indicate abnormally increased alpha activity at the acute/subacute exam.

Figure 8A:
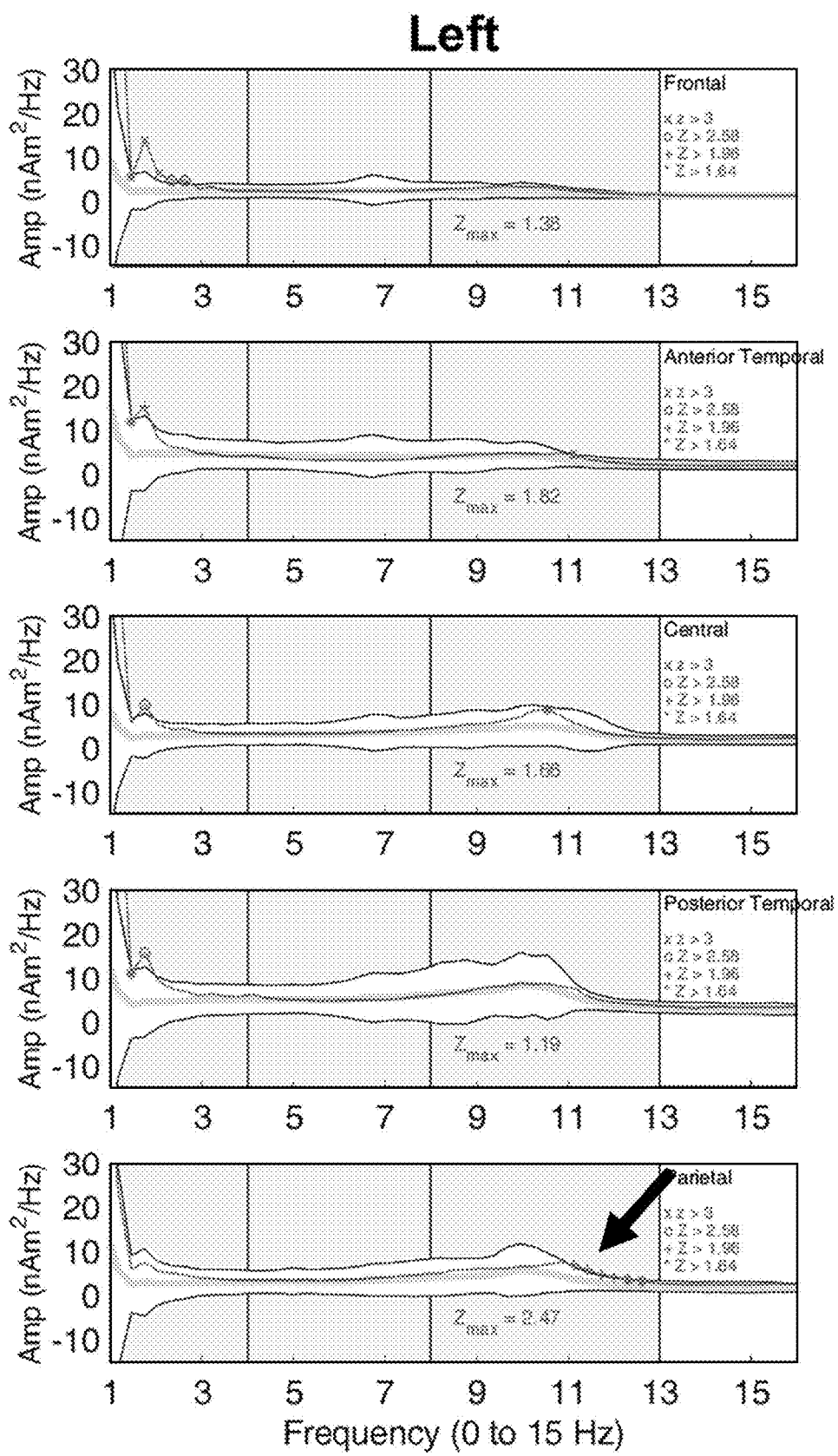
Figure 8B:
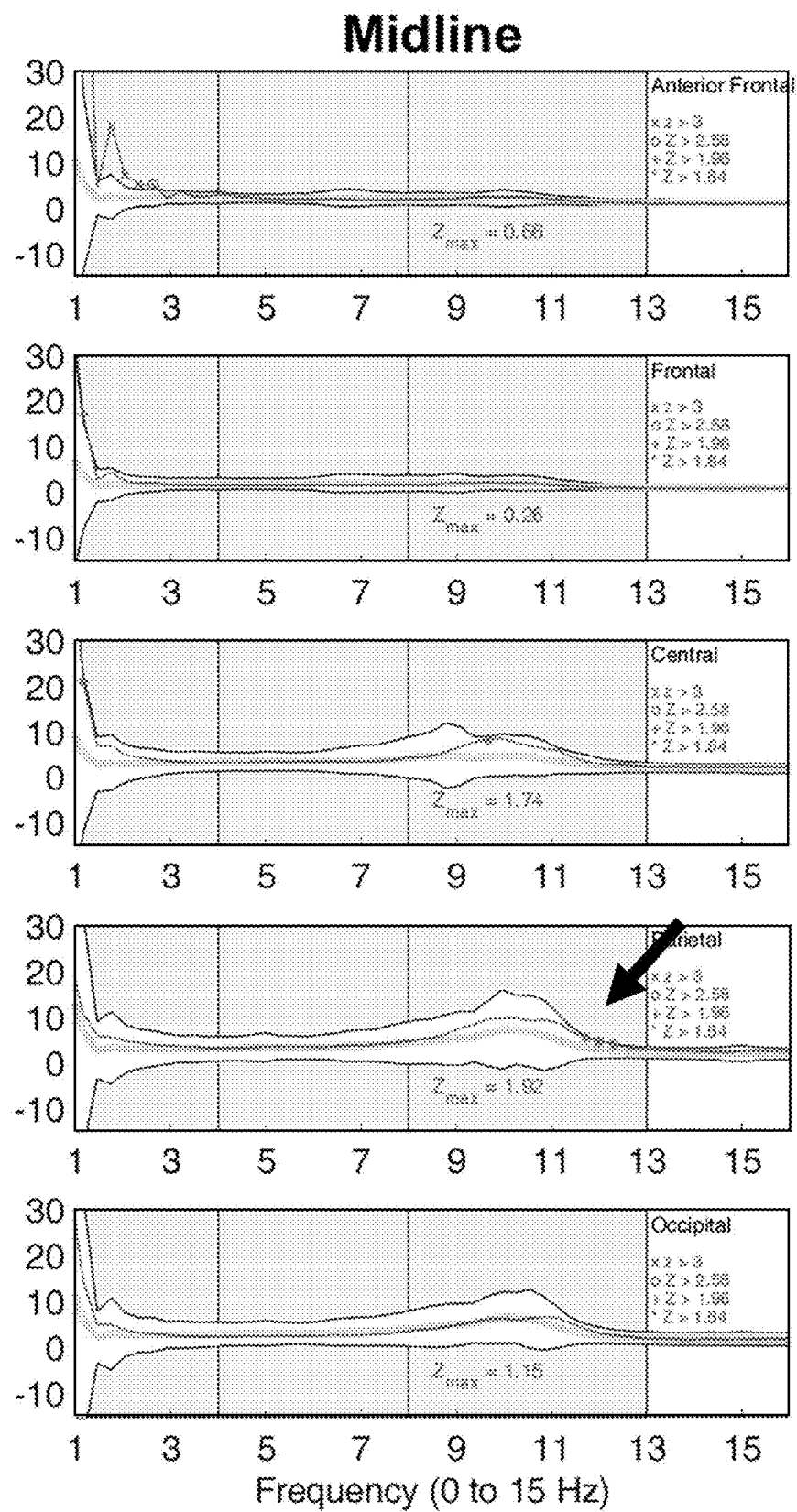
Figure 8C:
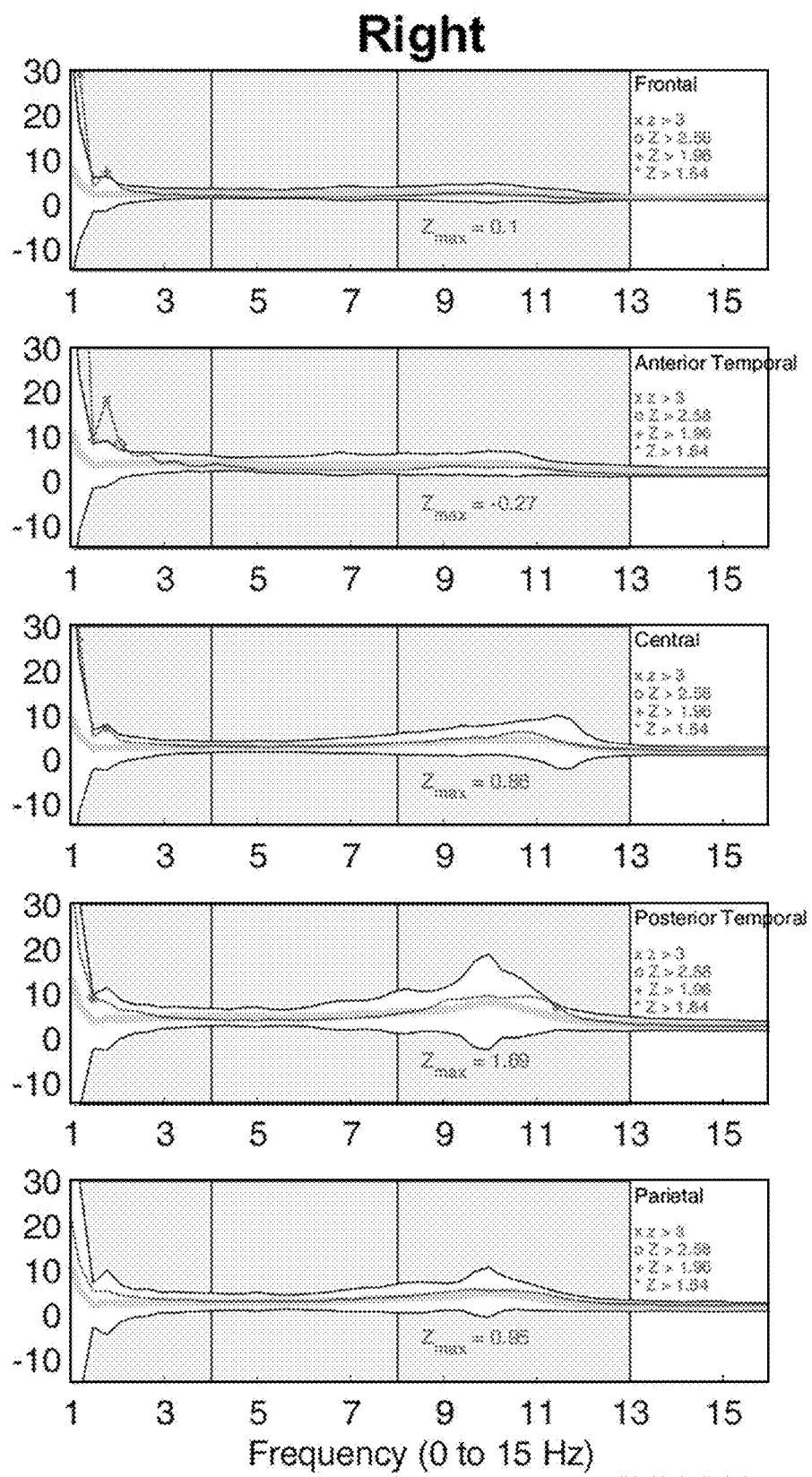

FIGS. 8A-8C show amplitude spectrum from a 17-year-old female with MEG obtained 4 days after concussion (hit head on trampoline). Follow-up exam not complete. Reported symptoms at initial assessment included confusion, headache, light and noise sensitivity, and dizziness. The solid black arrows indicate abnormally increased alpha activity at the acute/subacute exam.

Figure 9A:
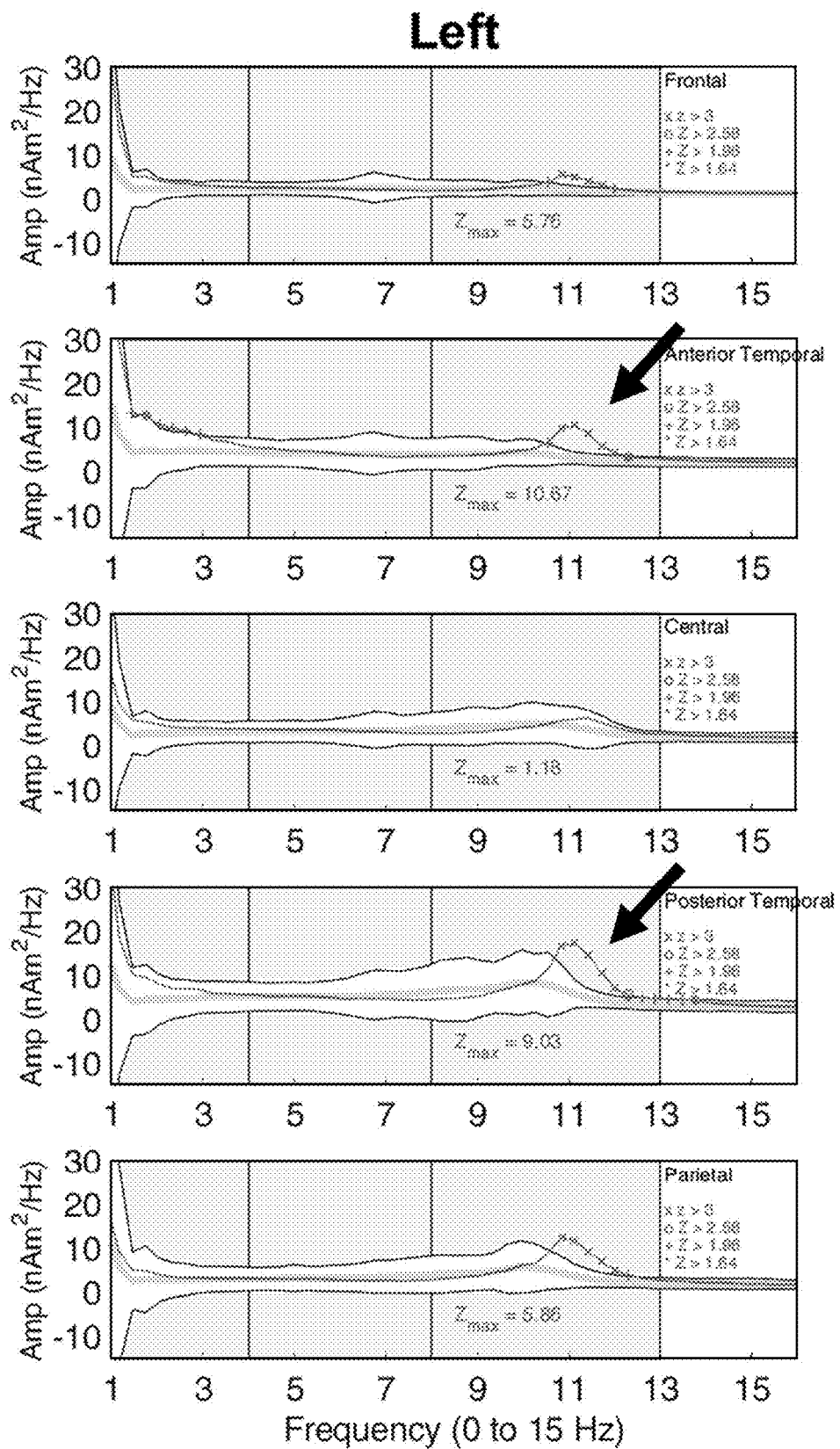
Figure 9B:
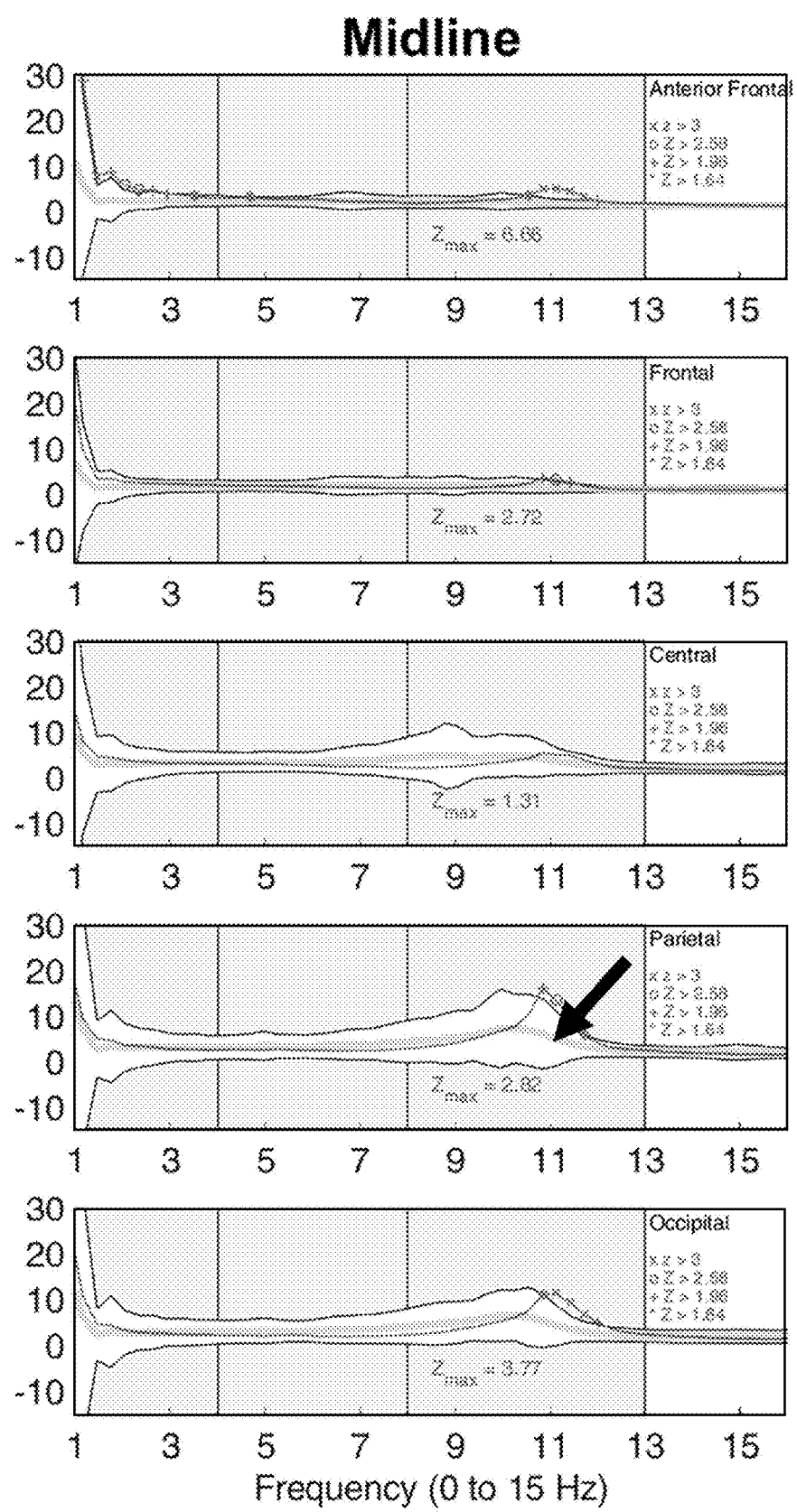
Figure 9C:
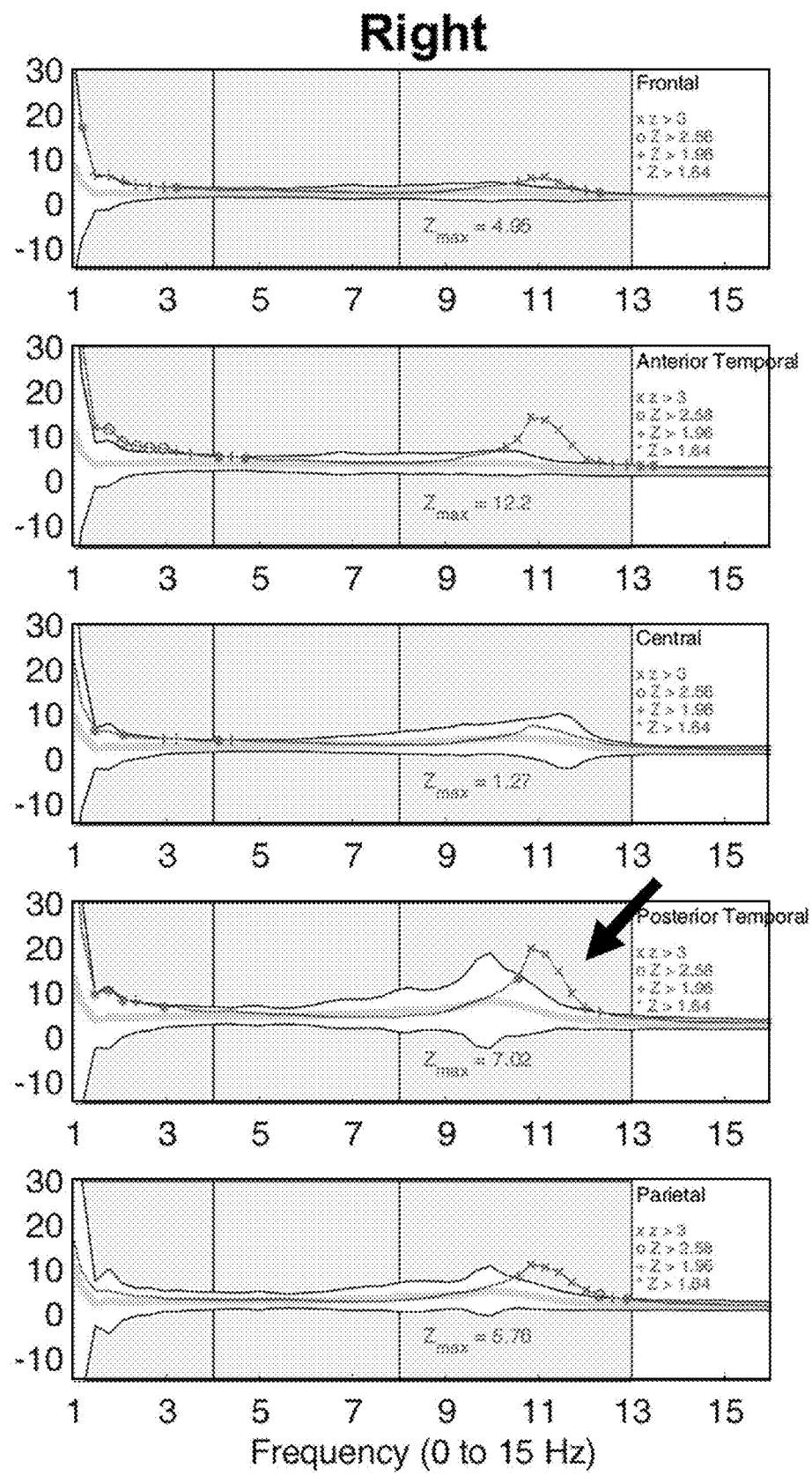

FIGS. 9A-9C show amplitude spectrum from a 14-year-old male with MEG obtained 19 days after concussion (head hit on trampoline). Follow-up exam not complete. Reported symptoms at initial assessment included headache, light sensitivity, nausea, dizziness, and fatigue. The solid black arrows indicate abnormally increased alpha activity at the acute/subacute exam.

Figure 10A:
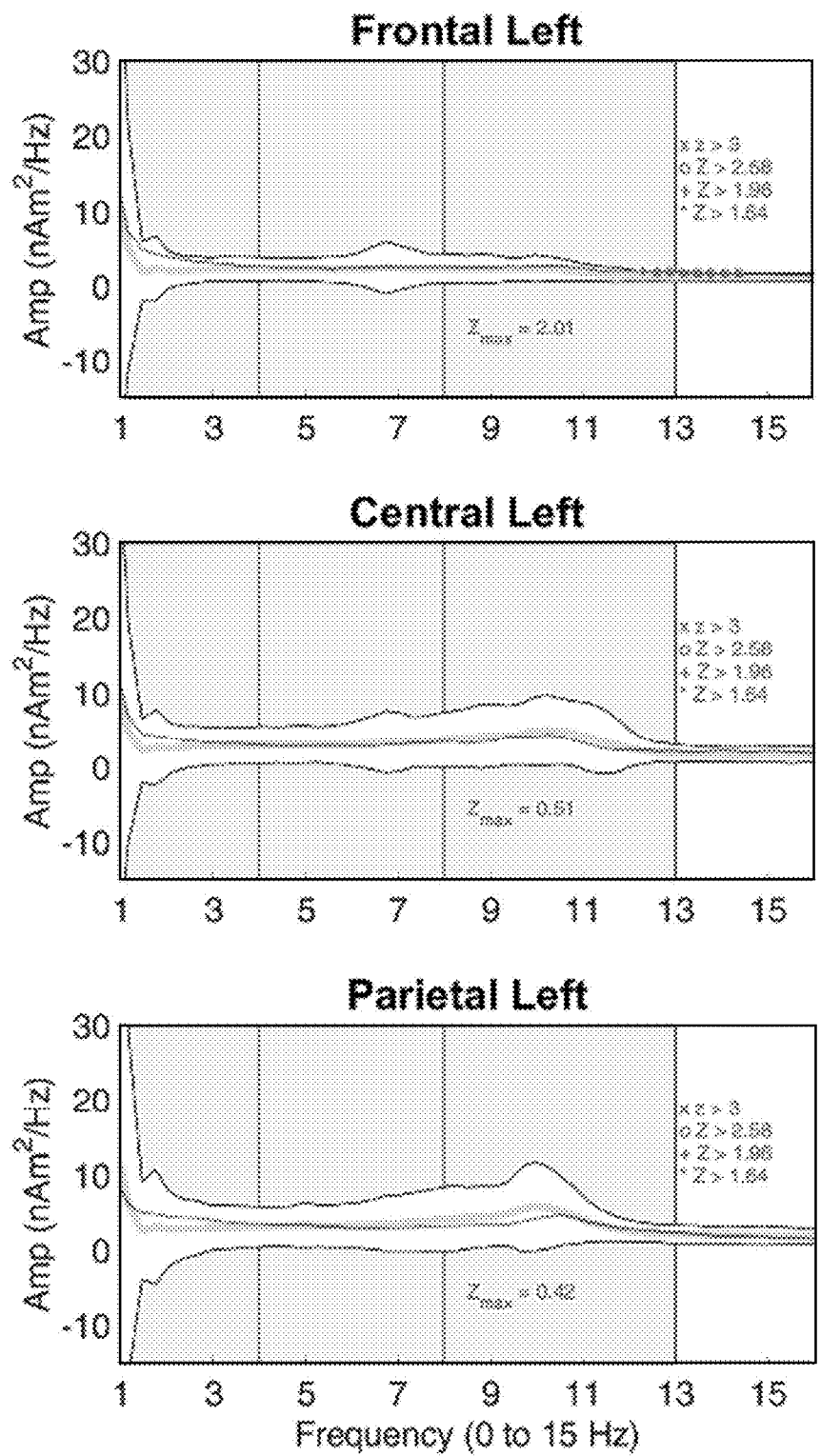
Figure 10B:
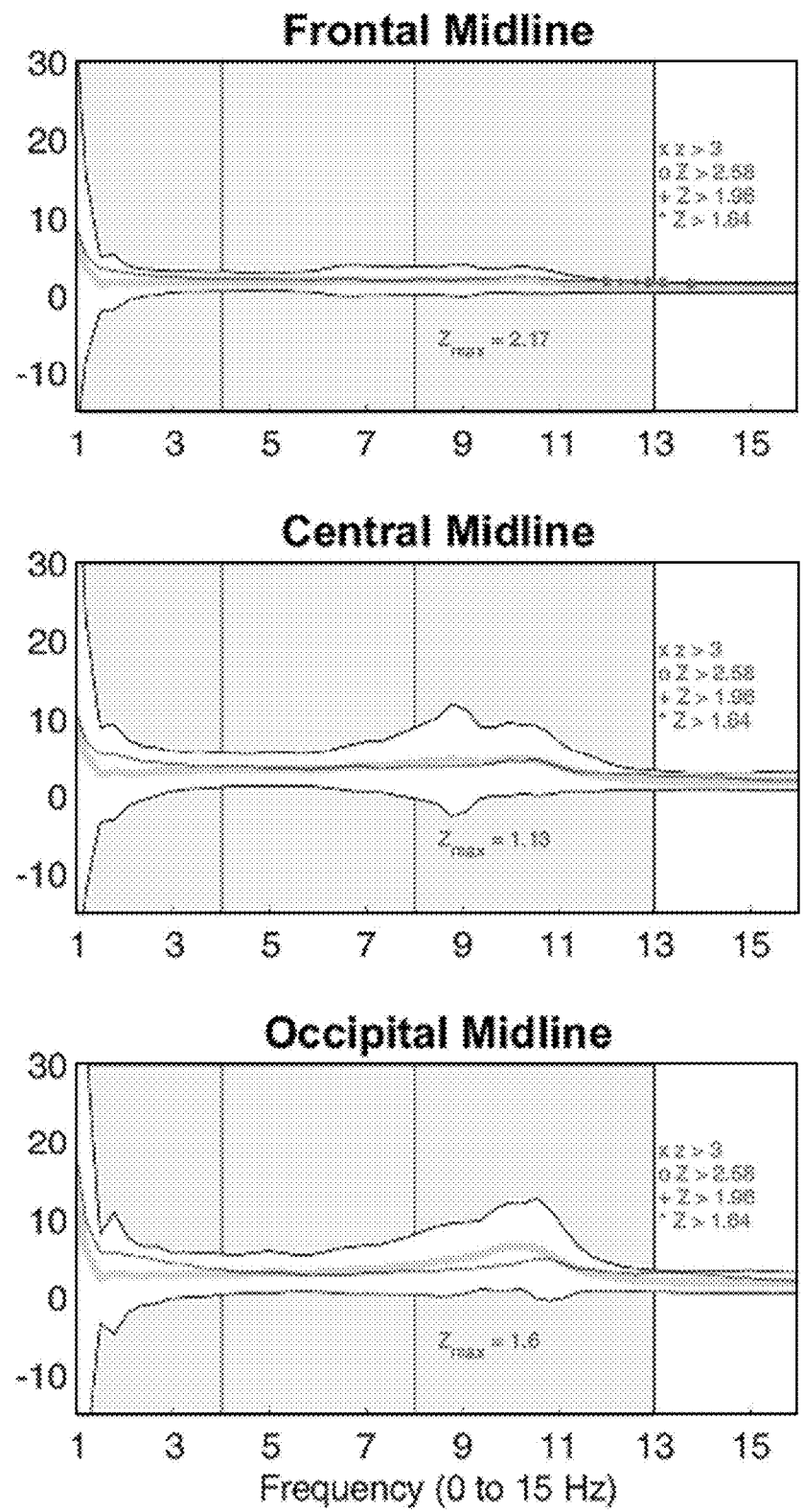
Figure 10C:
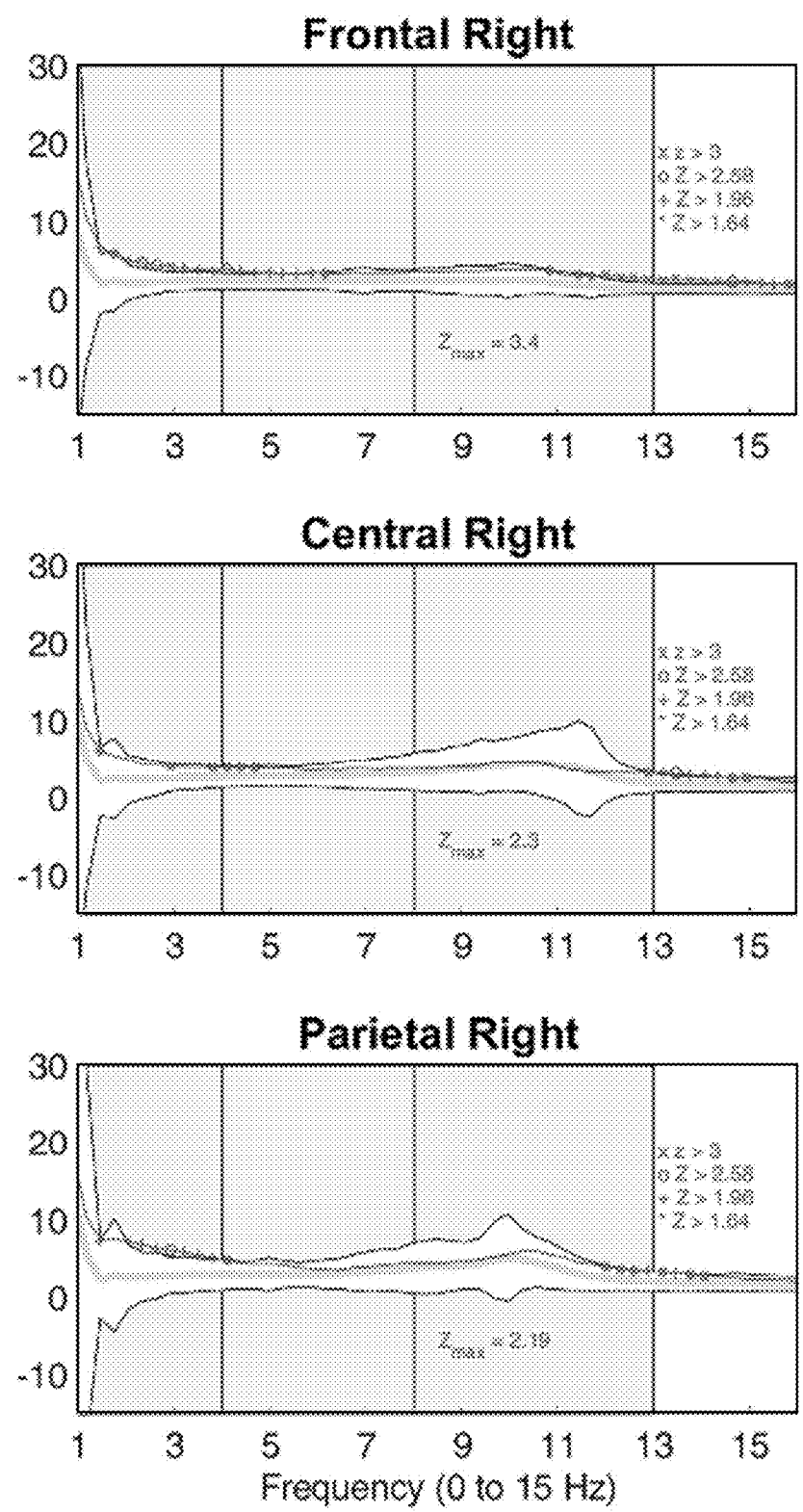
Figure 10D:
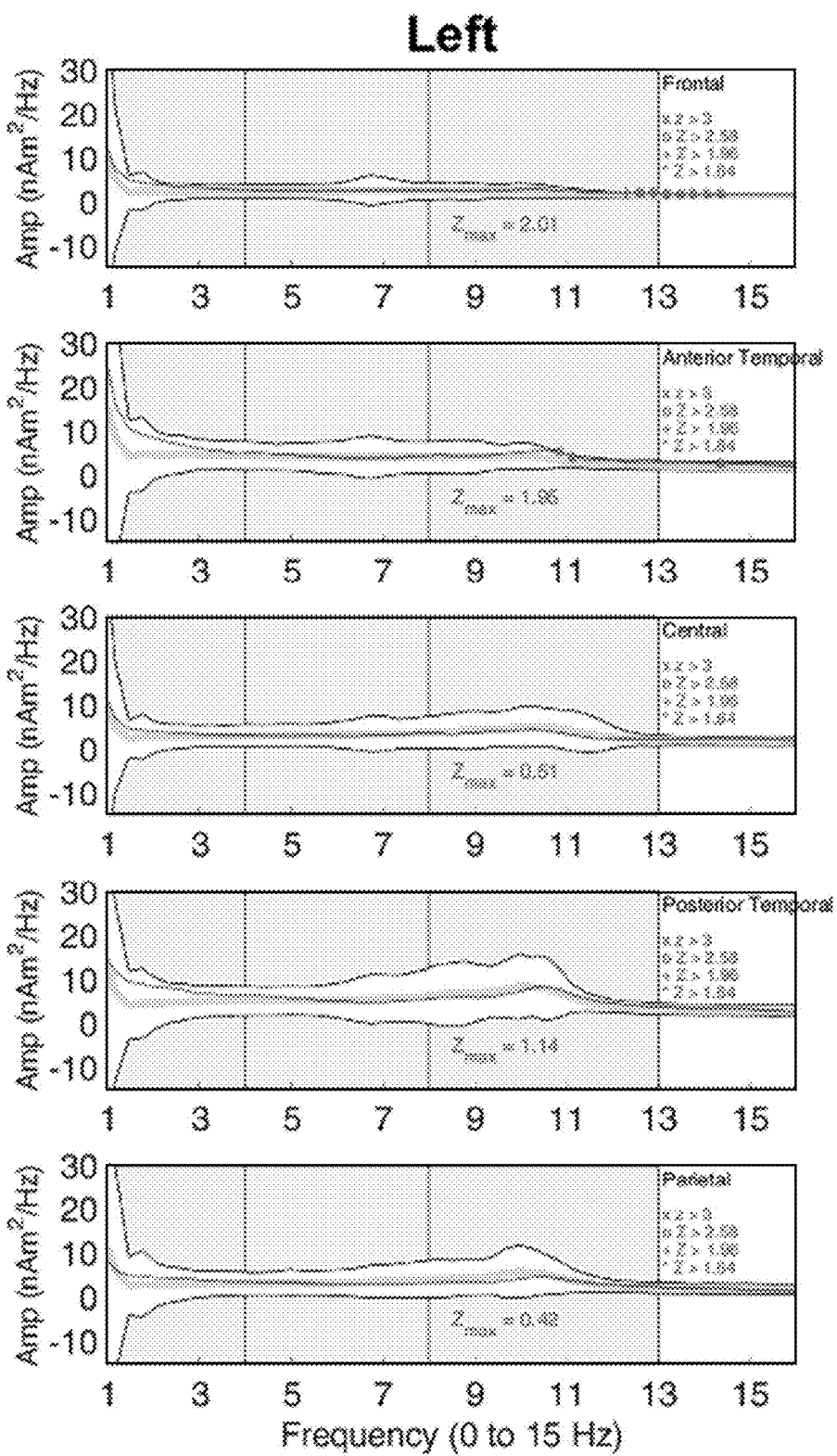
Figure 10E:
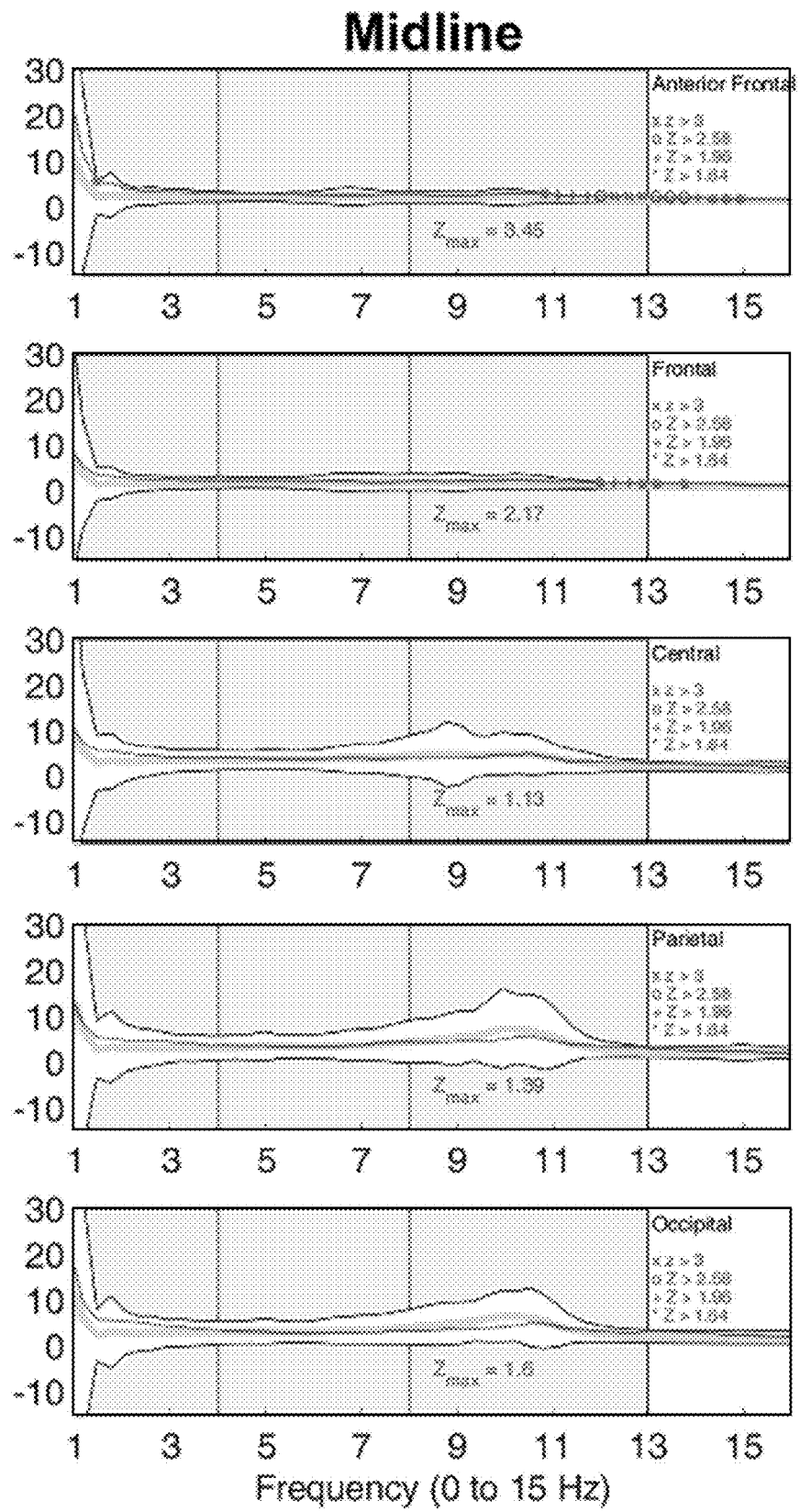
Figure 10F:
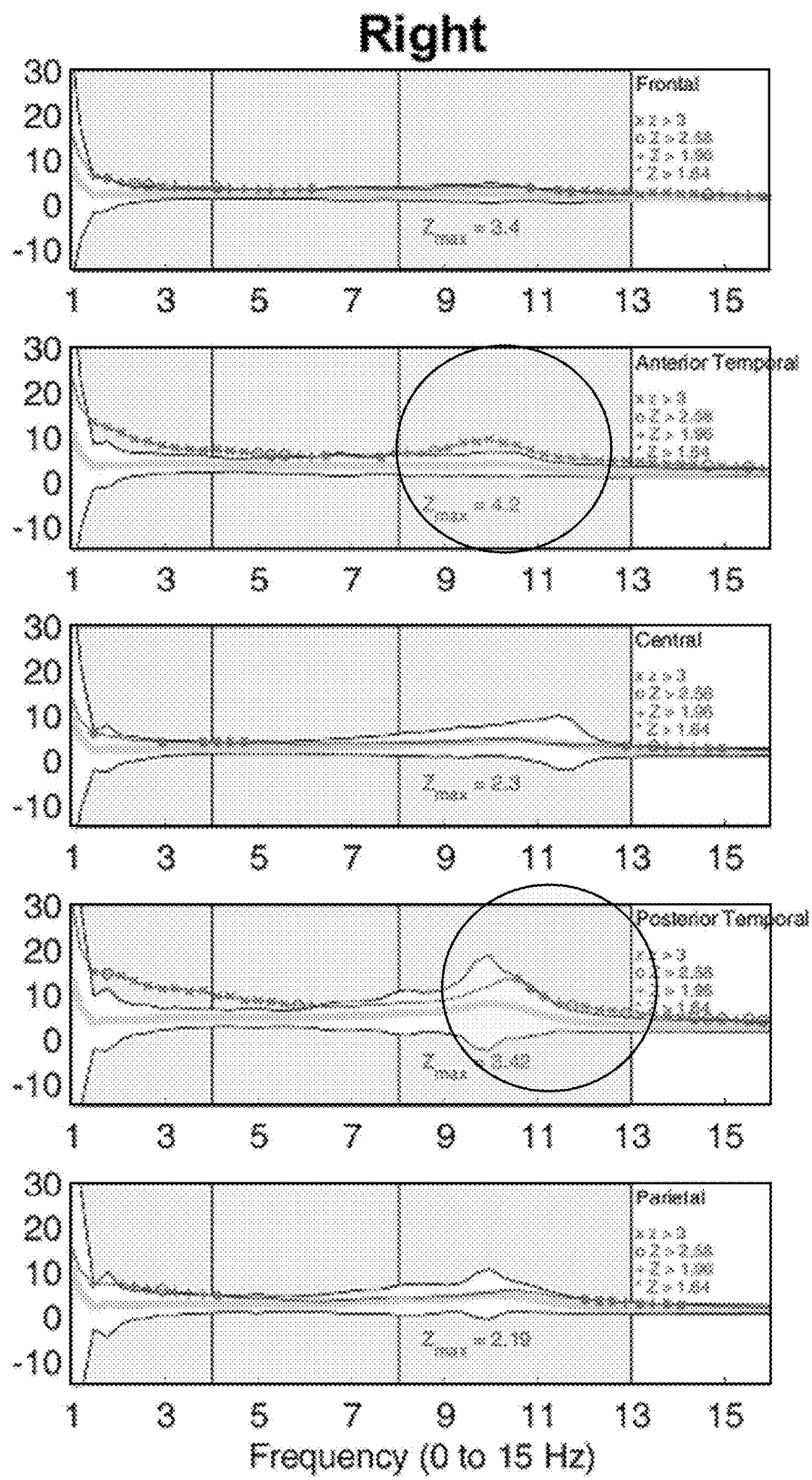

FIGS. 10A-10C show MEG source data for 9 regions of the brains for an adolescent with mTBI. FIGS. 10D-10F show MEG source data for 15 regions of the brain for the same adolescent at 7 days post-concussion. Some of the brain regions showing atypical resting-state activity in the 15 brain region model but not 9 brain region model are highlighted with a circle. The patient amplitude spectrum are plotted again the control mean and two standard deviation lines. Atypically high resting-state activity (based on Z-scores) is marked. Frequency is shown on the x axis (Hz) and strength of neural activity on the y axis (amplitude).

Figure 11A:
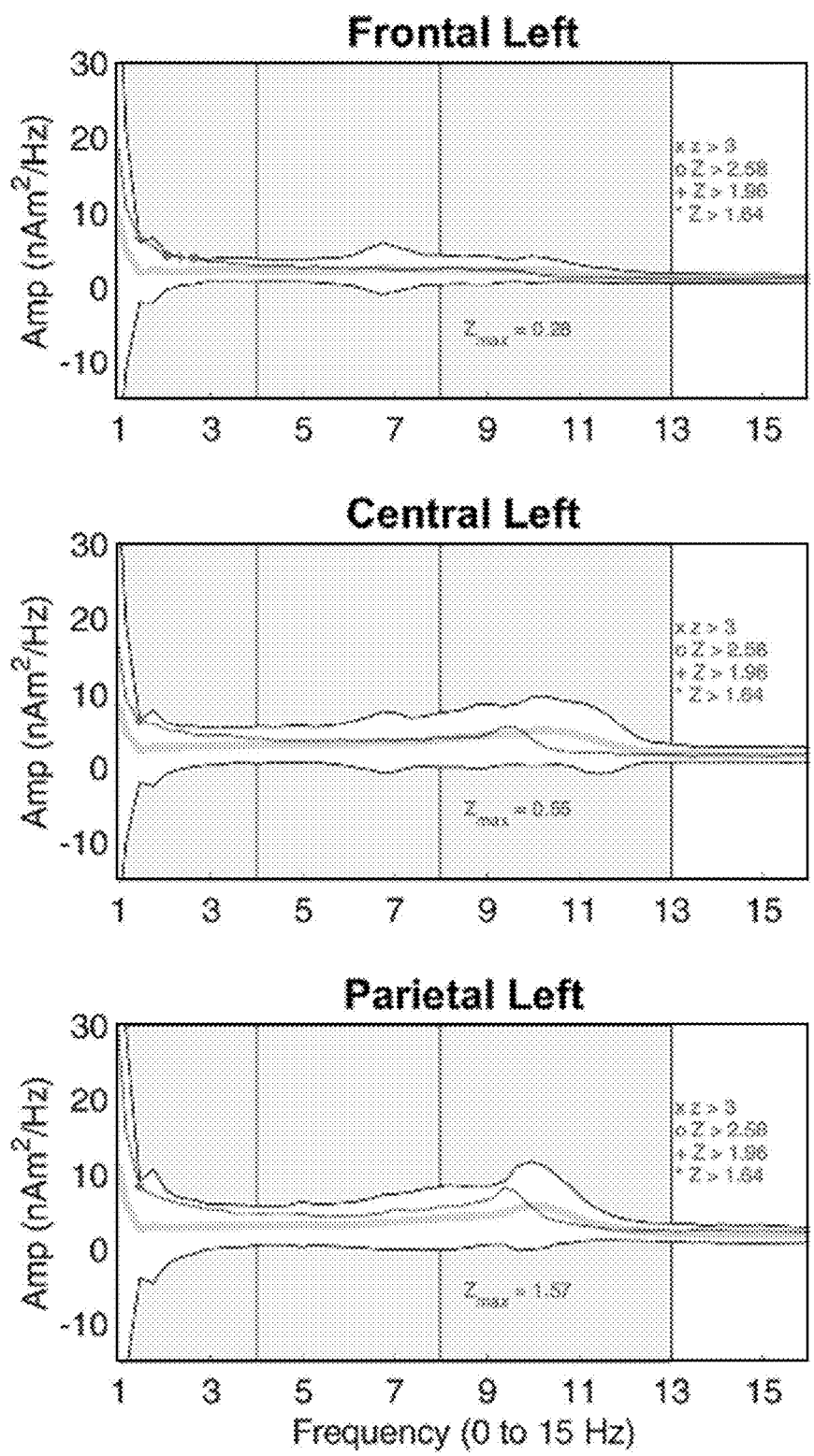
Figure 11B:
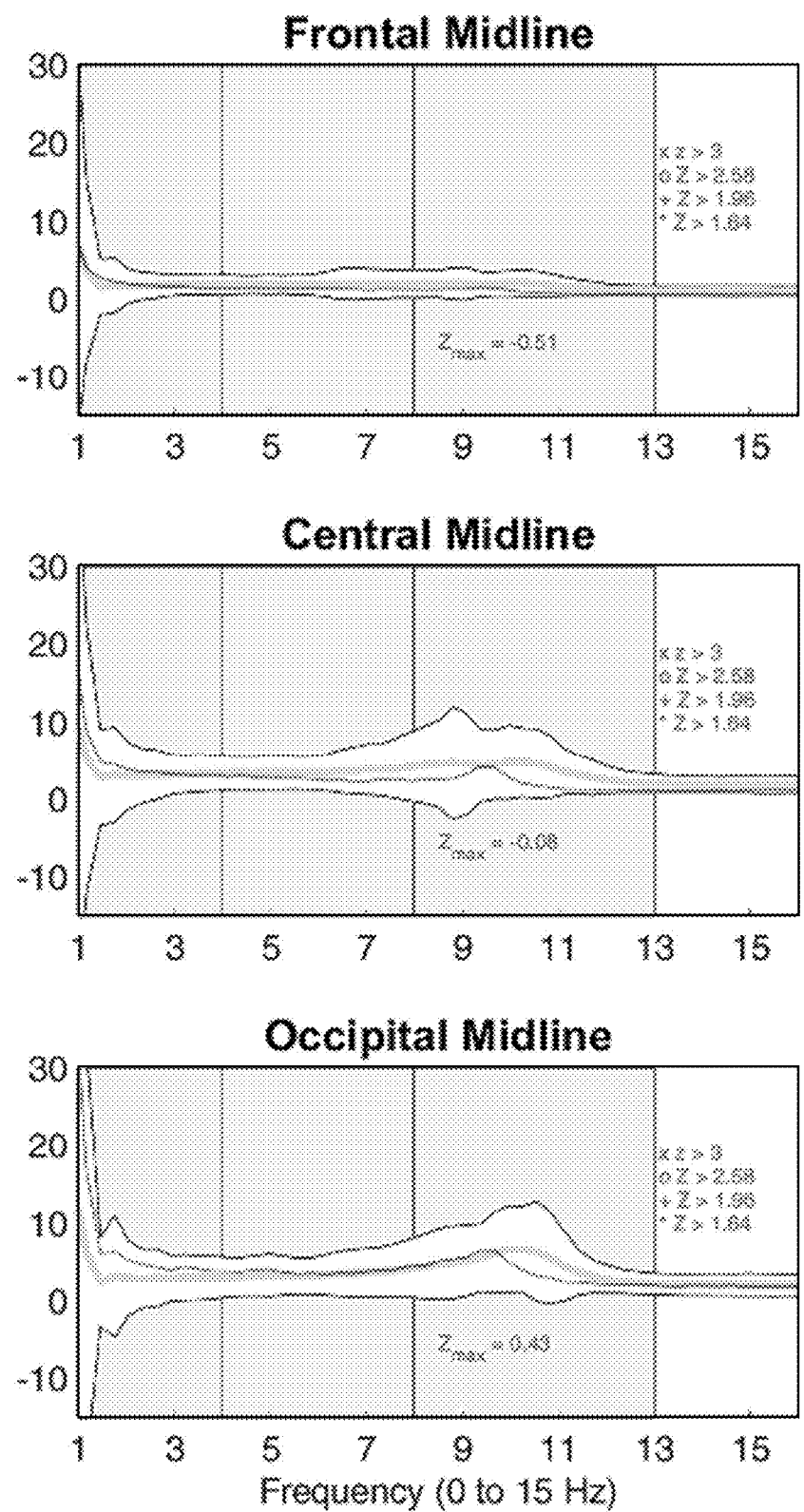
Figure 11C:
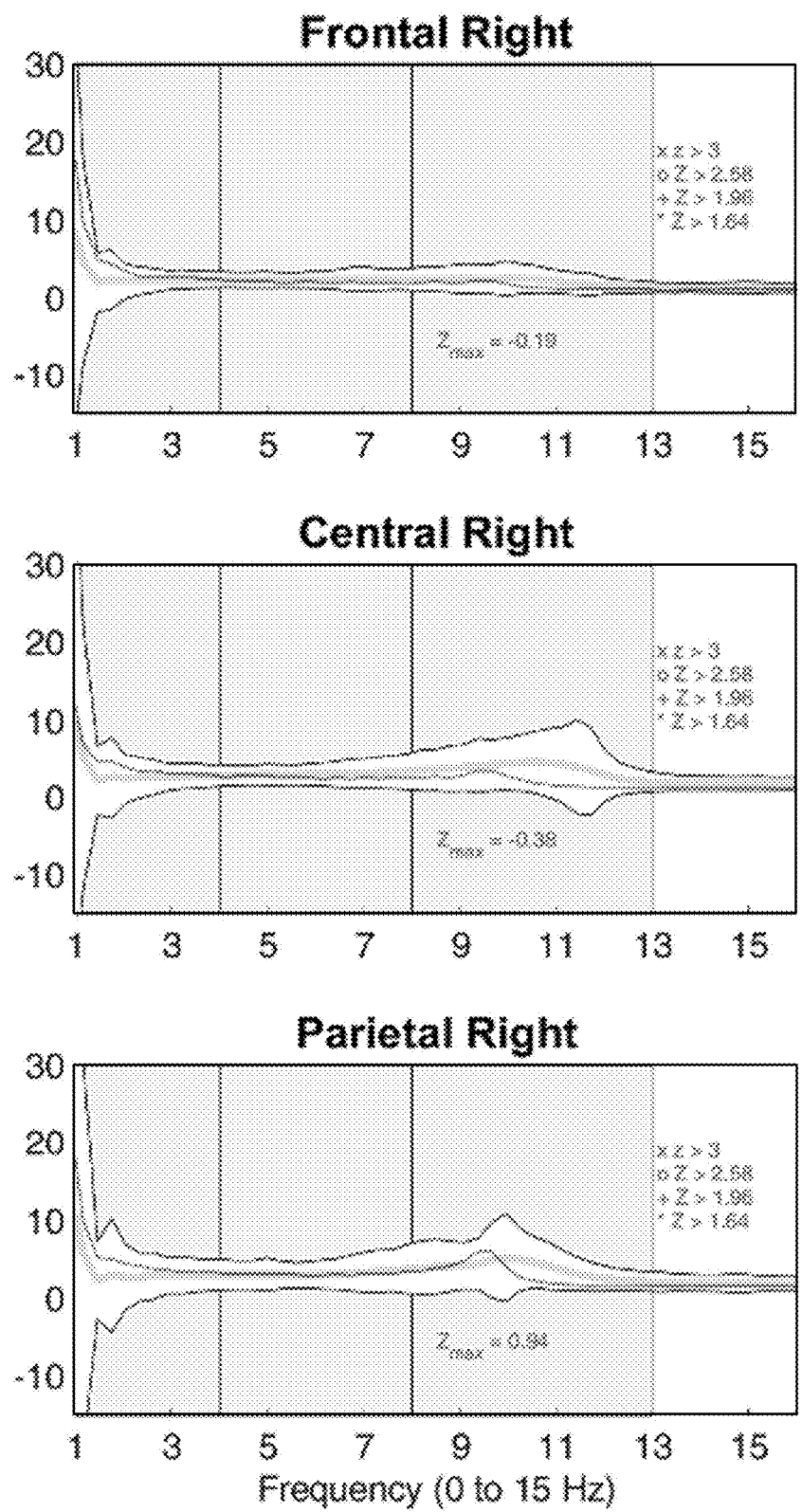
Figure 11D:
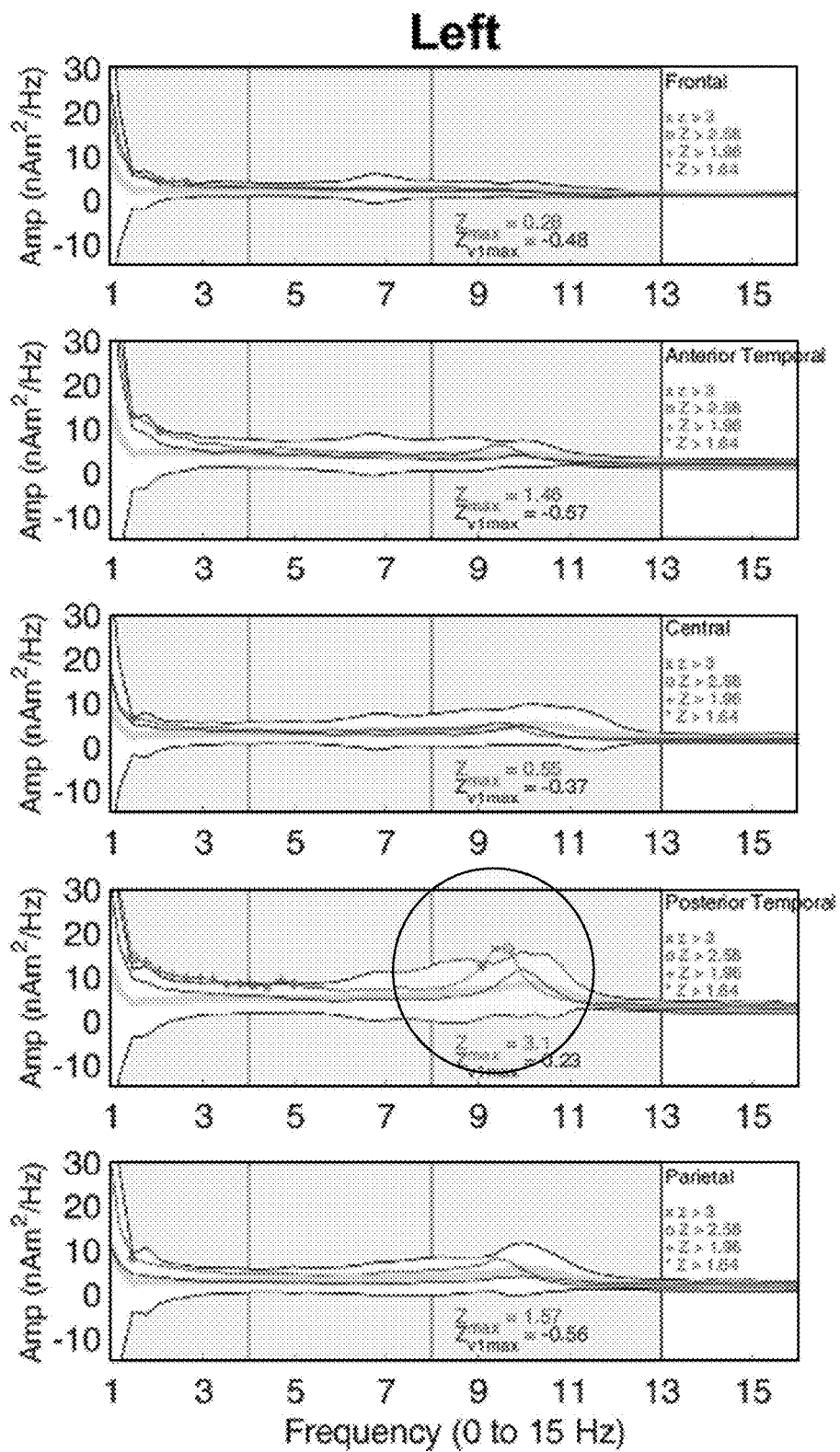
Figure 11E:
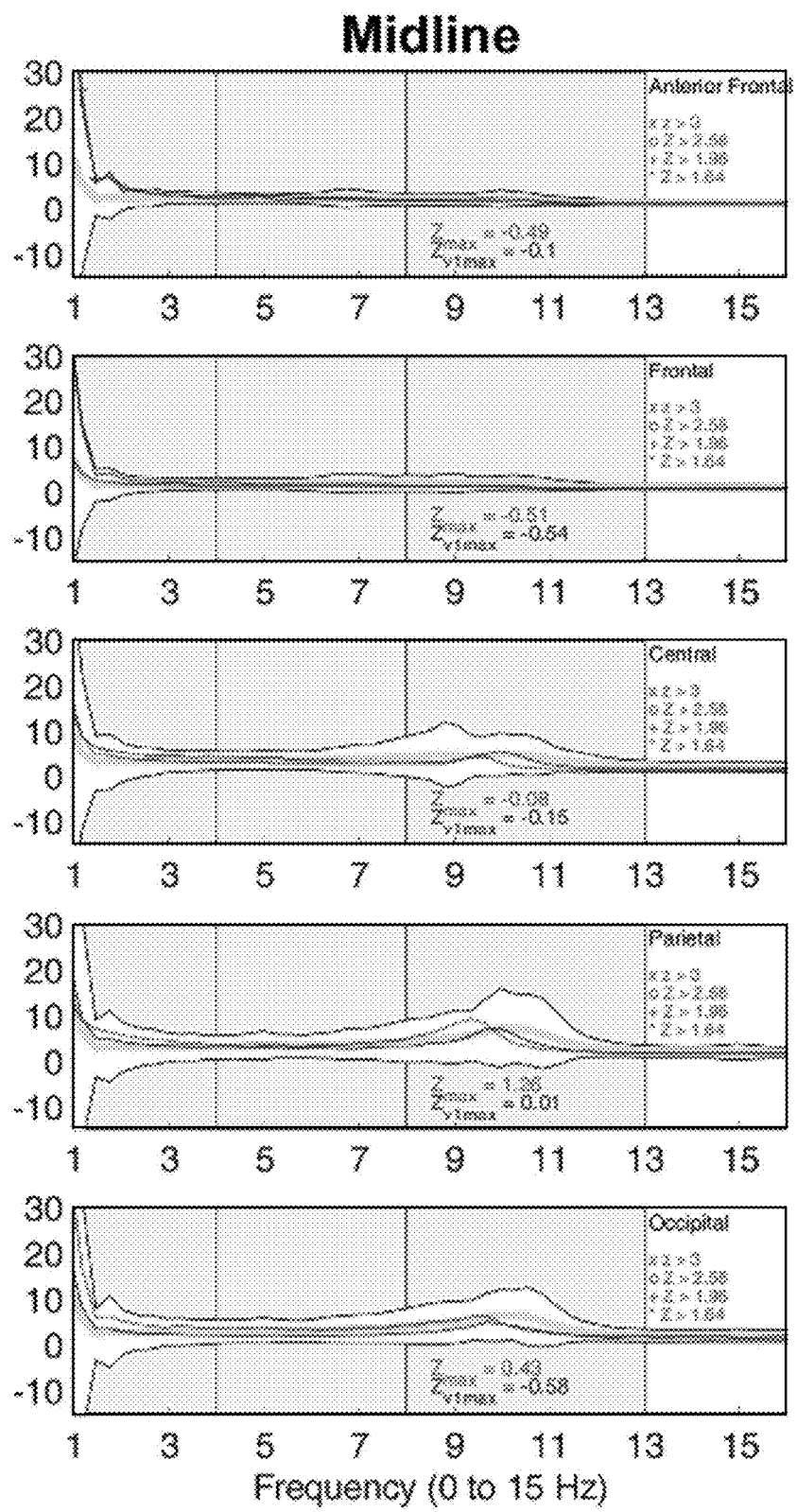
Figure 11F:
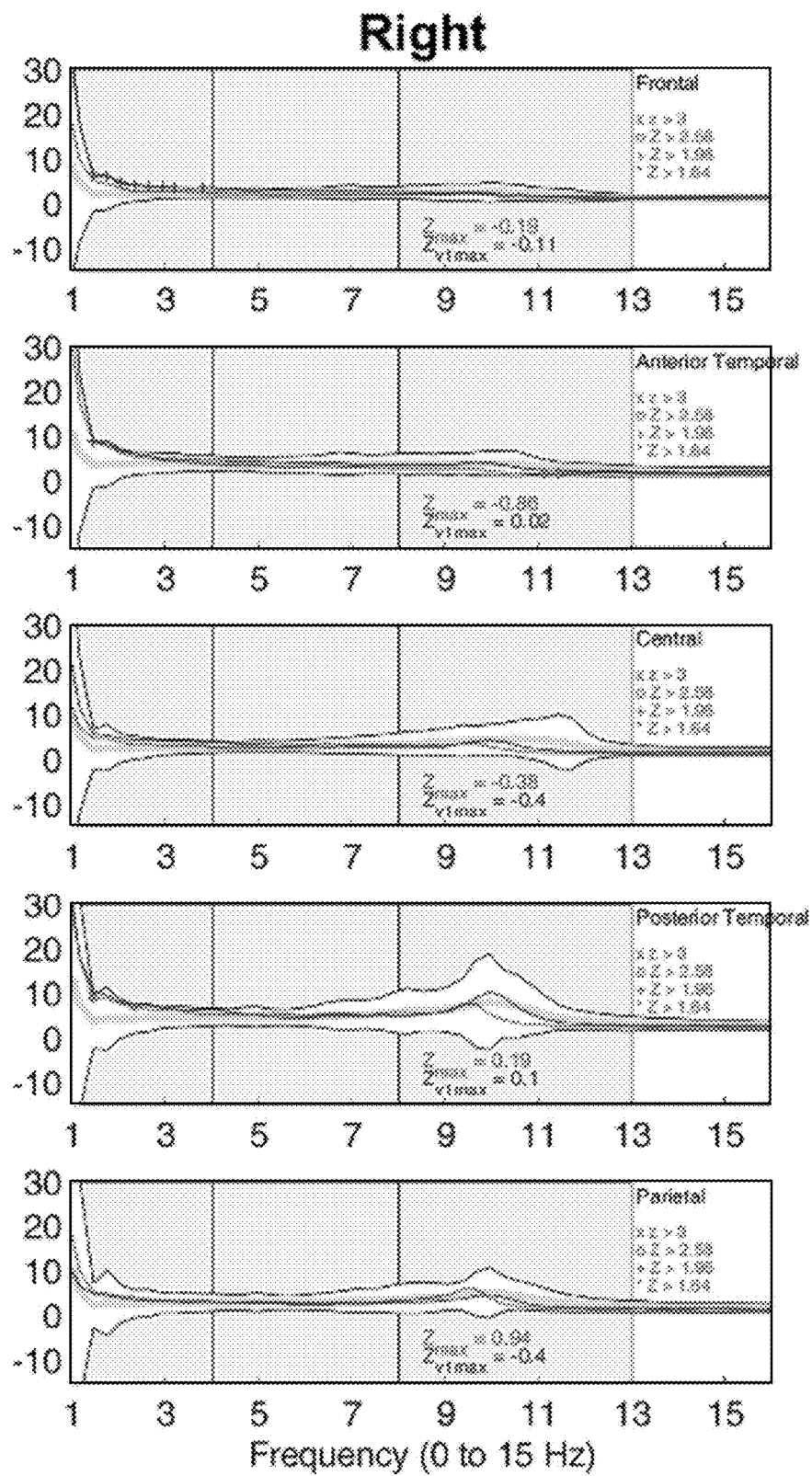

FIGS. 11A-11C show MEG source data for 9 regions of the brains for an adolescent with mTBI. FIGS. 11D-11F show MEG source data for 15 regions of the brain for the same adolescent at 5 days post-concussion. Some of the brain regions showing atypical resting-state activity in the 15 brain region model but not 9 brain region model are highlighted with a circle. The patient amplitude spectrum are plotted again the control mean and two standard deviation lines. Atypically high resting-state activity (based on Z-scores) is marked. Frequency is shown on the x axis (Hz) and strength of neural activity on the y axis (amplitude).

Figure 12A:
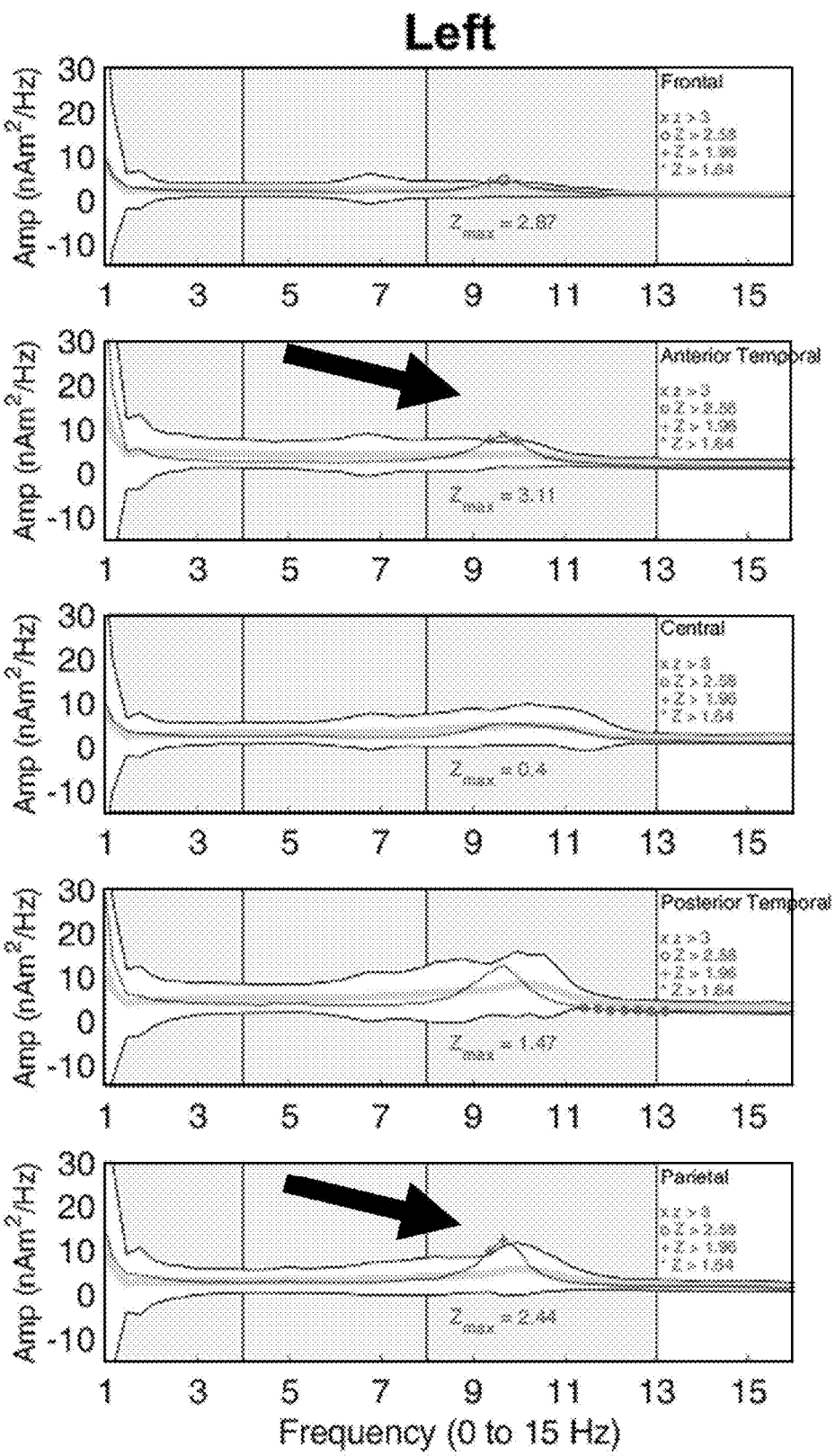
Figure 12B:
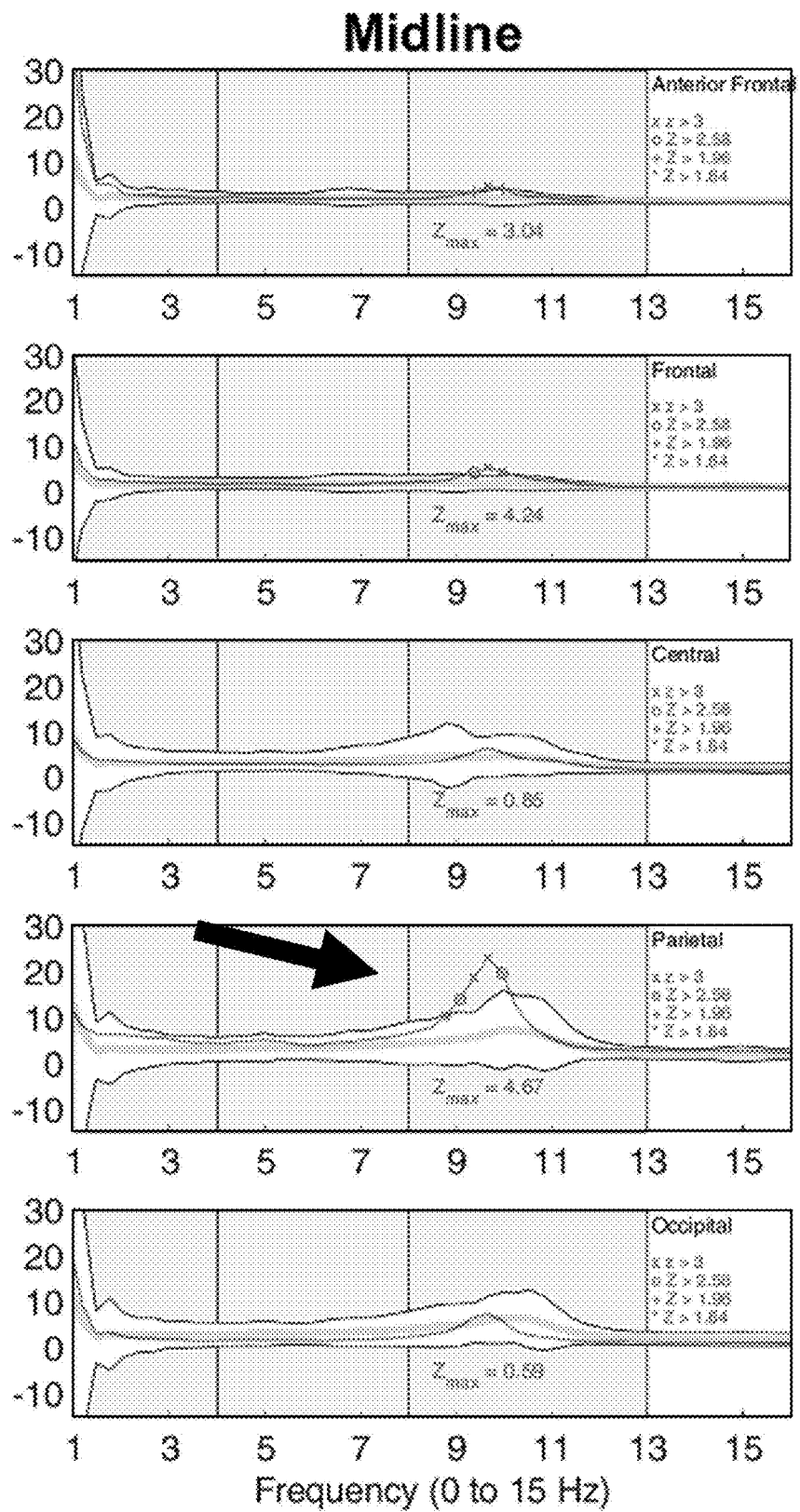
Figure 12C:
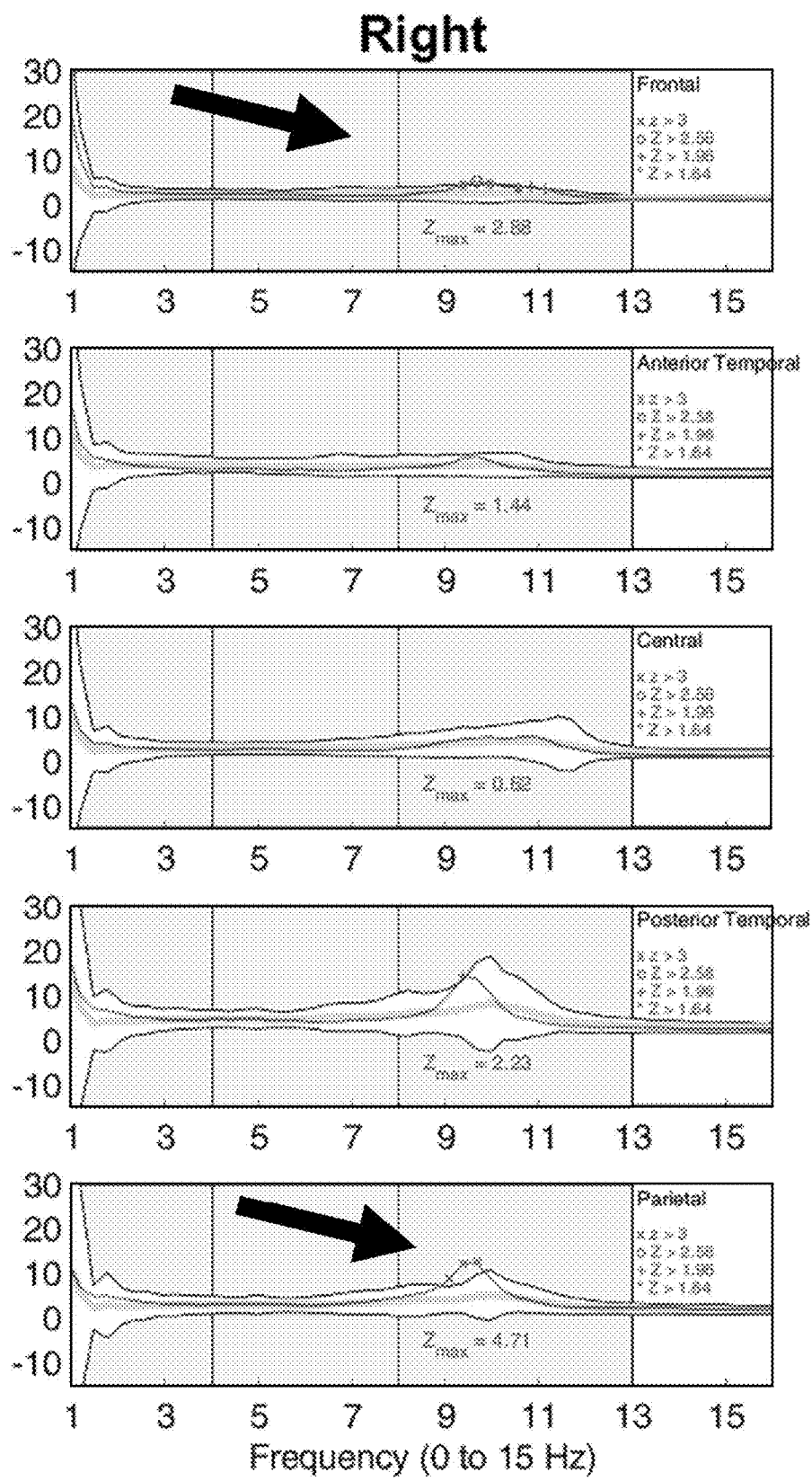
Figure 12D:
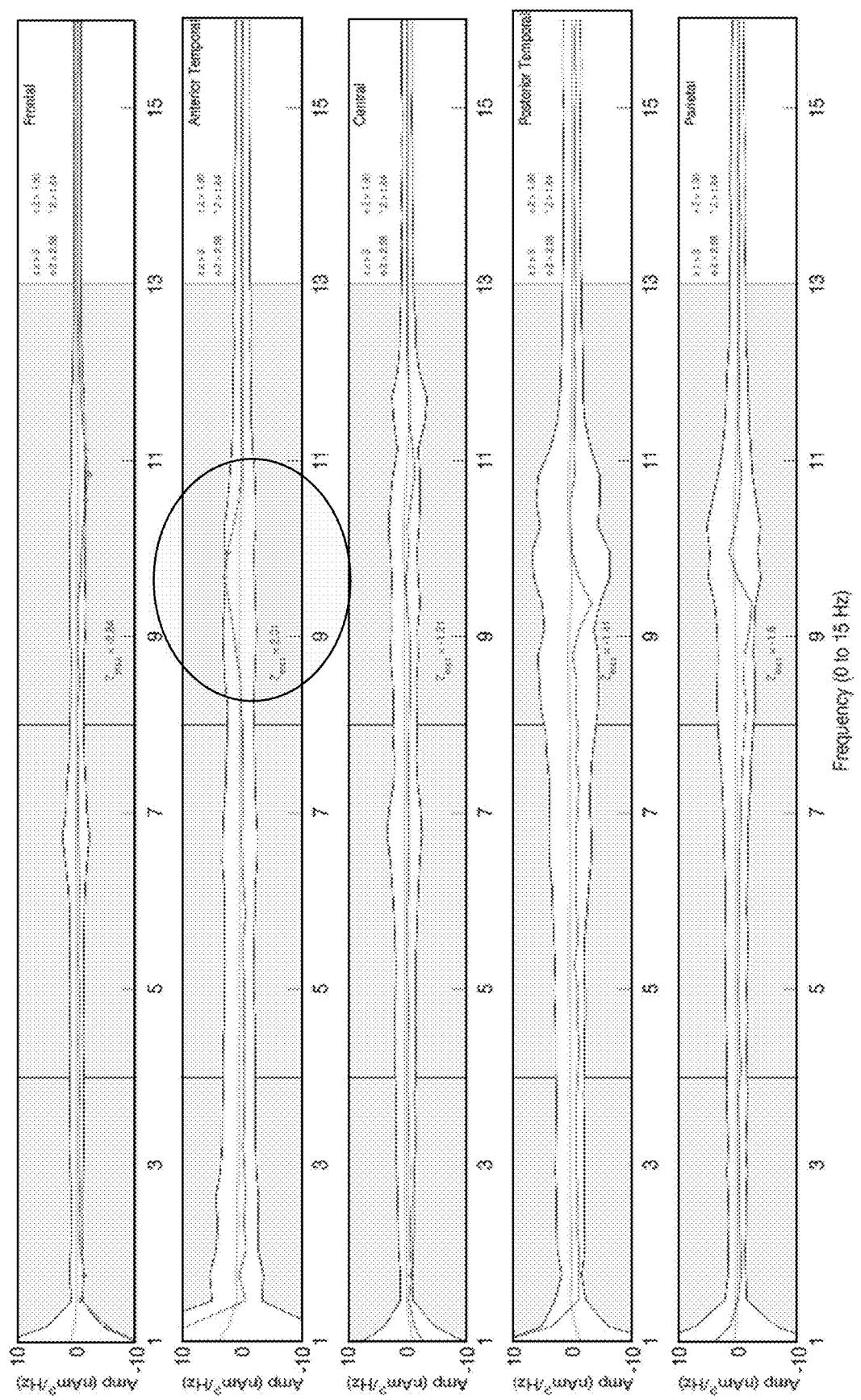

FIGS. 12A-12C show amplitude spectrum from a 16-year-old female with MEG obtained 7 days after concussion (softball game). The 15 brain region source map indicates diffuse brain damage, evidenced as atypically high alpha activity in many areas of the brain (see Z-scores and black arrows). FIG. 12D provides the hemisphere-difference laterality Z-score measures. The data indicates greater damage on the left than right frontal regions (see circled area).

Figure 13A:
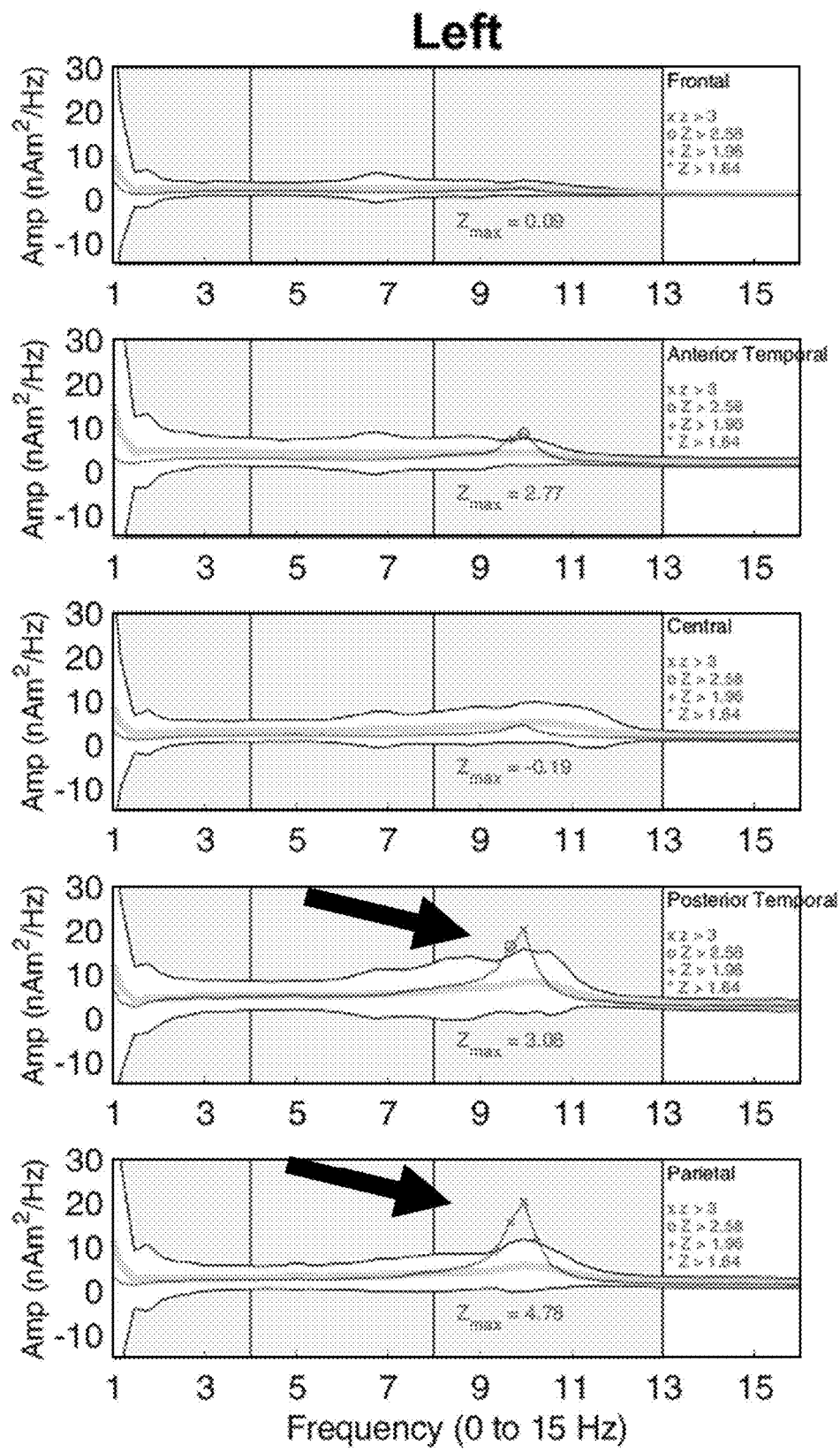
Figure 13B:
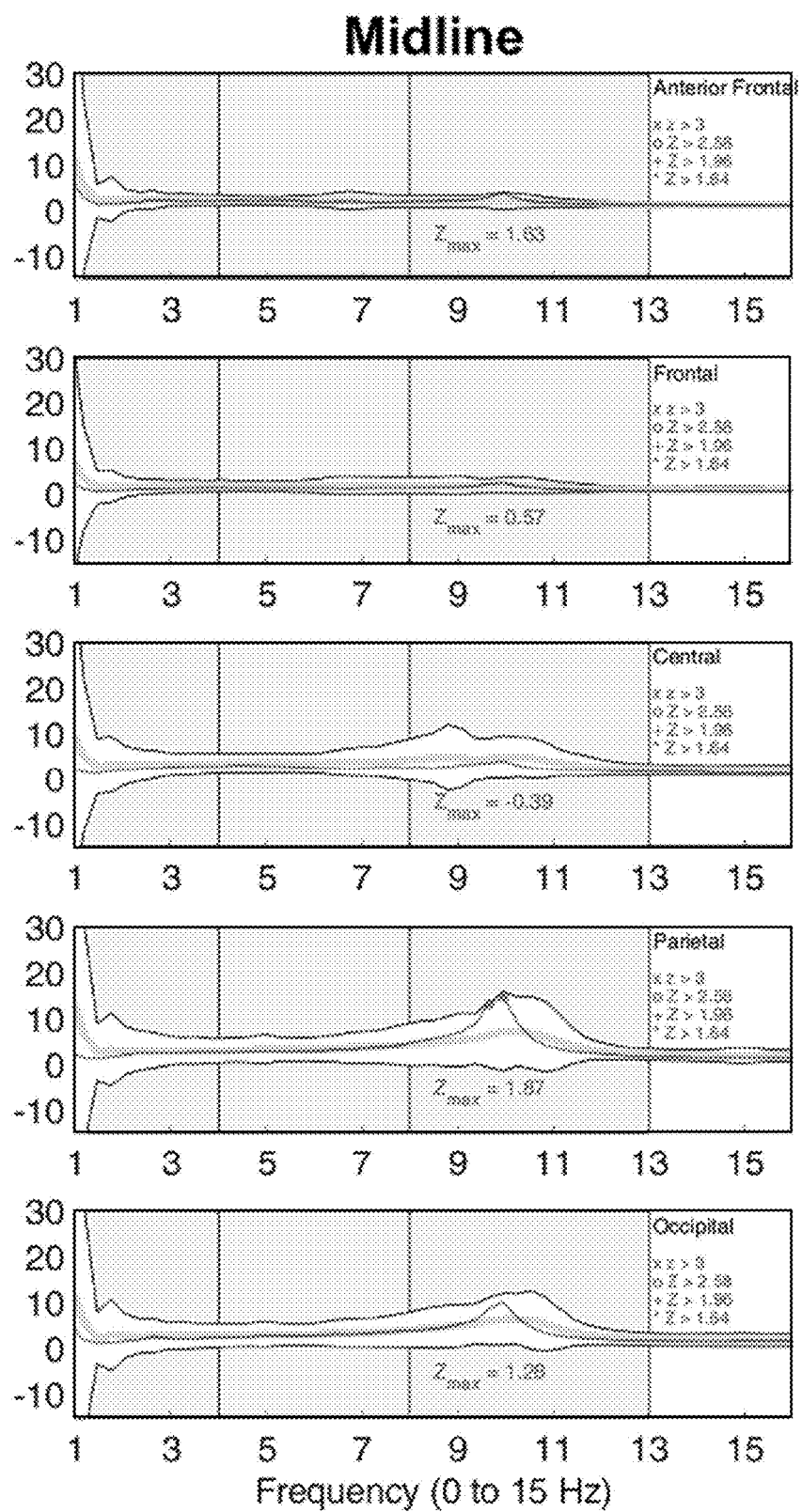
Figure 13C:
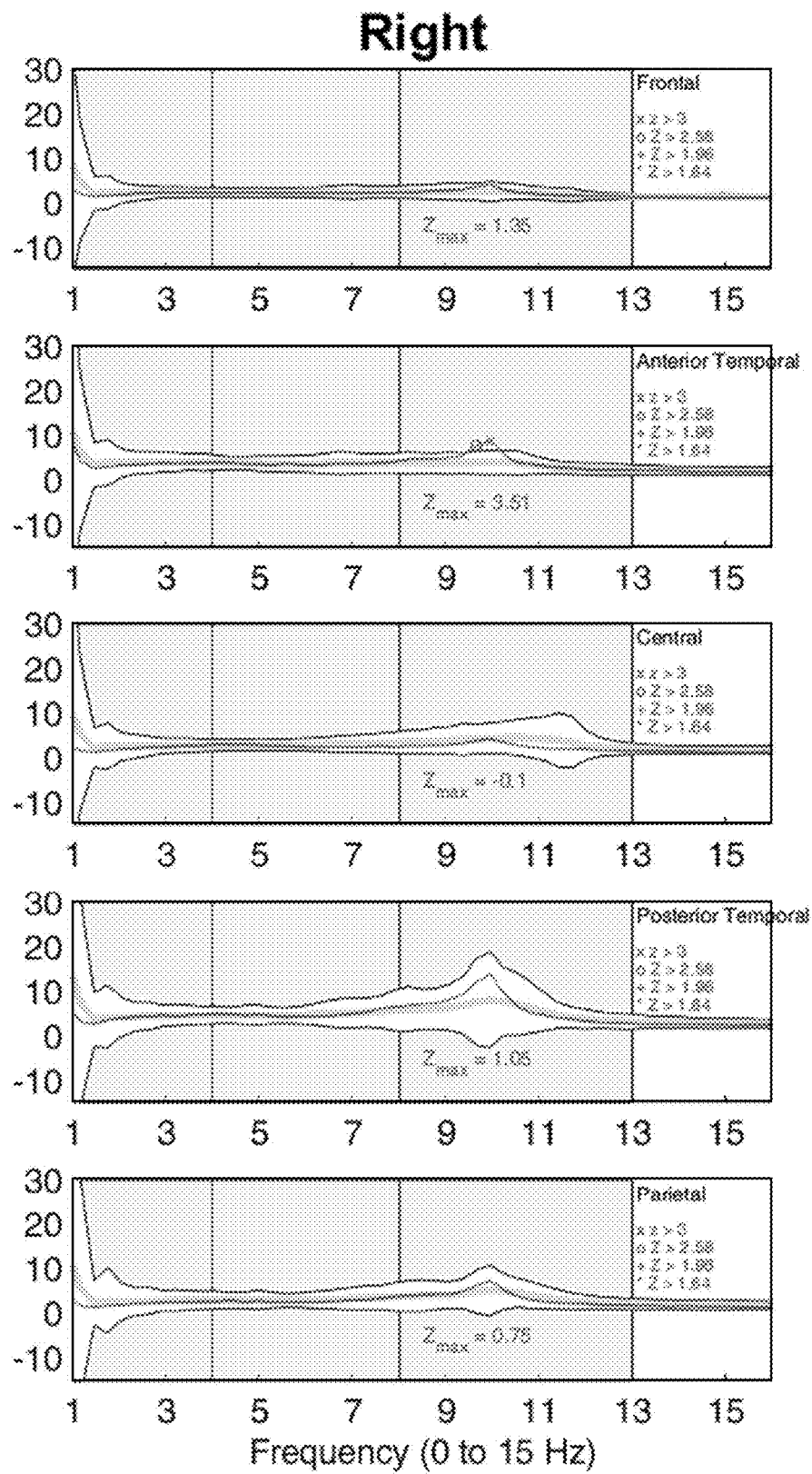
Figure 13D:
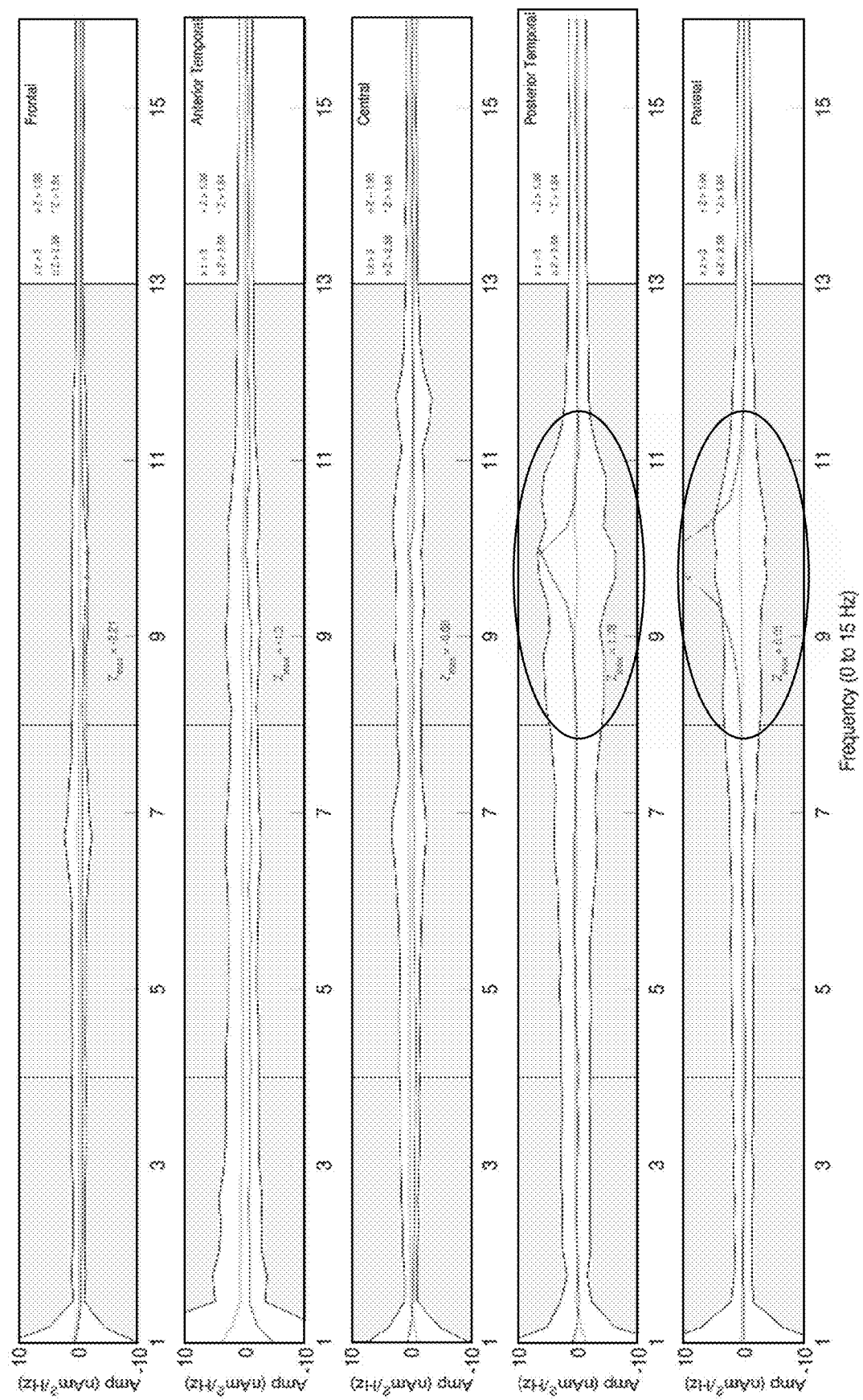

FIGS. 13A-13C show amplitude spectrum from a 13-year-old male with MEG obtained 13 days after concussion (bike accident). The 15 brain region source map indicates focal brain damage, evidenced as atypically high alpha activity in left but not right posterior brain regions (see Z-scores and black arrows). FIG. 13D provides the hemisphere-difference laterality Z-score measures. The much higher Z-scores in the hemisphere-difference Z-score maps further supports left lateralized damage (see circled areas).

Figure 14A:
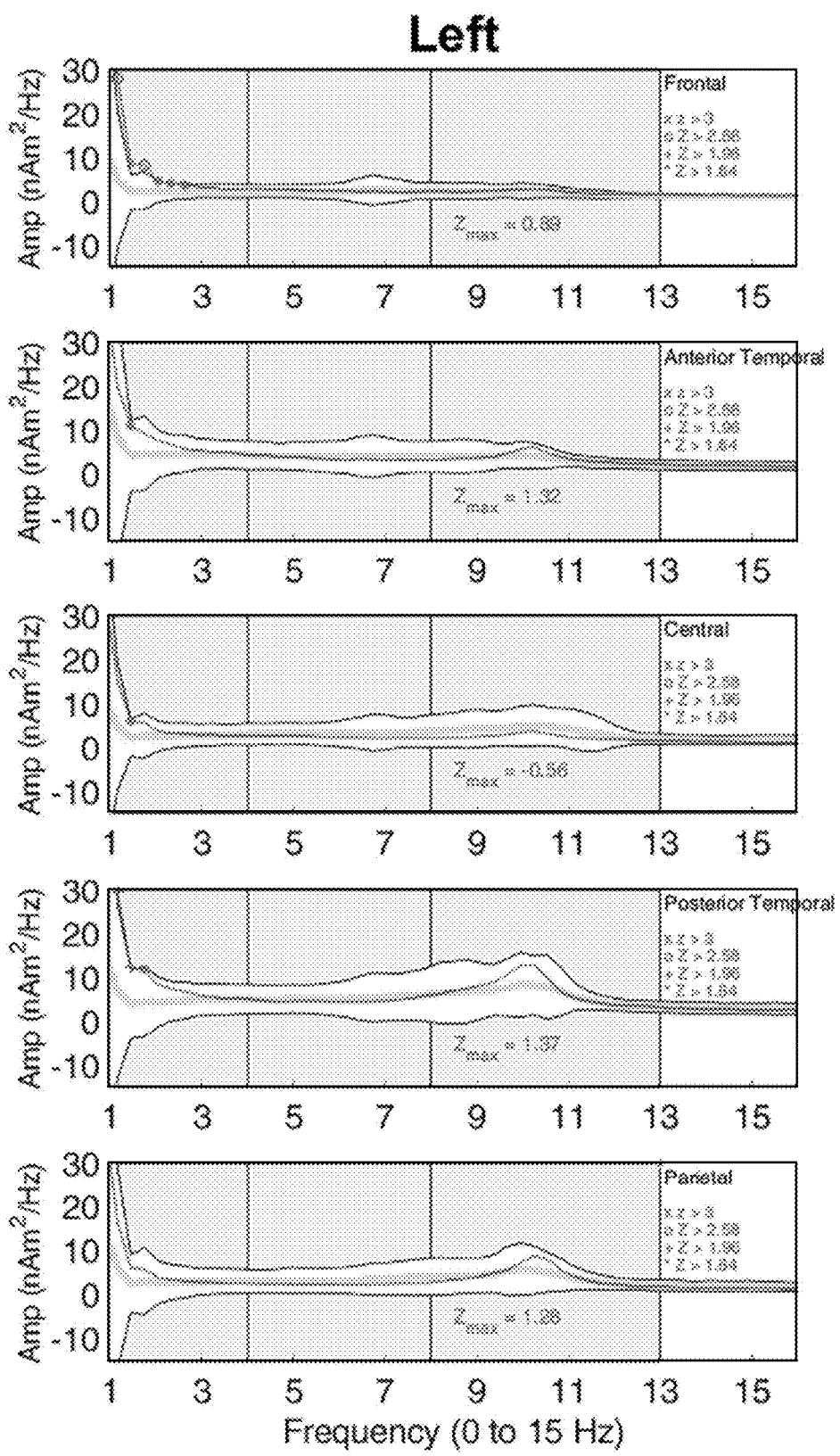
Figure 14B:
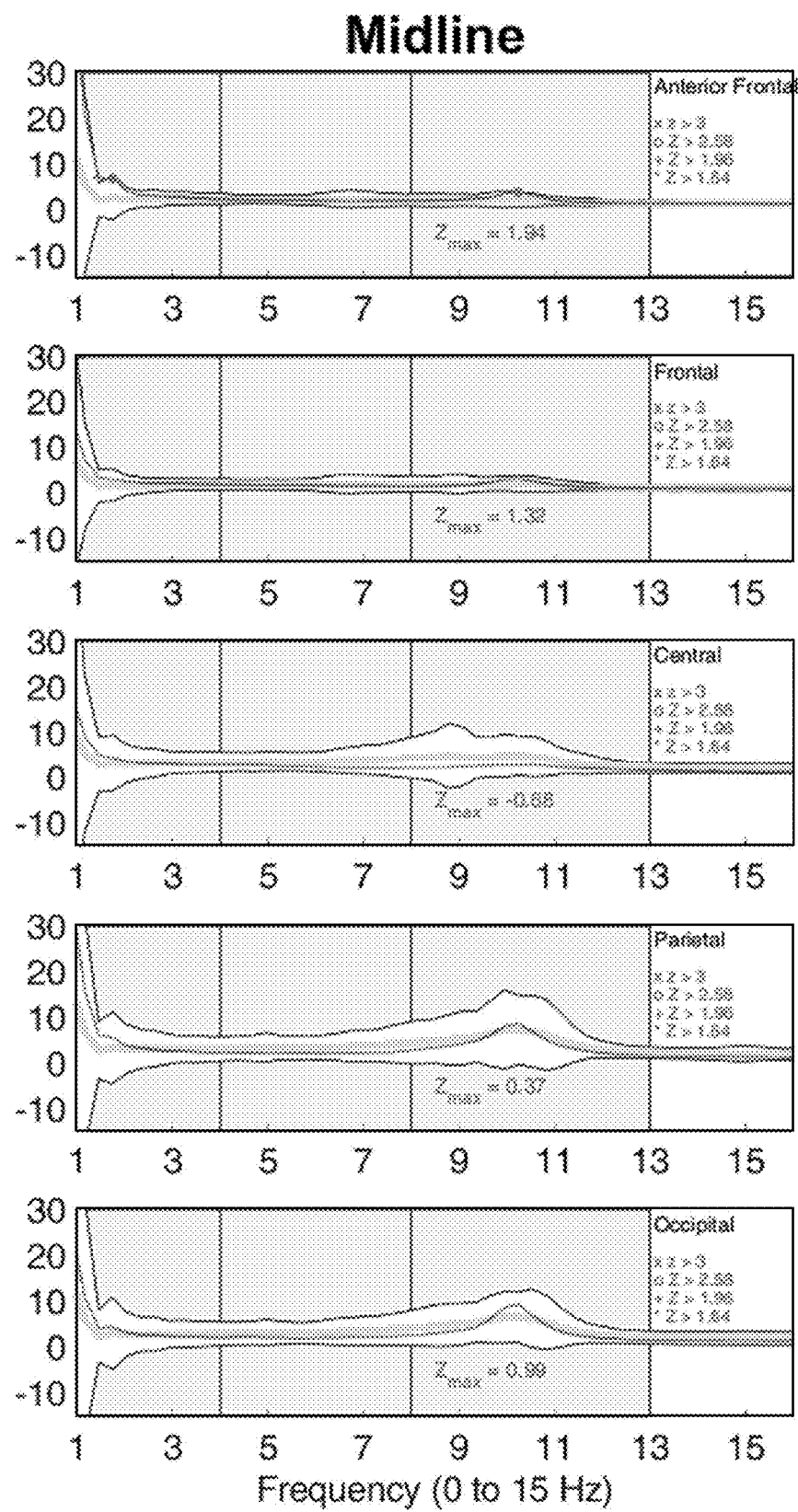
Figure 14C:
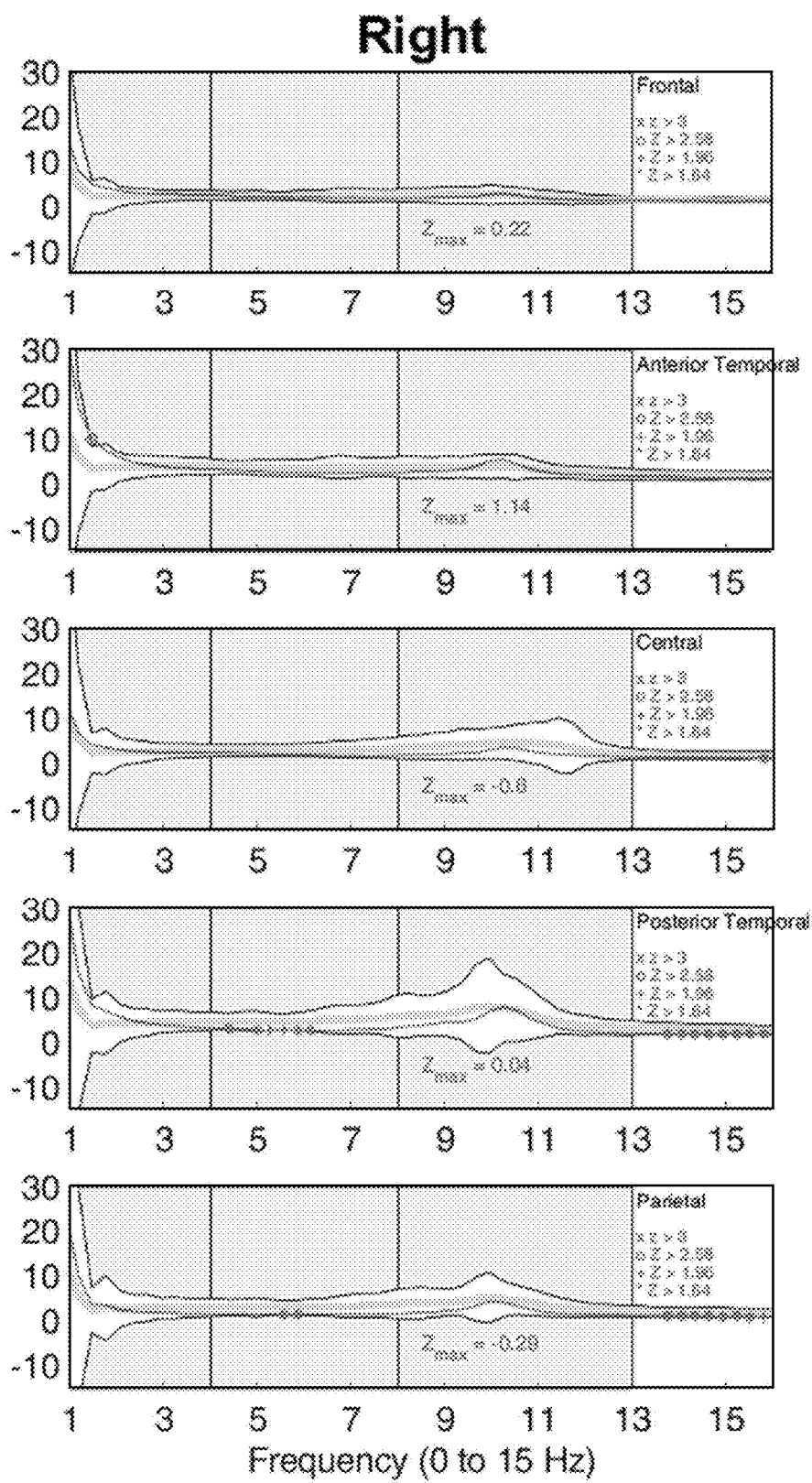
Figure 14D:
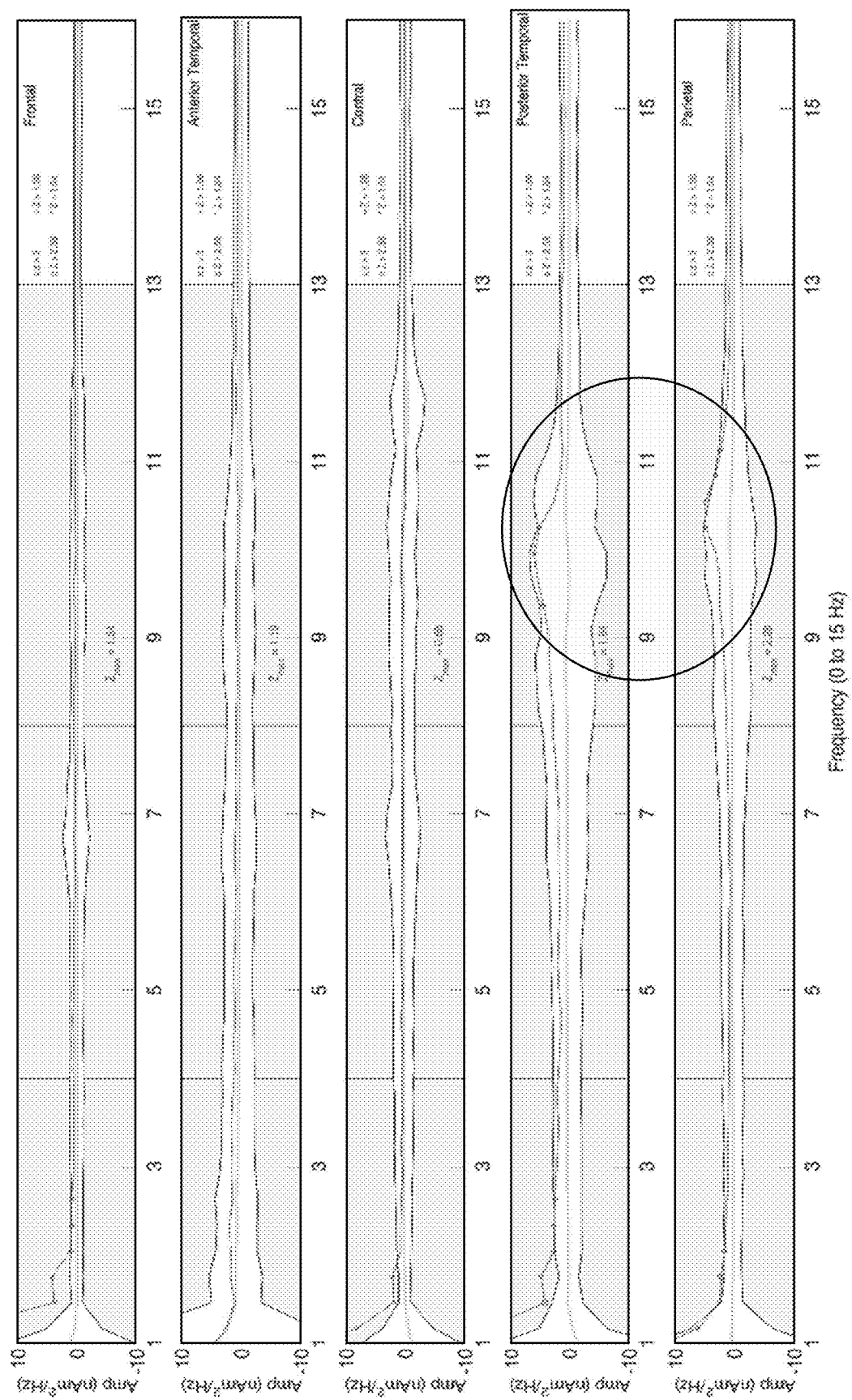

FIGS. 14A-14C show amplitude spectrum from a 13-year-old male with MEG obtained approximately 4 months after concussion (bike accident). The 15 brain region source map does not indicate brain damage at the sub-chronic exam. FIG. 14D provides the hemisphere-difference laterality Z-score measures. Higher Z-scores in the hemisphere-difference Z-score maps indicate residual atypical brain activity in the left hemisphere (see circled areas).

Figure 15A:
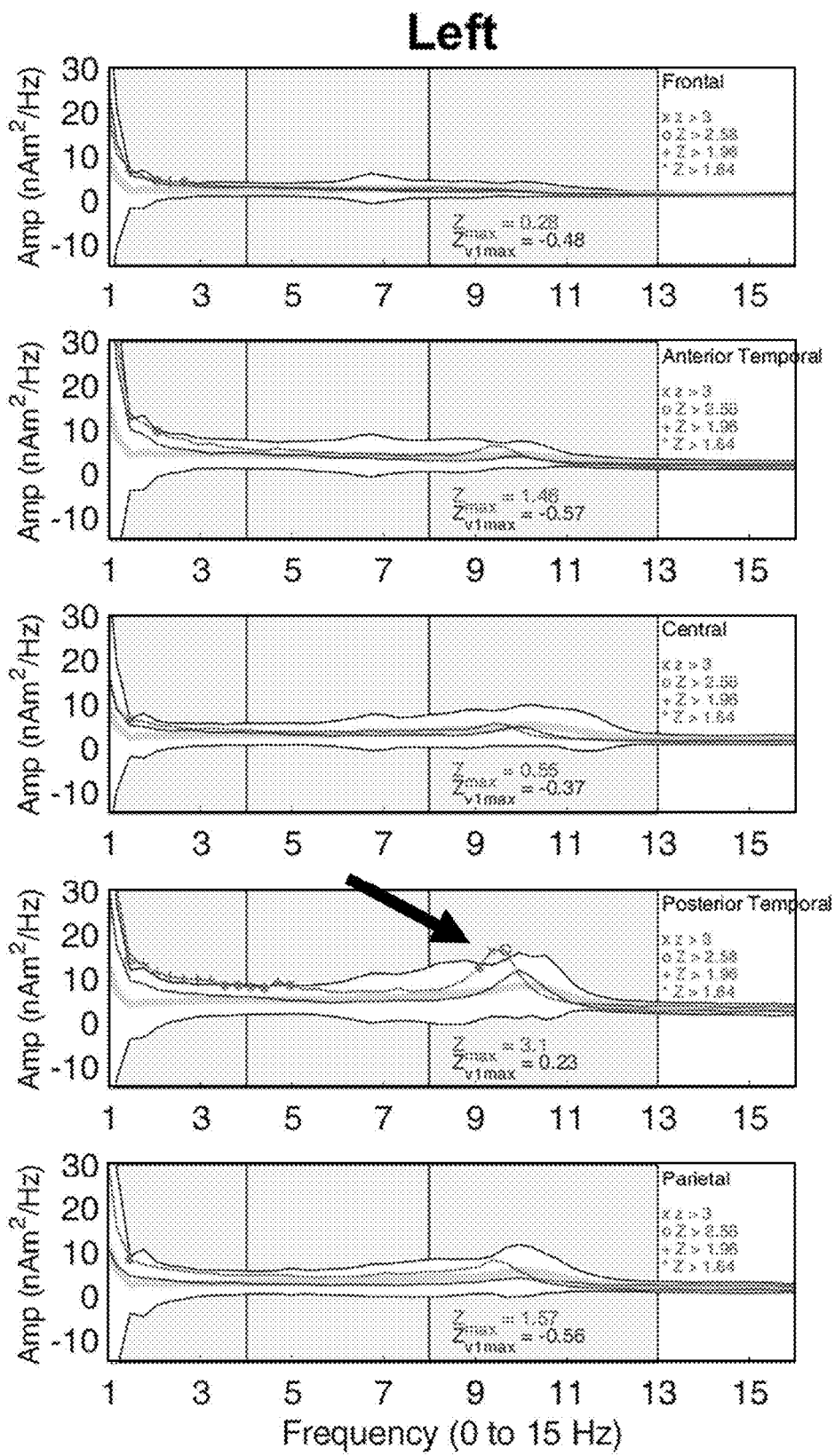
Figure 15B:
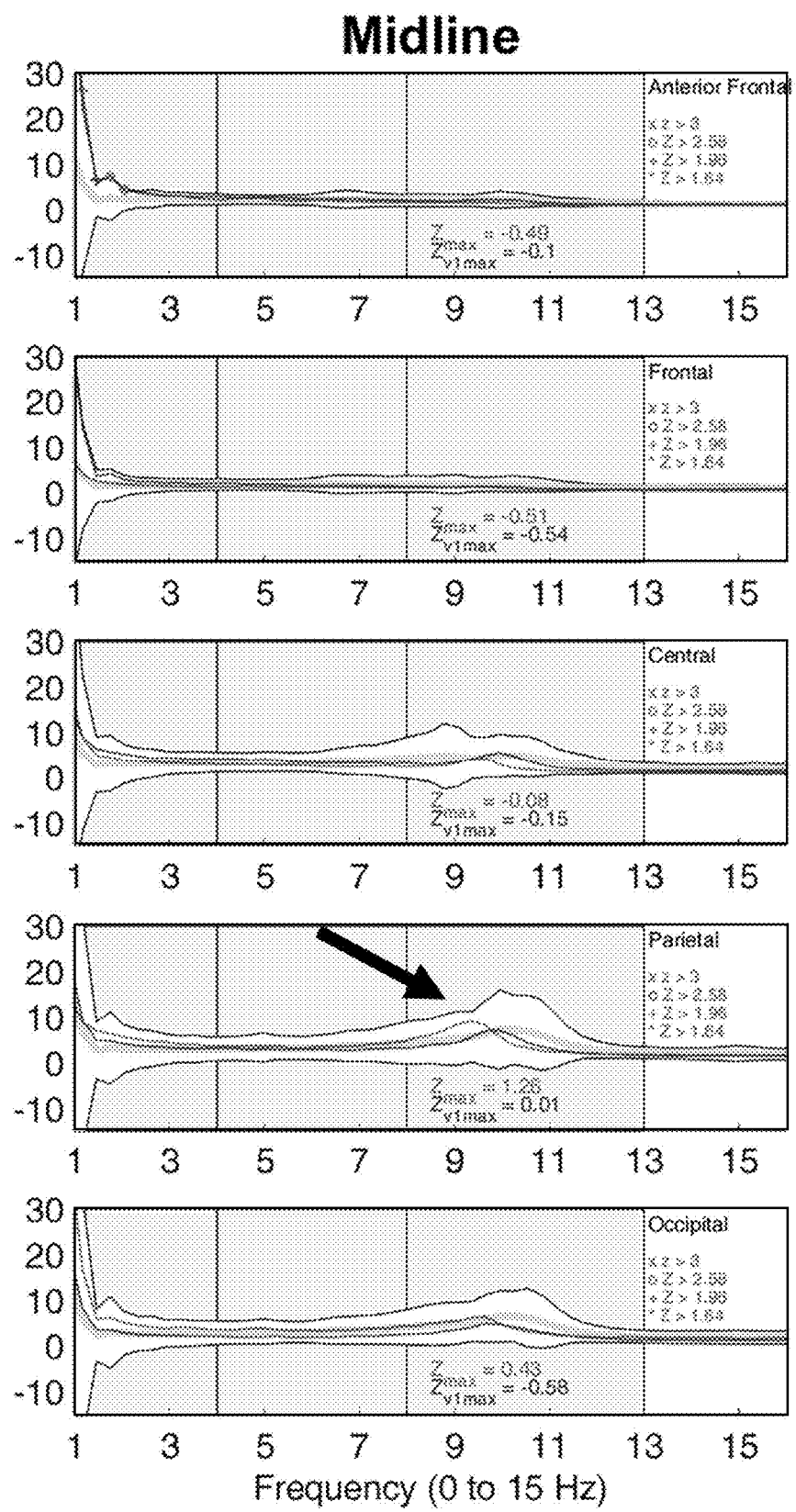
Figure 15C:
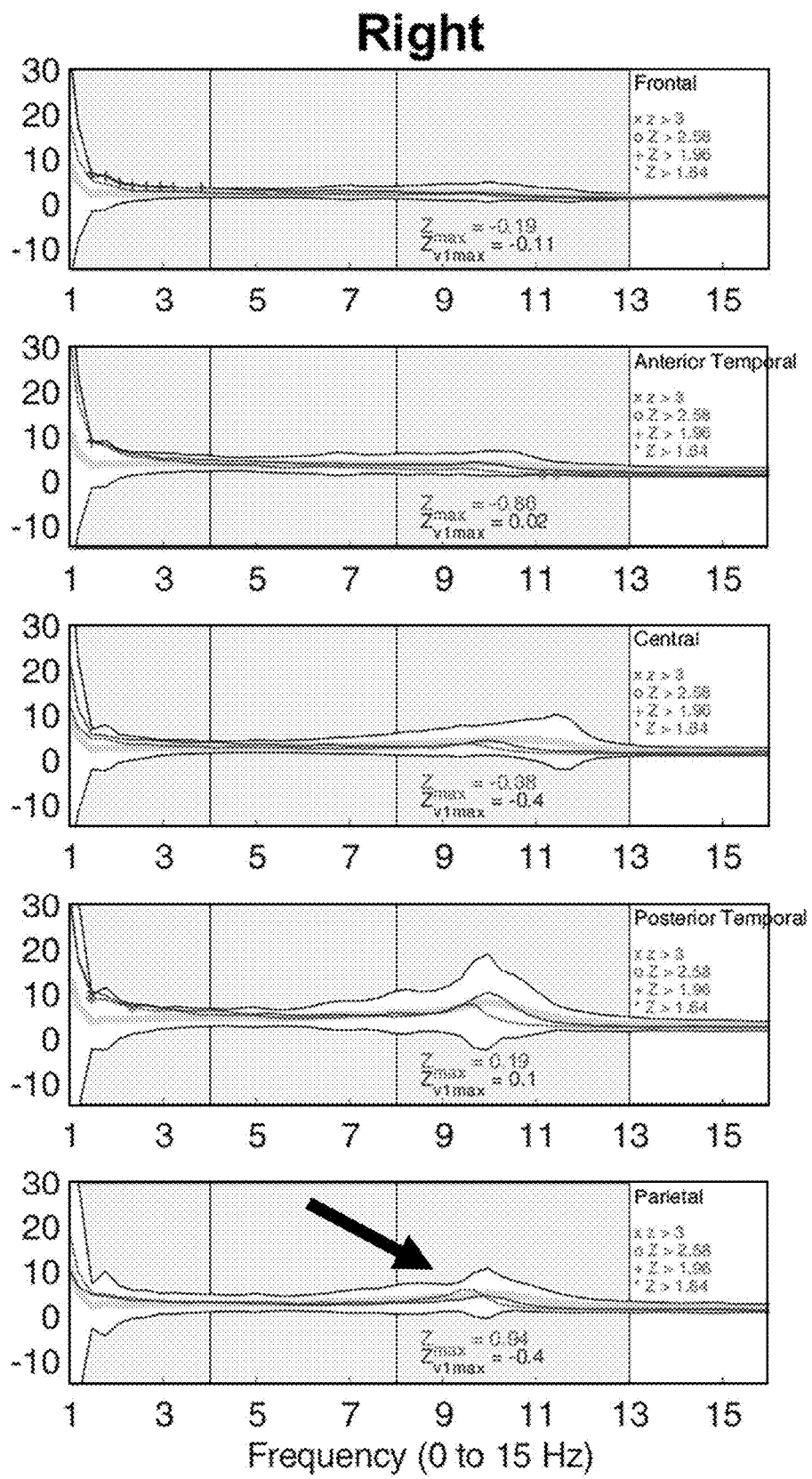
Figure 16A:
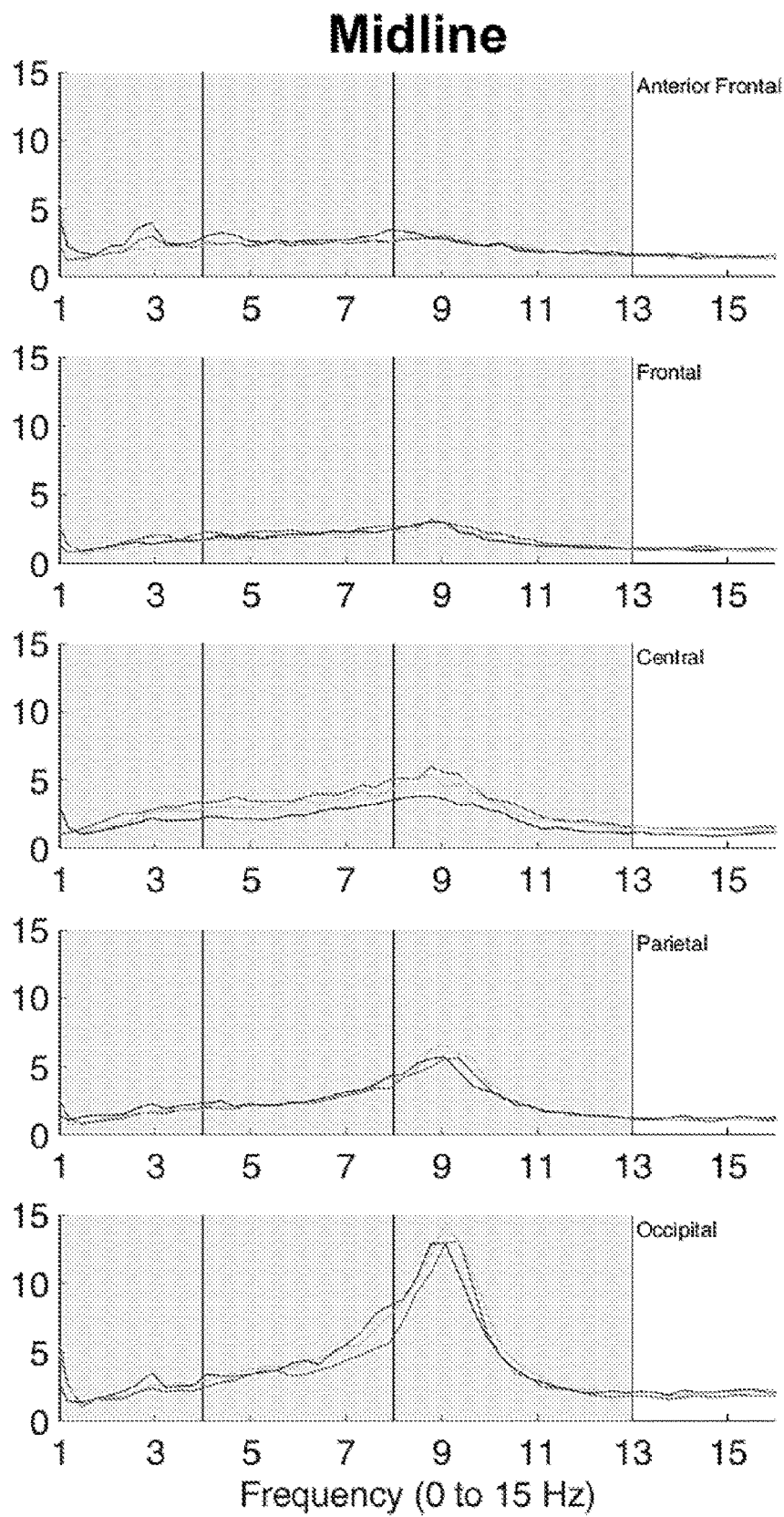
Figure 16B:
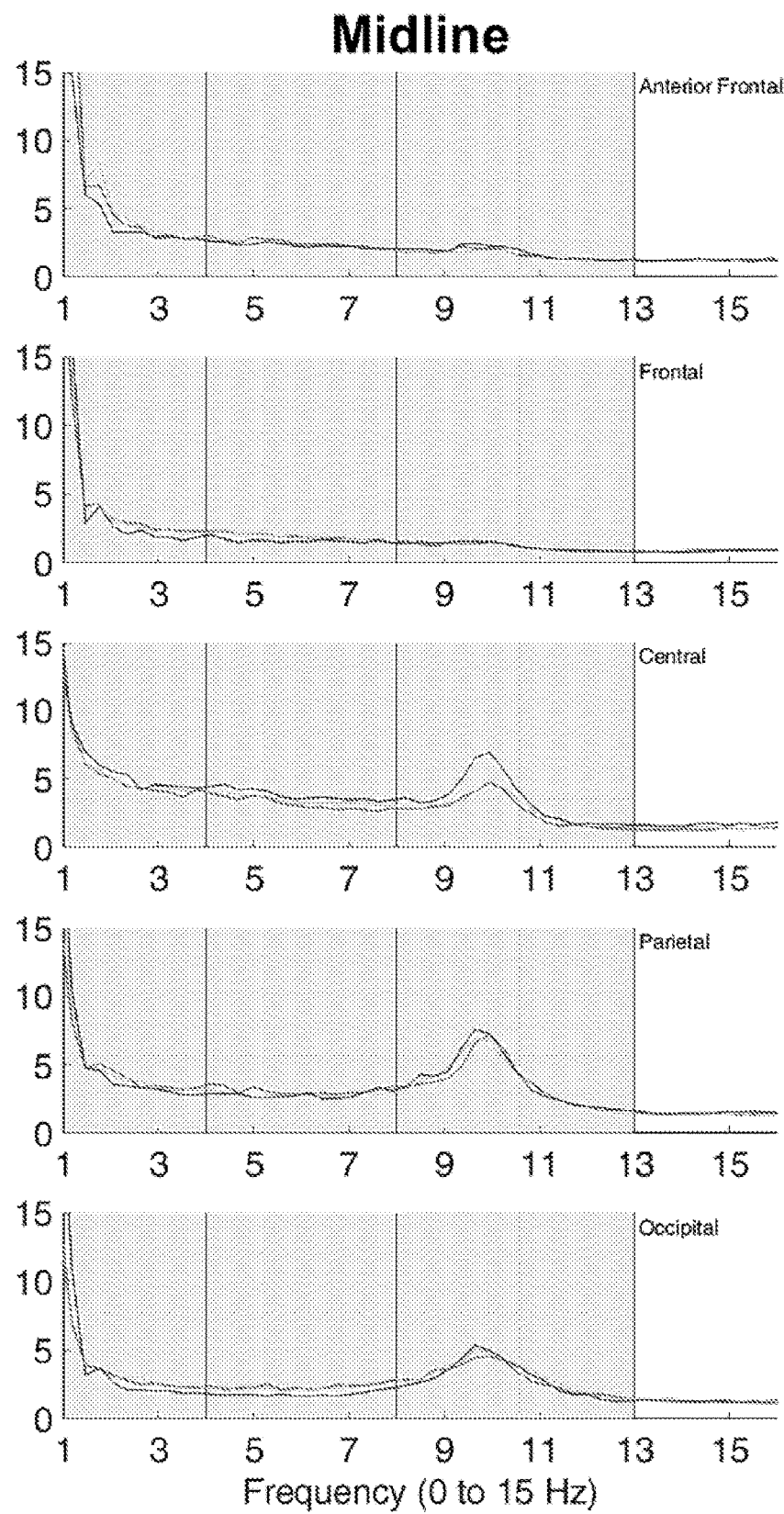
Figure 16C:
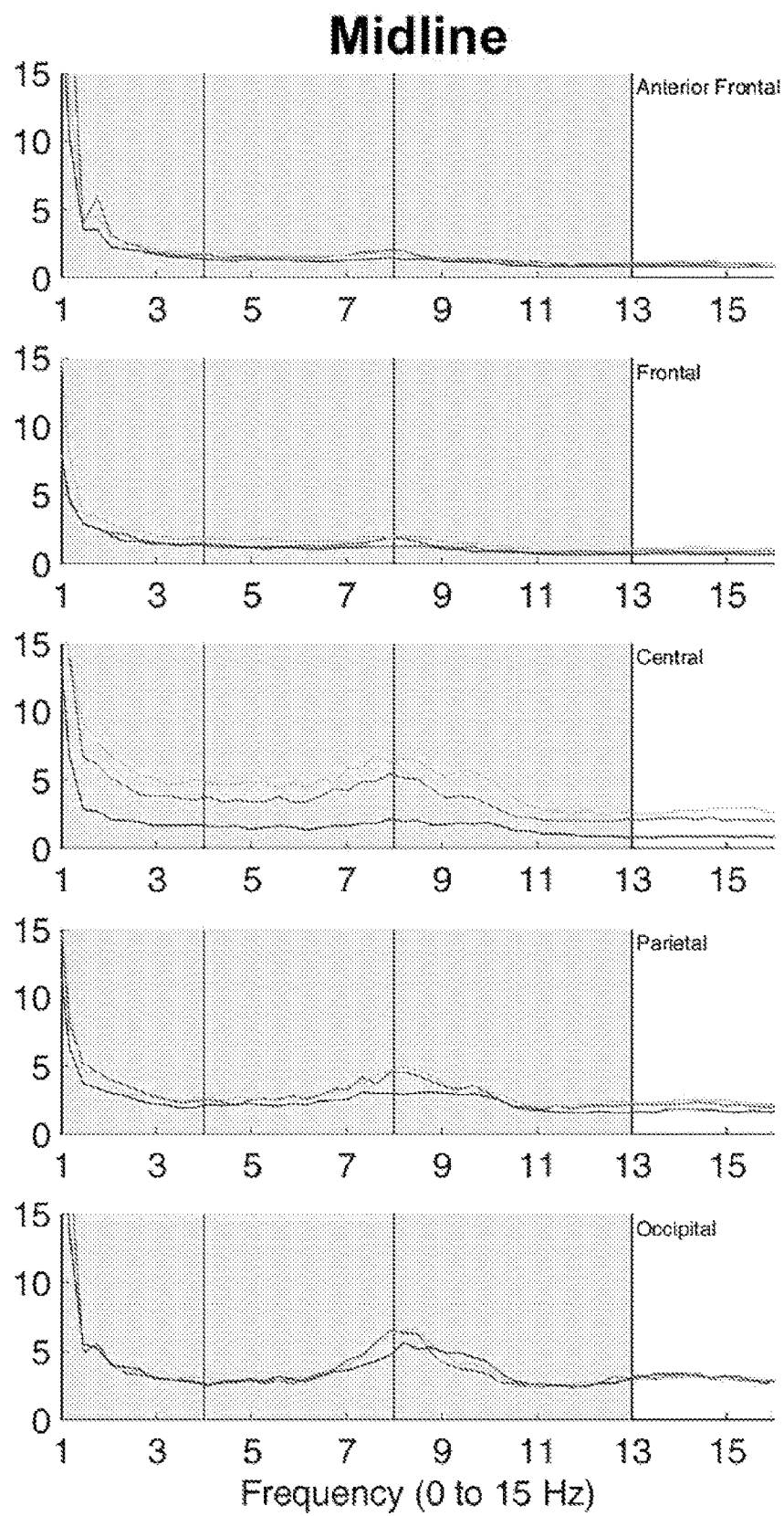
Figure 16D:
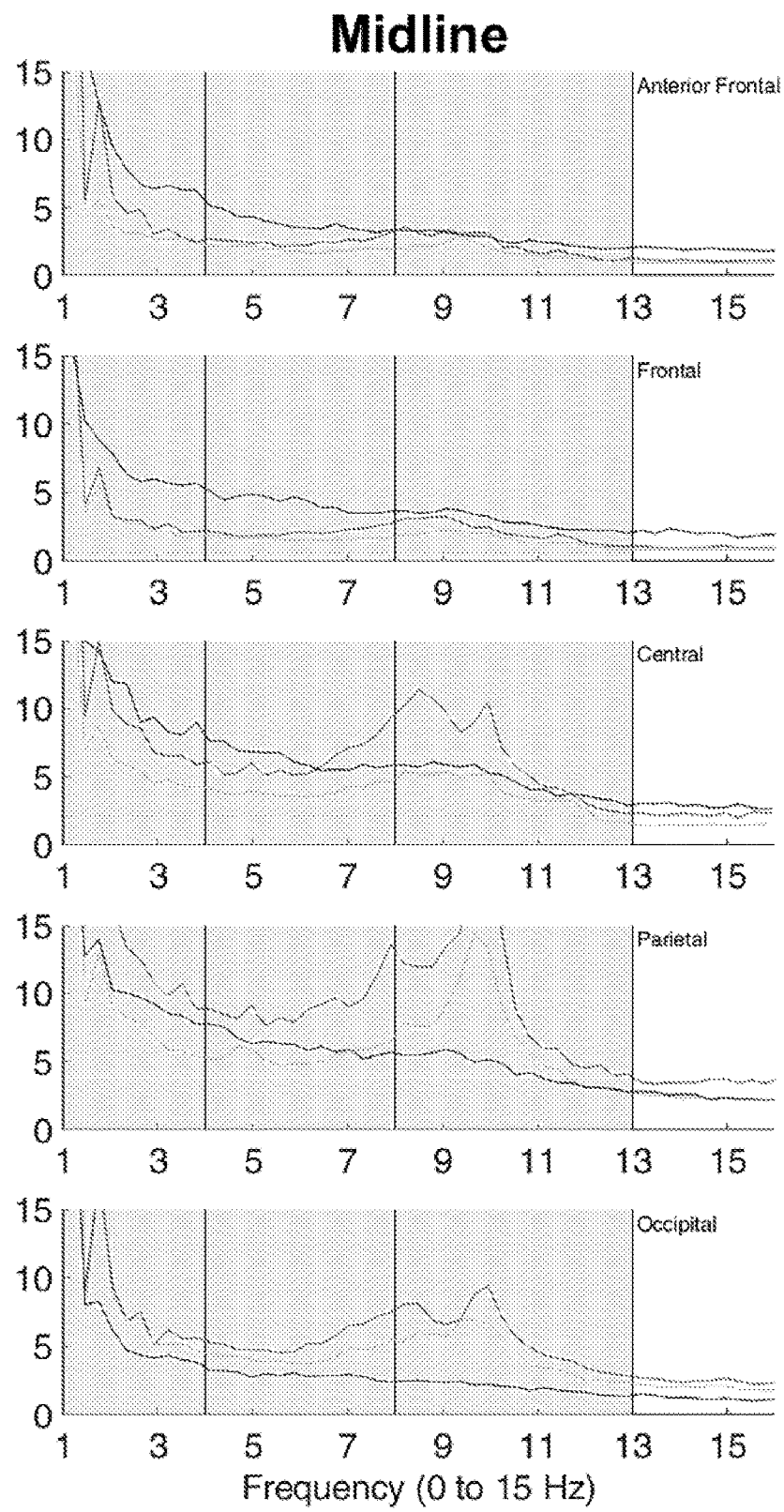

FIGS. 15A-15C provide an example of a patient who showed very focal atypical brain activity at the sub-acute exam (left posterior temporal region) but with the four month follow-up exam indicating that atypical brain activity at the sub-acute exam was fairly widespread, demonstrated via a decrease in the alpha activity in many brain regions (and associated change in maximum Z-scores) from the sub-acute to sub-chronic exam. The solid black arrows indicate abnormally increased alpha activity at the acute/subacute exam.

FIGS. 16A-16D show for central locations the amplitude spectrum from 3 consecutive 5 minute resting-state eyes-closed runs in four adolescents.

DETAILED DESCRIPTION OF THE INVENTION

Mild traumatic brain injury (mTBI) (e.g., concussion) can result from blunt force trauma to the head or nonimpact acceleration/deceleration, with resultant closed-head injury and disturbance of consciousness. mTBI is a common injury that can impact academics, behavior, and cognition. The cause of mTBI is varied and includes motor vehicle crashes, sport-related injuries, falls, and assaults. These myriad lower-energy mechanisms of injury result in the above clinical manifestations when presenting for care (Corwin, et al., J. Pediatrics (2015) 166:1221-1225; Master, et al., Clin. Pediatrics (2016) 55:260-267; Zemek, et al., JAMA (2016) 315:1014-1025). The Centers for Disease Control and Prevention estimates that up to 3.6 million concussions occur annually (Langlois, et al., J. Head Trauma Rehab. (2006) 21:375-378; Faul, et al., Handbook Clinical Neurol. (2015) 127:3-13). The majority of these injuries occur in youth 5-18 years of age, with those 11-18 years of age representing the largest proportion of those injured (Faul, et al., Handbook Clinical Neurol. (2015) 127:3-13). Adolescents may be more vulnerable to the long-term effects of brain injury, as adolescents recover more slowly than adults, and thus adolescents tend to be more adversely affected by mTBI (Field, et al., J. Pediatrics (2003) 142:546-553).

Concussion is primarily a dichotomous clinical diagnosis, relying on a patient's report of symptoms as well as quantitative clinical assessments that have components that are dependent on the effort of the injured youth and/or are influenced by learning effects (Sports-Related Concussions in Youth: Improving the Science, Changing the Culture. Ed. Graham, et al. (2014) Washington DC; Gioia G.A., Pediatric Ann. (2012) 41:198-203). Limitations are that self-report provides no direct information regarding the brain regions affected or the mechanisms constituting the brain injury. For these reasons, the current clinical 'best practice' approach to the diagnosis of concussion is unsatisfactory, and objective diagnostics are needed to identify pathophysiologic brain changes associated with youth concussion at the individual level and to provide a method to track changes in brain pathology across time (Maruta, et al., Frontiers Human Neurosci. (2016) 10:35; Hulkower, et al., Amer. J. Neuroradiol. (2013) 34:2064-2074). Optimal brain function requires a delicate balance between excitatory and inhibitory neurotransmission (E/I balance), with E/I balance essential for the induction and maintenance of neural oscillations that support cognitive function. E/I balance is disrupted in concussion. Adult clinical and preclinical studies indicate that physiologic recovery from these neurometabolic changes may occur on the order of days to a week. There is emerging evidence, however, that this recovery may take up to a month in youth and that a notable subset (10-20%) show full clinical recovery only beyond this time frame (Maugans, et al., Pediatrics (2012) 129:28-37; McCrea, et al., J. Intl. Neuropsychol. Soc. (2013) 19:22-33). Adult studies indicate that the assessment of neural brain activity via the use of magnetoencephalography (MEG) identifies abnormal brain activity in individuals with mTBI at the individual level. MEG is a non-invasive functional imaging technique that measures the neuronal current in gray matter with high temporal resolution (<1 ms) and good spatial localization accuracy (2-3 mm at cortical level) (Leahy, et al., Electroencephalography Clin. Neurophysiology (1998) 107:159-173). MEG studies have shown that MEG is highly sensitive to abnormal delta signals (1-4 Hz) resulting from brain injury affecting cortical neural dynamics. Although large-amplitude delta activity during the waking state is indicative of compromised brain tissue, some delta activity is seen in most awake adults and is thought to reflect a 'normal' range of low-frequency neural communication. Notably, once a normative database is established, particularly with a Z-score-based analysis, comparison of individual data against scores from a demographically matched control group allows fine distinctions and comparisons unattainable by clinical observation or traditional neuroimaging alone (Wienbruch, et al., Clin. Neurophysiol. (2003) 114:2052-2060).

An automated whole-brain MEG imaging approach for detecting abnormal delta activity at the individual level for adults with chronic mTBI has been used (Huang, et al., NeuroImage (2006) 31:1025-1037). The voxel-based source images were obtained using a MEG source localization method called VESTAL (VEctor-based Spatio-Temporal Analysis of L1-minimum). Using this approach, abnormal delta activity was found in 84.5% of mTBI adult patients (data obtained during the chronic stage) (Huang, et al., Neuroimage Clin. (2014) 5:109-119). MEG detection rates were markedly higher than the ~10% rate using a conventional clinical neuroimaging approach in the same mTBI adults (MRI and CT). Associations between high delta activity and impaired cognitive ability (executive tasks and processing speed) have also been observed (Robb-Swan, et al., J. Neurotrauma (2015) 32:1510-1521).

Methods for creating and using an age-appropriate adolescent normative database are provided herein for identifying abnormal neural activity in adolescents with acute/sub-acute mTBI at the individual level. Functional and structural imaging measures may be obtained at an acute (e.g., within 72 hours), sub-acute (e.g., about 3 days to about 4 weeks, particularly about 7 days to about 2 weeks), and sub-chronic (e.g., about 1 month to about 6 months, particularly about 3 to about 5 months, more particularly about 4 months) post-concussion period. The 4-month time point was selected given that the natural history of acute concussion in children may take up to 1 month for recovery (Maugans, et al., Pediatrics (2012) 129:28-37; Henry, et al., Neurosurgery (2016) 78:232-241; Meier, et al., JAMA Neurology (2015) 72:530-538). In addition, the Diagnostic and Statistical Manual of Mental Disorders (DSM-5) defines post-concussion syndrome (PCS) in cases where symptoms remain 3 months after injury, with emerging evidence that brain function/structure measures are associated with PCS. Thus, by 4 months post-injury, the majority of adolescents with mTBI will have either recovered or will meet diagnostic criteria for PCS.

Herein, whole-head EEG may be used (e.g., simultaneously) with MEG. Although an exclusive placement of EEG sensors at frontal sites may be sufficient for a large number of individuals with mTBI, as frontal regions are more likely to be injured than other brain regions, such a procedure is likely suboptimal for the many individuals with mTBI without frontal brain damage. Studies focusing only on frontal EEG measures may also have difficulty detecting alpha abnormalities, as parietal-occipital regions contain the primary and strongest resting state alpha neural generators. Collecting whole-brain MEG and EEG provides a more comprehensive examination of brain activity in concussion, including source-space analyses precluded by low-channel EEG.

Normative MEG and/or EEG whole-brain, source-space alpha database (optionally with delta, theta, and/or beta measures) for subjects (e.g., adolescents) may be established to demonstrate neural circuit abnormalities at the single-subject level in subjects reporting clinical symptoms due to mTBI. The ability to objectively diagnose concussion will enable timely identification and will define a clinical phenotype throughout the course of recovery.

In accordance with the instant invention, methods of detecting, monitoring, and/or diagnosing a traumatic brain injury, particularly a mild traumatic brain injury (e.g., concussion), in a subject are provided. As used herein, a traumatic brain injury refers to an acquired brain injury or a head injury, particularly when a trauma causes damage to the brain. Examples of trauma includes, without limitation, post-head trauma, impact trauma, and other traumas to the head such as, for example, traumas caused by accidents and/or sports injuries, traumas incurred on the battlefield (e.g., explosions, bombs, explosive devices, etc.), concussive injuries, penetrating head wounds, brain tumors, stroke, heart attack, meningitis, viral encephalitis, and other conditions that deprive the brain of oxygen. In a particular embodiment, the trauma is an external, physical force or blow, particularly to the head. In a particular embodiment, the traumatic brain injury is caused by blunt force trauma to the head or nonimpact acceleration/deceleration.

The damage to the brain can be focal (confined to one area of the brain) or diffuse (involving more than one area of the brain). Clinically, traumatic brain injury can be rated as mild, moderate or severe. For example, a traumatic brain injury may be rated based on variables that include duration of loss of consciousness (LOC), Glasgow Coma Score (GCS; e.g., mild 13-15; moderate=9-12; severe=≤8), and/or post-traumatic stress amnesia (see, e.g., Levin et al. (1979) J. Nervous Mental Dis., 167:675-84; Holm et al. (2005) J. Rehabil. Med., 37:137-41). In a particular embodiment, the traumatic brain injury is mild or moderate, particularly mild.

In some embodiments, the traumatic brain injury can be chronic, where the brain is subject to repeated traumatic injury to the brain. Generally, chronic traumatic brain injury is typically a mild to moderate form of closed brain injury repeatedly suffered by a subject (e.g., athlete (e.g., football player), soldier, etc.), resulting in increased incidence of impaired motor, cognitive, and/or behavioral impairments months to years following the traumatic brain injuring events. Individuals subjected to such chronic brain injury appear to have increased susceptibility to certain neurological disorders, such as Alzheimer's disease, chronic traumatic encephalopathy (CTE), and/or Parkinson's Disease.

In a particular embodiment, the traumatic brain injury results from a closed head injury. The closed head injury may be transient or prolonged. A "closed head injury" refers to a brain injury when the head suddenly and violently makes contact with an object but the object does not break through the skull. In some embodiments, the closed head injury is a concussion or contusion. A concussion is often a mild form of traumatic brain injury resulting in temporary impairment of neurological function which quickly resolves by itself, and where there are generally no gross structural changes to the brain as the result of the condition. A contusion is a distinct area of swollen brain tissue mixed with blood released from broken blood vessels. A contusion can also occur in response to shaking of the brain back and forth within the confines of the skull, an injury referred to as "contrecoup." As used herein, a closed head injury refers to an injury due to an external, physical trauma and does not encompass brain injury resulting from "internal" forces such as ischemia/reperfusion and stroke.

In a particular embodiment, the methods of the instant invention comprise measuring at least the alpha activity/power (8-13 Hz or 8-12 Hz) of the subject's brain. In a particular embodiment, the methods of instant invention comprise measuring brain activity in the subject by magnetoencephalography (MEG) and/or electroencephalography (EEG), particularly whole brain. In a particular embodiment, the subject is 10 or more years of age. In a particular embodiment, the subject is an adolescent. In a particular embodiment, the resting state brain activity is measured, particularly the eyes-closed, resting state brain activity of the subject. In a particular embodiment, the alpha activity/power (8-13 Hz or 8-12 Hz) and, optionally, other frequencies such as delta (1 to 4 Hz), theta (4 to 8 Hz), and/or beta (12 to 30 Hz) are measured. In a particular embodiment, the alpha activity/power (8-13 Hz or 8-12 Hz) and the theta (4 to 8 Hz) and/or beta (12 to 30 Hz) activities are measured. In a particular embodiment, brain activity is examined in source versus sensor space as this approach reduces non-brain artifact in the neural measures (e.g., muscle and heartbeat activity) as well as provides the spatial resolution needed to identify local as well as more diffuse brain trauma. In a particular embodiment, the alpha power and/or other frequencies are measured in z-scores. In a particular embodiment, the hemisphere difference is measured (e.g., left minus right frontal lobe z-score). The measured alpha power and/or other frequencies may be compared to controls (e.g., subjects without a head and/or brain injury) and/or compared to the subject at a different timepoint. The controls may be age (e.g., adolescent) and/or sex-matched to the subject. In a particular embodiment, the method further comprises treating the patient if diagnosed with a concussion (e.g., administering pain or headache medication (e.g., acetaminophen) and/or prescribing rest and/or consumption of fluids).

As explained herein, it is desirable to measure brain activity in the subject throughout the whole brain, particularly at high density. In certain embodiments, the methods comprise measuring brain activity outside of the frontal lobe. In certain embodiments, the methods comprise measuring brain activity in at least two, three, or all four of the major lobes of the brain (e.g., frontal lobe, temporal lobe, parietal lobe, and occipital lobe). In certain embodiments, the methods comprise measuring brain activity in at least the major lobes of the brain (e.g., frontal lobe, temporal lobe, parietal lobe, and occipital lobe) as well as midline brain regions. In certain embodiments, the methods comprise measuring brain activity in at least the left and right hemispheres. In certain embodiments, the methods comprise measuring brain activity in the left and right hemispheres and the midline.

In certain embodiments, the methods comprise measuring brain activity in at least 9, 10, 11, 12, 13, 14, 15, 16, 17, 18, 19, 20, 21, 22, 23, 24, 25, 26, 27, 28, 29, 30, or more distinct locations (spaces) within the whole brain. The locations within the brain may be scattered across the whole brain (e.g., cerebral cortex). In a particular embodiment, the locations span from the anterior to the posterior. The locations within the brain may be approximately equidistant from each other. The locations may be divided equally among the left and right hemispheres or may be divided equally among the left hemisphere, the right hemisphere, and the midline. Examples of locations to be measured include, without limitation, frontal lobe, anterior frontal lobe, posterior frontal lobe, temporal lobe, anterior temporal lobe, central, posterior temporal lobe, parietal lobe, and occipital lobe.

FIG. 1 provides a schematic of the brain activity in traumatic brain injury and provides possible diagnostic outcomes based on alpha and/or other frequency (e.g., delta power) measurements. An increase in the alpha power in the subject compared to control subjects without a brain injury (e.g., within or exceeding a 90% or 95% confidence interval) indicates that the subject has a mild traumatic brain injury. The amount of increase in the alpha power may be correlated to the severity of the mild traumatic brain injury. In a particular embodiment, the alpha power is measured during the sub-acute post-concussion period. A decrease in the alpha power in the subject from the sub-acute post-concussion period to the sub-chronic post-concussion period indicates brain recovery and an improvement in the subject's diagnosis. If the decrease in alpha power in the subject is associated with an increase in the other frequencies (e.g., delta and/or theta power) compared to control subjects without a brain injury, the subject has a classical traumatic brain injury with typical residual symptoms. If the decrease in alpha power in the subject is associated with other frequencies (e.g., delta power) similar to control subjects without a brain injury, the subject has a good diagnosis with rapid brain recovery. A failure of the increased alpha power to decrease and/or return to control subjects' levels is indicative of a poor diagnosis for the subject with a failure of brain recovery and continued concussion symptoms.

The methods of the instant invention can be performed at more than one timepoint after the purported traumatic brain injury (e.g., a timecourse can be obtained). By taking multiple assessments, the recovery from the traumatic brain injury and/or efficacy of a treatment can be monitored (e.g., by determining if the alpha and/or other frequencies (e.g., delta and/or theta power) returns to normal (e.g., baseline for the subject) or control levels). Control measurements and/or baseline measurements may also be taken multiple times (e.g., more than once).

In accordance with another aspect of the instant invention, methods of screening therapies against a traumatic brain injury, particularly a mild traumatic brain injury, in a subject are provided. In a particular embodiment, the subject is 10 or more years of age. In a particular embodiment, the subject is an adolescent. In a particular embodiment, the method comprises administering a therapy (e.g., administering a compound and/or a non-pharmacological intervention or therapy) to the subject before and/or after the purported traumatic brain injury and performing the above methods for measuring brain activity. The screening methods may further comprise performing the above methods for measuring brain activity to establish a baseline prior to the administration of the therapy. Brain activity measurements can be performed at more than one timepoint after the administration of the therapy (e.g., a timecourse of measurements can be performed). By taking multiple assessments, the recovery from the traumatic brain injury and/or efficacy of a treatment can be monitored (e.g., by determining if the brain activity returns to normal). Any kind of compound or molecule may be tested as a candidate therapeutic in the methods of the present invention, including, but not limited to, natural or synthetic chemical compounds (such as small molecule compounds), organic and inorganic compounds and molecules, and biological macromolecules (such as saccharide-, lipid-, peptide-, polypeptide- and nucleic acid-based compounds and molecules). Examples of non-pharmacological intervention or therapy include, without limitation, behavioral therapy, physical therapy, transcranial direct current stimulation, etc.

In a particular embodiment, the screening methods comprise measuring at least the alpha activity/power (8-13 Hz or 8-12 Hz) of the subject's brain. In particular embodiment, the screening methods comprise measuring brain activity in the subject by magnetoencephalography (MEG) and/or electroencephalography (EEG). In a particular embodiment, the resting state brain activity is measured, particularly the eyes-closed, resting state brain activity of the subject. In a particular embodiment, the alpha activity/power (8-13 Hz or 8-12 Hz) and, optionally, other frequencies such as delta (1 to 4 Hz), theta (4 to 8 Hz), and/or beta (12 to 30 Hz) are measured. In a particular embodiment, the alpha activity/power (8-13 Hz or 8-12 Hz) and the theta (4 to 8 Hz) and/or beta (12 to 30 Hz) activities are measured. In a particular embodiment, brain activity is examined in source versus sensor space as this approach reduces non-brain artifact in the neural measures (e.g., muscle and heartbeat activity) as well as provides the spatial resolution needed to identify local as well as more diffuse brain trauma. In a particular embodiment, the alpha power and/or delta power are measured in z-scores. In a particular embodiment, the hemisphere difference is measured (e.g., left minus right frontal lobe z-score). The measured alpha power and/or other frequencies (e.g., delta power) may be compared to controls (e.g., subjects without a head and/or brain injury) and/or compared to the subject at a different timepoint (e.g., before administration of the therapy). The controls may be age (e.g., adolescent) and/or sex-matched to the subject. In a particular embodiment, a decrease in the alpha power in the subject and/or a return to control subjects' levels (particularly when different from the control's normal age-related maturational change in alpha power) indicates that the administered therapy is effective in treating traumatic brain injuries. A failure of the increased alpha power to decrease and/or return to control subjects' levels is indicative of an ineffective therapy.

Definitions

The singular forms "a," "an," and "the" include plural referents unless the context clearly dictates otherwise.

As used herein, the term "subject" refers to an animal, particularly a mammal, particularly a human. As used herein, a "adolescent" refers to a human of less than 21 years of age, particularly about 13 to about 19 years of age or about 13 to about 17 years of age.

As used herein, "cognitive impairment" refers to an acquired deficit in at least one of the following: memory function, problem solving, orientation, and abstraction. The deficiency typically impinges on an individual's ability to function independently.

The term "pathology" refers to any deviation from a healthy or normal condition, such as a disease, disorder, syndrome, or any abnormal medical condition.

The term "treat" as used herein refers to any type of treatment that imparts a benefit to a patient suffering from an injury (e.g., a traumatic brain injury), including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury (e.g., a traumatic brain injury) resulting in a decrease in the probability that the subject will develop conditions associated with the injury.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated traumatic brain injury in a patient.

As used herein, "diagnose" refers to detecting and identifying a disease or disorder in a subject. The term may also encompass assessing, evaluating, and/or prognosing the status (progression, regression, stabilization, response to treatment, etc.) of the disease or disorder in a patient.

As used herein, the term "prognosis" refers to providing information regarding the impact of the presence of a disease or disorder (e.g., traumatic brain injury) on a subject's future health (e.g., expected morbidity or mortality, the likelihood of developing a disease or disorder (e.g., cognitive impairment), and the severity of the disease or disorder). In other words, the term "prognosis" refers to providing a prediction of the probable course and outcome of the disease or the likelihood of recovery from the disease or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The following example describes illustrative methods of practicing the instant invention and is not intended to limit the scope of the invention in any way.

EXAMPLE

Recent research examining neural activity measures to identify brain injury following trauma show promise. For example, the BrainScope® EEG device (Hanley, et al. (2018) J. Neurotrauma, 35:41-47; Hanley, et al. (2017) Acad. Emerg. Med., 24:617-627) uses neural measures obtained from 5 frontal electrodes, discriminant function analysis identifies adults with mTBI (mean age of adults in normative database is 45 years) likely to have an abnormal CT, with higher Brain Function Index scores associated with more post-concussion symptoms. Although this method is of interest, most individuals with mTBI have a normal CT. Thus, this method likely identifies individuals with severe TBI. It is also of note that although an exclusive placement of EEG sensors at frontal sites may be sufficient for a number of individuals with mTBI, as frontal regions are more likely to be injured than other brain regions (Levin, et al. (1992) J. Neurol. Neurosurg. Psych., 55:255-262), such a procedure will be insufficient for the many individuals with mTBI without frontal brain damage. Finally, sensor-space measures do not provide information about the specific brain regions injured. Techniques to provide measures of brain activity in source space are of note in that these methods remove artifact (e.g., muscle activity) and also provide information about the specific brain region(s) injured.

Resting-state sub-acute and then sub-chronic MEG data were obtained from adolescents (13-17 years old) diagnosed with mTBI. Three 5-minute eyes-closed datasets were obtained within 14 days of concussion (sub-acute stage) and then at approximately 4 months following concussion (sub-chronic stage). An advantage of focusing on adolescents is the low incidence of previous concussion. Indeed, all of these mTBI participants reported that this was their 1st concussion. Thus, the brain imaging data provides greater insight into the primary effects of concussion. An age-matched male normative resting-state database (N=21) was also obtained. FIGS. 2 to 7 show MEG resting-state measures from 6 adolescents with mTBI. Each image also shows the normative (N=21) database amplitude spectrum plots from 1 to 15 Hz (age and sex-matched controls), showing the control mean amplitude spectrum and the control two standard deviation confidence interval (CI). Amplitude spectrum are shown from 15 brain locations (anterior to posterior), with frequency on the x axis (Hz) and strength of neural activity on the y axis (amplitude). At each brain location, overlaid is the resting-state amplitude spectrum from an adolescent with mTBI, with resting-state measures obtained at a sub-acute and sub-chronic exam. Frequencies where atypical neural activity is observed in the patient are marked with significantly high Z-scores (ps<0.05). In all patients, normalization of alpha activity is observed from the sub-acute to the sub-chronic period, indicating recovery of brain activity. Atypical low-frequency brain activity at the sub-acute and/or sub-chronic period in many subjects also indicates brain injury (see, for example, FIGS. 2, 3, and 4).

Three features are of note. First, via source localization resting-state neural activity is examined in brain space and not sensor space (EEG or MEG sensors). Second, significantly increased alpha activity (8 to 12 Hz alpha band) is observed at the acute/sub-acute post-concussion exam at many brain locations. The solid black arrow in FIG. 2 indicates the abnormally increased alpha activity at the acute/subacute exam at a left posterior locations (in other Figures, the arrow in alpha band show abnormally increased alpha activity at other locations), with alpha activity at the ~4-month exam indicating a normalization of alpha rhythms (power and frequency). Notably, the 16-year-old patient shown in FIG. 3 still exhibited abnormal alpha activity at the 4 month period, but this subject sustained a second head injury during the 4 month interval. Accordingly, the 4-month pattern seen in FIG. 3 is indicative of the more recent head injury.

Third, in the patients shown in FIGS. 2 to 6, significantly increased delta activity (1 to 4 Hz) is observed at the 4-month post-concussion exam in several brain regions, with the black dashed arrow indicating the abnormally increased delta activity. Atypical low-frequency brain activity at the sub-acute and/or sub-chronic period in many subjects also indicates brain injury (see, for example, FIGS. 2 to 5).

FIGS. 8 and 9 show two additional examples of sub-acute resting-state neural measures from adolescents with mTBI (sub-chronic MEG measures not obtained). Each image shows the normative sample resting-state amplitude spectrum plots from 1 to 15 Hz (age and sex-matched controls), showing the control mean amplitude spectrum and the control two standard deviation confidence interval (CI). Amplitude spectrum are shown from 15 brain locations (anterior to posterior), with frequency shown on the x axis (Hz) and strength of neural activity on the y axis (amplitude). At each brain location, overlaid are the resting-state amplitude spectrum from an adolescent with mTBI obtained at a sub-acute exam. Frequencies where atypical neural activity is observed in the patient with mTBI are marked via Z-scores. Atypical low-frequency and alpha-band brain activity at the sub-acute exam indicate brain injury.

Although examining EEG or MEG neural measures in source space removes artifact such as muscle or heartbeat artifact, other preprocessing procedures can be used to remove non-brain artifact from the raw EEG or MEG data. For example, for MEG and EEG analyses, a three-step process can be employed for removal of artifact (Cornew, et al., J. Autism Dev. Disord. (2012) 42:1884-1894). First, participants' raw EOG data can be visually examined and epochs contaminated by blinks, saccades, or other significant EOG activity removed. Second, blind to diagnosis, participants' data can be visually inspected for muscle-related activity, and data containing muscle activity can be removed. Third, any additional artifacts can be rejected by amplitude criteria (e.g., for MEG amplitude 1,200 fT/cm).

With respect to obtaining measures of neural activity in source space an example is provided. For example, to decompose the 275-channel MEG and 64-channel EEG data into a smaller number of measures, a source model in standard space with 15 regional sources can be used to project each participant's raw MEG and EEG surface data into brain source space where the waveforms are the modeled source activities. These regional sources are not intended to correspond to precise neuroanatomical structures but rather to represent neural activity at coarsely defined regions (lobar spatial sensitivity) and to provide measures of brain activity with better signal separation and with a higher SNR than afforded at the sensor level (Scherg, et al. Electroencephalography Clin. Neurophysiol. Supp. (1996) 46:127-137; Scherg, et al., Brain Topography (1991) 4:143-150; Scherg, et al., Brain Topography (1993) 5:419-423). A Fast Fourier Transform can be applied to overlapped, artifact-free, two-second epochs of continuous data for each of the two (MEG) or three (EEG) orthogonally oriented time series at each regional source. Each mean power spectrum can be summed to yield a delta and alpha total power value. To identify abnormal alpha activity, for each adolescent with mTBI, their power spectrum maps can be converted into a Z-score map using the mean and SD values from the respective normative database. As previously detailed, in addition to examining brain activity at specific brain regions, the brain measures can be combined to derive other measures of interest, with hemisphere-difference Z-score maps providing one example.

Given that the brain region(s) damaged in an event resulting in a concussion often cannot be determined based on a report of the of accident or self report, and given that animal studies show that brain injury after a concussion often has a diffuse component (due to sheering of white matter; Hulkower, et al., Amer. J. Neuroradiology (2013) 34:2064-2074), assessment of brain injury requires an assessment of the entire brain. Whereas with MRI and CT a full image of the brain is easily obtained, when obtaining electrophysiology data this requires obtaining high-density EEG or MEG data to record measures of neural activity from as many parts of the brain as possible. Given that neural activity from different parts of the brain superimposes at the EEG or MEG sensor level (and thus potentially averaging brain activity from injured and non-injured brain areas at the sensor level), analyses that provide measures of brain activity in the brain (in source space) are optimal. Analyzing data in source space also provides a signal processing advantage, 'removing' non-brain activity such as muscle activity from the EEG and MEG brain measures.

Given the possibility of diffuse as well as focal brain injury, once in source space, the spatial resolution needs to be sufficiently high. Spatial resolution that provides clinically relevant sensitivity at a lobar versus a likely too-detailed millimeter level can characterize brain pathology. FIGS. 10 and 11 provide examples of clinical errors obtained when using too sparse a spatial image. FIGS. 10A-10C and 11A-11C show MEG source data for two adolescents with mTBI, showing the resting-state amplitude spectrum for 9 regions of the brain: left and right anterior, central, posterior as well as midline brain regions. FIGS. 10D-10F and 11D-11F show data from the same patients for a denser source image (i.e., 15 brain regions). All figures show the mean and 2 standard deviation confidence intervals from age-matched controls as well as the patient's amplitude spectrum, with frequencies significantly different from the normative sample marked (i.e., high Z-scores). Comparison of the FIGS. 10A-10C and 11A-11C with FIGS. 10D-10F and FIGS. 11D-11F shows that too sparse a source image misses brain regions showing abnormality (i.e., indicated by high Z-scores).

Comparison of brain activity at specific brain regions between a patient with mTBI to a normative database allows quantitative assessment whether brain activity is atypical at a specific brain region. Knowledge of normal brain function, however, can be used to derive measures that may show greater sensitivity to brain pathology than examining activity at a single region. As an example, resting-state neural brain activity (such as amount of activity at a given frequency) is generally symmetric between the left and right hemisphere. Marked deviation from symmetry is of clinical concern. As an example, a lack of symmetry in alpha activity between analogous locations of the left and right hemisphere is of clinical note, with very asymmetric alpha activity indicating abnormal brain activity. Derived measures such as a hemisphere difference measure can be quantitatively examined in patients with mTB via computing a hemisphere-difference score for all controls and comparing the patient's hemisphere-difference amplitude spectrum to the normative sample hemisphere-difference amplitude spectrum via computing a hemisphere-difference Z-score map.

FIGS. 12 to 14 demonstrate cases where hemisphere-difference Z-score can provide a clinical advantage over examination of brain activity at a single brain region. FIGS. 12A-12C, 13A-13C, and 14A-14C provide the 15 brain region source maps and FIGS. 12D, 13D, and 14D provide the hemisphere-difference Z-score maps. The patient amplitude spectrum are plotted again the control mean and two standard deviation lines. Atypically high resting-state activity (based on Z-scores) is marked. Frequency is shown on the x axis (Hz) and strength of neural activity on the y axis (amplitude).

As shown in FIG. 12, in patients with evidence of diffuse brain injury (see FIGS. 12-12C, black arrows showing high Z-scores in many brain regions), a statistically significant hemisphere-difference Z-score would indicate greater damage in one hemisphere than the other (see FIG. 12D). As shown in FIG. 13, in the absence of evidence of diffuse brain injury (see FIGS. 13A-13C, black arrows showing atypical alpha activity only in the left hemisphere), significant hemisphere-difference Z-scores would indicate focal damage (see FIG. 13D). Finally, as shown in FIG. 14, the hemisphere-difference Z-score map may be of particular interest during the sub-chronic period, as although brain activity has started to normalize.

Abnormal brain activity may not always be apparent in the regional brain Z-score maps (see FIGS. 14A-14C), the difference score may better identify residual atypical brain activity (see FIG. 14D). Of note, as the many different orientations of the many alpha neural generators is likely to produce sensor brain measures that are not directly over the neural generator (especially for EEG), assessment of asymmetric brain activity again needs to be performed in source space and not sensor space.

Given a moderate range of resting-state activity in the normative sample, in some patients with mTBI, although a high Z-score(s) may indicate abnormality, given that many controls also show some high Z-scores, single time point measurements may not provide sufficient sensitivity and/or specificity. As such, repeated measurements from the mTBI patient may be taken. As shown in FIG. 15 as an example, although at the subacute exam there is evidence of atypical resting-state activity (left posterior temporal location), comparison of the sub-acute to sub-chronic resting-state activity indicates normalization of alpha activity throughout the brain. As changes in resting-state activity across a relatively short period of time (e.g., 4 months) are unexpected in controls, the sub-acute to sub-chronic changes in this patient with mTBI (1) support the subacute findings of atypical brain activity and (2) demonstrate that the damage was more widespread than the subacute measures indicate. Follow-up exams can, therefore, provide a more sensitive indicator of both brain damage as well as later brain recovery or lack of full recovery.

Given possible changes in the subjects state of arousal during the MEG recording, and given the need to obtain data during an awake state, several resting-state measures can be obtained in order to acquire a robust measure of resting-state brain activity (e.g., across multiple runs there is a concern that a subject will fall asleep and thus provide non-evaluable data). FIG. 16 shows for central locations the amplitude spectrum from 3 consecutive 5 minute resting-state eyes-closed runs in four adolescents. Comparison of power spectrum show similar measures in the first three adolescents. In the fourth adolescent, the last run is distinctly different as the patient fell asleep during the final exam. Multiple datasets can be used to obtain a valid measure of resting-state activity.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting and treating an acute or sub-acute mild traumatic brain injury in a subject comprising
   a) measuring an alpha activity in the brain of said subject, wherein an increase in the alpha activity in the brain of said subject compared to control subjects without a brain injury or to a baseline of said subject is indicative of said patient subject having the acute or sub-acute mild traumatic brain injury, wherein said alpha activity is measured when the subject is in a resting state; and
   b) administering a pain or headache medication to the subject with the increase in the alpha activity in the brain compared to the control subjects without the brain injury or to the baseline of said subject.

2. The method of claim 1, wherein said subject is an adolescent.

3. The method of claim 1, further comprising measuring a delta, theta, and/or beta activity of the brain of said subject.

4. The method of claim 1, wherein said alpha activity is measured by magnetoencephalography (MEG) and/or electroencephalography (EEG).

5. The method of claim 1, wherein said resting state is in an eyes-closed, resting state.

6. The method of claim 1, wherein more than one measurement of the alpha activity of the brain of the subject is performed at different times.

7. The method of claim 6, wherein at least one measurement of the more than one measurement of the alpha activity of the brain of the subject is performed during a sub-acute post-concussion stage and at least one measurement of the alpha activity of the brain of the subject is performed during a sub-chronic post-concussion stage.

8. The method of claim 1, wherein the alpha activity of the brain is measured in at least 15 locations.

9. The method of claim 1, wherein the alpha activity of the brain is measured in at least the frontal lobe, the temporal lobe, the parietal lobe, and the occipital lobe of the brain of the subject.

10. A method for detecting and treating an acute or sub-acute mild traumatic brain injury in a subject consists of
    a) measuring an alpha activity in the brain of said subject, wherein an increase in the alpha activity in the brain of said subject compared to control subjects without a brain injury or to a baseline of said subject is indicative of said patient subject having the acute or sub-acute mild traumatic brain injury, wherein said alpha activity is measured when the subject is in a resting state; and
    b) administering a pain or headache medication to the subject with the increase in the alpha activity in the brain compared to the control subjects without the brain injury or to the baseline of said subject, thereby indicating said subject has mild traumatic brain injury.

11. The method of claim 1, further comprising measuring a beta activity of the brain of said subject.

* * * * *